United States Patent [19]

Henrie, II et al.

[11] Patent Number: 5,627,189

[45] Date of Patent: May 6, 1997

[54] INSECTICIDAL 5-SUBSTITUTED-2,4-DIAMINOPYRIMIDINE DERIVATIVES

[75] Inventors: Robert N. Henrie, II, East Windsor; Clinton J. Peake, Trenton; Thomas G. Cullen, Milltown; Albert C. Lew, Princeton Junction; Munirathnam K. Chaguturu, Lawrenceville, all of N.J.; Partha S. Ray, Memphis, Tenn.; Walter H. Yeager, Yardley, Pa.

[73] Assignee: FMC Corporation, Philadelphia, Pa.

[21] Appl. No.: 555,249

[22] Filed: Nov. 8, 1995

Related U.S. Application Data

[60] Division of Ser. No. 237,481, May 3, 1994, Pat. No. 5,521,192, which is a continuation-in-part of Ser. No. 985,084, Dec. 2, 1992, abandoned.

[51] Int. Cl.$^6$ .......................... A01N 43/54; A61K 31/535
[52] U.S. Cl. .......................... 514/275; 514/235.8
[58] Field of Search .......................... 514/275, 235.8

[56] References Cited

U.S. PATENT DOCUMENTS

| | | | |
|---|---|---|---|
| 4,435,402 | 3/1984 | Tsuji et al. | 424/251 |
| 4,783,468 | 11/1988 | Kristenssohn | 514/275 |
| 4,845,097 | 7/1989 | Matsumoto et al. | 514/234.2 |
| 4,895,849 | 1/1990 | Yoshioka et al. | 514/241 |
| 5,073,558 | 12/1991 | Obata et al. | 514/259 |

FOREIGN PATENT DOCUMENTS

| | | | |
|---|---|---|---|
| 1546937 | 5/1979 | United Kingdom . | |
| 2087881 | 6/1982 | United Kingdom | 514/275 |

*Primary Examiner*—Allen J. Robinson
*Attorney, Agent, or Firm*—Stanford M. Back; Robert M. Kennedy

[57] ABSTRACT

An insecticidal composition comprising, in admixture with an agriculturally acceptable carrier, an insecticidally effective amount of a compound of the formula:

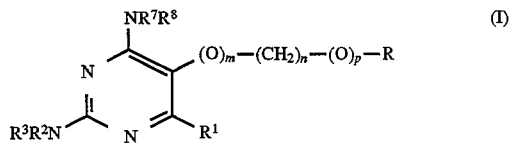

(I)

wherein R, $R^1$, $R^2$, $R^3$, $R^7$, $R^8$, m, n, and p are as defined herein, and agriculturally acceptable salts thereof, and methods of using the same.

10 Claims, No Drawings ns
INSECTICIDAL 5-SUBSTITUTED-2,4-DIAMINOPYRIMIDINE DERIVATIVES

CROSS-REFERENCE TO RELATED APPLICATION

This application is a divisional a U.S. application Ser. No. 08/237,481 filed May 3, 1994 in the names of Henrie et al, now U.S. Pat. No. 5,521,192, issued May 28, 1996, which in turn is a continuation in part of U.S. application Ser. No. 985,084, filed Dec. 2, 1992 (now abandoned).

BACKGROUND OF THE INVENTION

This invention relates to pyrimidine compounds and compositions containing the same which are useful for controlling insects in agricultural crops. Still more particularly, this invention relates to certain 2,4-diaminopyrimidine compounds and compositions, and their use as insecticides against a variety of insects, especially larvae such as the tobacco budworm. Numerous of these diaminopyrimidine compounds employed herein, and their preparation, have been described in the literature for use in a variety of fields, but not as insecticides.

SUMMARY OF THE INVENTION

In accordance with the present invention it has been found that 5-substituted-2,4-diaminopyrimidines, and agriculturally acceptable salts thereof, when present in insecticidally effective amounts, and with a suitable agricultural carrier, are useful as active ingredients in the insecticidal compositions and methods of this invention. These pyrimidines may be represented by the following formula:

$$\underset{R^3R^2N}{\overset{NR^7R^8}{\underset{N}{\bigvee}}}\overset{(O)_m-(CH_2)_n-(O)_p-R}{\underset{R^1}{\bigvee}} \quad (I)$$

wherein
R is
(a) hydrogen, straight or branched chain alkyl, cycloalkyl, polycycloalkyl (e.g., adamantyl), cyano, morpholinyl, alkylsilane, arylsilane, phenyl, or substituted phenyl of the formula:

$$\underset{Y}{\overset{V}{\underset{\bigvee}{\bigvee}}}\overset{W}{\underset{X}{\bigvee}} \quad (II)$$

wherein
V, W, X, Y, and Z are independently selected from hydrogen, halogen, hydroxy, straight or branched chain alkyl, alkylsilane, alkylsilanylalkyl, alkylsulfonyl, lower haloalkylsulfonyl (e.g., $-SO_2CF_3$), phenyl, alkoxy, alkylthio, alkoxycarbonyl, alkoxyalkyl, haloalkyl (e.g., $-CF_3$), lower haloalkoxy (e.g., $-OCF_2CHF_2$), pyridinylalkyl, nitro, substituted phenylalkyl, cyano, aminocarbonyl, phenyl(hydroxyalkyl), (phenyl-, or substituted phenyl-, lower alkyl)amino, (lower alkyl) (phenyl-, or substituted phenyl-lower alkyl)amino, substituted phenoxyalkyl, heterocyclyloxy, bicycloalkoxy, $-NHC(O)R^4$, and $-NHR^5$, wherein $R^4$ is alkyl, haloalkyl, substituted phenyl, substituted phenylalkyl, or substituted phenoxyalkyl, and $R^5$ is alkyl, cycloalkyl, substituted phenylalkyl, substituted phenoxyalkyl, or pyridinylalkyl, wherein the term heterocyclyl includes 2-, 3-, or 4-pyridinyl, and 2-, 4-, or 5-pyrimidinyl and their N-oxides; or
(b) substituted phenyl lower alkyl of the formula:

$$\underset{Y^1}{\overset{Z^1}{\underset{\bigvee}{\bigvee}}}\overset{CH_{(2-q)}-(CH_3)_q-}{\underset{X^1}{\overset{V^1}{\bigvee}}} \quad (III)$$

wherein
q is 1 or 2; and,
$V^1$, $W^1$, $X^1$, $Y^1$ and $Z^1$ are independently selected from hydrogen, lower alkyl, halogen, hydroxy, lower alkoxy, lower haloalkyl, lower alkylsulfonyl, cyano, substituted phenyl, and aminocarbonyl; or
(c) naphthyl, or substituted naphthyl of the formula:

$$\underset{Z^2}{\overset{V^2}{\underset{\bigvee}{\bigvee}}}\overset{W^2}{\underset{Y^2}{\overset{}{\bigvee}}}X^2 \quad (IV)$$

wherein
$V^2$, $W^2$, $X^2$, $Y^2$, and $Z^2$ are independently selected from hydrogen, halogen, lower alkyl, lower haloalkyl, lower alkylsulfonyl, cyano, and aminocarbonyl; or
(d) thiazol-2-yl, benzothiazol-2-yl, or 5-substituted-thien-2-yl of the formula:

$$\underset{S}{\overset{}{\bigvee}}V^3 \quad (V)$$

wherein
$V^3$ is halogen, lower alkyl, lower haloalkyl, cyano, or aminocarbonyl;
and wherein
$R^1$ is hydrogen, lower alkyl, amino, phenyl, or phenyl lower alkyl;
$R^2$, $R^3$, $R^7$ and $R^8$ are independently selected from hydrogen, lower alkyl, lower alkylcarbonyl, and lower alkoxycarbonyl;
or $R^2$ and $R^3$, taken together, form the group $-R^6-O-R^6-$, wherein $R^6$ is lower alkylene;
m is 0 or 1;
n is 0 to 11; and
p is 0 or 1,
and agriculturally acceptable salts thereof (e.g., hydrochloric acid salt, ethanesulfonic acid salt, gluconic acid salt, or pamoic acid salt), with the proviso that when m, n, and p are 0, R is other than hydrogen; and with the further proviso that when m and p are 1, n must be at least 1.

Of these compounds, among the more preferred ones for use in the compositions and methods of this invention are those wherein the diaminopyrimidines are of the structure (I) above, and wherein
(i) m and p are 0;

n is 0 to 10;

R is lower alkyl, cycloalkyl, e.g., cyclohexyl; polycycloalkyl (e.g., adamantyl); naphthyl, or substituted naphthyl; phenyl, or substituted phenyl of the formula:

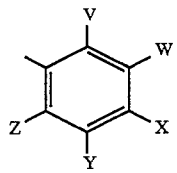
(II)

wherein

V, W, X, Y, and Z are independently hydrogen, halo (e.g., chloro); lower alkyl (e.g. methyl); lower alkoxy (e.g., ethoxy or propoxy); trihaloalkyl (r:,.g. trifluoromethyl); nitro, (phenyl-, or substituted phenyl-:lower alkyl)amino (e.g., (3,5-dichlorophenylmethyl)amino or (4-methoxyphenylmethyl)amino, wherein at least one of V to Z is not hydrogen;

$R^1$ is hydrogen, lower alkyl, or amino; and $R^2$, $R^3$, $R^7$, and $R^8$ are hydrogen, lower alkyl, lower alkylcarbonyl, or lower alkoxycarbonyl;

(ii) m is 1 and p is 0;

n is 1 to 3;

R is pentan-3-yl, cyclopentanyl, or phenyl;

$R^1$ is hydrogen, lower alkyl (e.g. methyl or ethyl), or amino; and $R^2$, $R^3$, $R^7$, and $R^8$ are hydrogen, lower alkyl, lower alkylcarbonyl, or lower alkoxycarbonyl; or (iii) m and p are 1;

n is 1 to 3;

R is substituted phenyl of the formula:

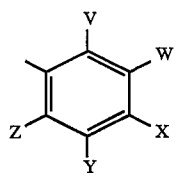
(II)

wherein

W, X, Y and Z are hydrogen, and V is trihaloalkyl;

$R^1$ is lower alkyl (e.g., methyl); and $R^2$, $R^3$, $R^7$, and $R^8$ are hydrogen, lower alkyl, lower alkylcarbonyl, or lower alkoxycarbonyl.

Particularly preferred amongst the above compounds having the structure of formula (I) above which may be employed in this invention are those which correspond to certain of the numbered compounds in Table 1 below; i.e., those wherein (iv) m, n and p are 0;

R is adamantyl;

$R^1$ is lower alkyl (e.g., methyl); and $R^2$, $R^3$, $R^7$, and $R^8$ are hydrogen (Compound 110);

(v) m and p are 0;

n is 2 or 3;

R is substituted phenyl lower alkyl of the formula:

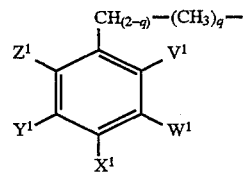
(III)

wherein q is 1 or 2; one or two of the substituents $V^1$, $W^1$, $X^1$, $Y^1$, and $Z^1$ for each compound are independently selected from halo, preferably chloro, and trihaloalkyl, preferably trifluoromethyl;

and $W^1$ or $X^1$ is substituted phenyl (Compounds 144 and 148).

$R^1$ is lower alkyl (e.g., ethyl); and $R^2$ is hydrogen, lower alkyl (e.g., methyl, ethyl), lower alkylcarbonyl, or lower alkoxycarbonyl; and $R^3$, $R^7$, and $R^8$ are hydrogen, lower alkylcarbonyl, or lower alkoxycarbonyl.

(vi) m and p are 0;

n is 3 or 4;

R is naphth-1-yl (Compounds 47, 48 and 50); or substituted phenyl of the formula:

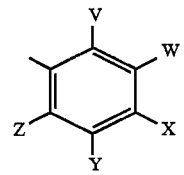
(II)

V is lower alkyl, (e.g. methyl) (Compound 123), trihaloalkyl (e.g., trifluoromethyl) (Compound 120), or cyano (Compound 162); W is phenyl (Compound 33); X is halo, preferably chloro (Compound 67)lower alkyl (e.g., methyl) (Compound 125), substituted phenyl (Compounds 164 and 170), or heterocyclyloxy (Compound 171); or V, X, and Y are halo, e.g. chloro (Compounds 34, 38, 117 and 118) or lower alkyl (e.g., methyl) (Compound 128); or V and X are halo, preferably chloro (Compounds 136 and 139); and the remaining substituents V, W, X, Y, and Z of each <compound are hydrogen;

$R^1$ is hydrogen (Compounds 47, 50, and 67), lower alkyl (e.g., methyl (Compounds 117, 120, 123, 125, and 128), or ethyl, (Compounds 33, 34, 38, and 118)) or amino (Compound 48);

$R^2$ is hydrogen, lower alkyl (e.g., methyl, ethyl), lower alkylcarbonyl, or lower alkoxycarbonyl; and $R^3$, $R^7$, and $R^8$ are hydrogen, lower alkylcarbonyl, or lower alkoxycarbonyl;

(vii) m is 1;

n is 1 or 3;

p is 0;

R is pentan-3-yl (Compounds 56 and 132) or phenyl (Compound 134);

$R^1$ is hydrogen (Compound 56) or lower alkyl (e.g., methyl) (Compounds 132 and 134); and $R^2$, $R^3$, $R^7$, and $R^8$ are hydrogen;

(viii) m and p are 1;

n is 3;

R is substituted phenyl of the formula:

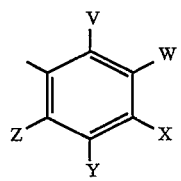

wherein

V is trihaloalkyl, e.g., trifluoromethyl, and the remaining substituents W, X, Y, and Z are hydrogen;

$R^1$ is lower alkyl, (e.g., methyl); and $R^2$, $R^3$, $R^7$, and $R^8$ are hydrogen (Compound 135).

Each of these above compounds, which are preferred because of their high insecticidal activity, may be used in controlling insects by applying to the locus where control is desired an insecticidal amount of these compounds admixed in a suitable agricultural carrier.

For purposes of this invention, as regards the above substituent groups, the following definitions apply:

The term alkyl includes straight or branched chained alkyl of.1 to 14 carbon atoms; preferably lower straight or branched alkyl of 1 to 6 carbon atoms; while halogen includes chlorine, bromine, and fluorine atoms. The term haloalkyl and haloalkoxy include straight or branched chain alkyl of 1 to 14 carbon atoms, preferably lower straight or branched alkyl of 1 to 6 carbon atoms, wherein one or more hydrogen atoms have been replaced with halogen atoms. The cycloalkyl groups include polycycloalkyl, and may be saturated or unsaturated, for example cyclohexyl, cyclohexenyl, decalinyl, or adamantyl having from about 3 to 10 carbon atoms, and may be substituted by halogen, alkyl, substituted aryl, cyano, alkoxy or the like. The term aryl and substituted aryl include phenyl and naphthyl, preferably phenyl or substituted phenyl. The term aryl also includes those aryl groups substituted with one or more alkyl, halo, alkoxy, cycloalkyl, aryl, haloalkyl, haloalkoxy, cyano, aminocarbonyl, nitro, dialkylamino, thioalkyl, alkylsulfonyl, or like moieties.

As aforestated, the present 2,4-diaminopyrimidines, when admixed with suitable carriers and applied to insect-infected crops such as cotton, vegetables, fruits or other crops are highly effective against an array of insects, particularly those shown in the tables below.

Each of the novel compounds of these additional embodiments may be prepared in the same or similar manner as those compounds of Formula I above.

DETAILED DESCRIPTION OF THE INVENTION

Synthesis of The Compounds

The compounds employed as insecticides in accordance with this invention are generally known to those skilled in the art, or may readily be prepared from these compounds by known methods. These and other methods are described in further detail in the examples below. Thus, for example, those compounds wherein m is 0 and n is 1 or more, may be prepared by one of two methods, depending on whether $R^1$ in the 6-position of the pyrimidine ring is hydrogen or one of the other defined substituents.

Those compounds wherein $R^1$ is hydrogen may be prepared by the method of Smirnow et al., "Alkylation of 3-Ethoxy-2-lithioacrylonitrile . . . ," *Synthetic Communications*, 16(10), (1986), pp. 1187–1193, by the metallation of 3-ethoxyacrylonitrile with n-butyllithium in tetrahydrofuran at about −110° C. The resulting anion is in turn treated with an excess of an optionally substituted alkyl halide, for example 3-(naphth-1-yl)propyl iodide, yielding the corresponding 1-ethoxy-2-cyano-5-(naphth-1-yl)-1-pentene. The nitrile is then condensed with guanidine hydrochloride and potassium carbonate in N,N-dimethylformamide at about 125° C., affording 5-(optionally substituted alkyl)-6-unsubstituted-2,4-diaminopyrimidines. Examples 1,3, and 6 (below) provide the details for this route.

The 1-ethoxy-2-cyano-5-(naphth-1-yl)-1-pentene may also be condensed with 1-ethylguanidine hydrochloride and potassium carbonate in dimethylformamide as previously described, yielding 5-(optionally substituted alkyl)-6-unsubstituted-2-ethylamino-4-aminopyrimidine. Example 9 provides the detail for this method of preparation of a substituted amino derivative.

Compounds wherein $R^1$ is other than hydrogen are generally prepared by a second method which requires the metallation of an optionally substituted alkanenitrile, for example, 5-(2,4,5- trichlorophenyl)pentanenitrile or 7-phenylheptanenitrile, with n- butyllithium in tetrahydrofuran at about −78° C. The resulting anion is then reacted with an ethyl (optionally substituted) alkanoate, for example ethyl propanoate or ethyl 5-phenylpentanoate, yielding the appropriately substituted α-cyanoalkanone, for example 1-(2,4,5-trichlorophenyl)-4-cyano-5-heptanone or 1,11-diphenyl-6-cyano-5-undecanone. This alkanone may then be methylated on the oxygen with diazomethane in diethyl ether, affording a 1-methoxy-1- and 2- (optionally substituted alkyl)-2-cyanoethene, for example 1-(2,4,5-trichlorophenyl)-4-cyano-5-methoxy-4-heptene or 1,11-diphenyl-5-methoxy-6-cyano-5-undecene. The thus- prepared ethene can then be condensed with guanidine hydrochloride and potassium carbonate in N,N-dimethylformamide as previously described, yielding the 5-, and 6- (optionally substituted alkyl)-2,4-diamino-pyrimidine. Examples 4, 5, 7, and 8 (below) provide the details for this method.

This second method, as described above, may also be utilized to prepare compounds wherein $R^1$ is hydrogen. This route requires the use of ethyl formate, rather than an ethyl (optionally substituted) alkanoate. Example 2 provides the detail for this method.

The above-defined compound wherein $R^1$ is amino may be prepared by the treatment of malononitrile with sodium hydride in tetrahydrofuran, followed by reaction of the thus-prepared sodium salt with an optionally substituted alkyl halide, for example, 3-(naphth-1-yl)propyl iodide, yielding a 2-cyano-(optionally substituted)alkanenitrile. The 2-cyano-(optionally substituted)alkanenitrile, for example 2-cyano-5-(naphth-1-yl)pentanenitrile, may then be treated with sodium ethoxide in ethanol and reacted with guanidine hydrochloride, yielding 2,4,6-triamino-5-(optionally substituted alkyl)pyrimidines. Example 11 provides the detail for this method.

Alternatively, there may be prepared the compound wherein m and n are 0, and R is phenyl. This compound is prepared by the reaction of benzyl cyanide and N,N-dimethylformamide dimethyl acetal in methanol. The thus-prepared 1-cyano-1-phenyl-2-N,N-dimethylaminoethene is then condensed with guanidine hydrochloride and potassium carbonate in dimethylformamide, as previously described, yielding 2,4-diamino-5-phenylpyrimidine (I). Example 10 provides the detail for this method.

A further, alternate method used to prepare a number of compounds wherein m is 1 and $R^1$ is hydrogen includes condensing 3-ethoxyacrylonitrile with guanidine hydrochloride and potassium carbonate in N,N-dimethylformamide, as previously described, yielding 2,4-diamino-pyrimidine. The pyrimidine may, in turn, be reacted with ammonium persulfate in aqueous 5N sodium hydroxide affording 2,4-diamino-5-pyrimidinyl hydrogen sulfate. The hydrogen sulfate is then treated with sulfuric acid in water yielding the corresponding 2,4-diamino-5-hydroxy-pyrimidine hydrosulfate salt. The thus-prepared 5-hydroxypyrimidine can then be reacted with an (optionally substituted) alkyl halide and potassium carbonate in N,N-dimethylformamide, yielding 2,4-diamino-5-(optionally substituted alkoxy)pyrimidines. Example 12 provides the detail for this method.

Other methods by which intermediates of the above-described compounds are shown in further detail in Examples 1–9 and 11 (below).

Compounds 90–96, which include the sub-structure —(O)$_p$— may also be prepared by methods described above, e.g., using the method of Smirnow et al., previously described, by the treatment of the lithiated 3-ethoxyacrylonitrile with a substituted-oxaalkyl halide, for example 3-(4-propylthiophenoxy)propyl iodide, yielding the corresponding 1-ethoxy-2-cyano-2-(substituted-oxaalkyl)-6-unsubstituted-2,4-diaminopyrimidines. Examples 1,3, and 6 also show this method.

Another class of compounds, represented by Compounds 100–103, 105–109, wherein m is 1, n and p are 0, and R is substituted phenyl, may be prepared in accordance with the-methods shown in Example 14. In this method, ethyl 3oxopentanoate is chlorinated with sulfuryl chloride, affording the corresponding ethyl 2-chloro-3-oxopentanoate. The ethyl 2-chloro-3-oxopentanoate is then reacted with sodium hydride, then treated with an appropriately substituted phenol, yielding ethyl 2-(substituted-phenoxy)-3-oxopentanoate. The thus-prepared ethyl pentanoate is cyclized with guanidine carbonate in ethanol, yielding 2-amino-6-ethyl-4-hydroxy-5-(substituted phenoxy)pyrimidine. The 4-hydroxypyrimidine is then chlorinated with phosphorus oxychloride, providing the corresponding 2-amino-4-chloro-6-ethyl-5-(substituted-phenoxy) pyrimidine. This compound in turn is treated with ammonia gas in ethanol under pressure, yielding 2,4-diamino- 6-ethyl-5-(substituted-phenoxy)-pyrimidine. Compounds 72–89, wherein m, n, and p are 0, and R is:

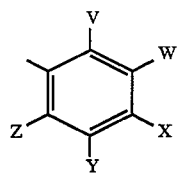

(II)

may be prepared in accordance with the methods of Example 13. In these compounds, V, Y, and Z are hydrogen, X is chloro, and W is —NHR$^5$, or —NHC(O)R$^4$; wherein R$^4$ is straight or branched chain alkyl of 4 to 10 carbon atoms in length, lower haloalkyl, substituted-phenyl, substituted-phenylalkyl, and substituted-phenoxyalkyl; and R$^5$ is straight chain alkyl, cycloalkyl, substituted-phenylalkyl, and substituted-phenoxyalkyl; and the substituents on the phenyl moiety include, preferably, halo, alkoxy, and alkylsulfonyl.

In this method, commercially available 2,4-diamino-6-ethyl-5-(4-chlorophenyl)pyrimidine is nitrated with 70% nitric acid and concentrated sulfuric acid, yielding the corresponding 2,4-diamino-6-ethyl-5-(4-chloro-3-nitrophenyl) pyrimidine. The thus-prepared nitrophenylpyrimidine is in turn reduced with stannous chloride dihydrate in 10M hydrochloric acid, yielding the corresponding 2,4-diamino-6-ethyl-5-(3-amino-4-chlorophenyl)pyrimidine. The aminophenylpyrimidine may then be treated with an appropriate acid chloride in the presence of a base in tetrahydrofuran, yielding the desired 2,4-diamino-6-ethyl-5-[3-(substituted-carbonylamino)-4-chlorophenyl]pyrimidine (wherein W is —NHC(O)R$^4$). These compounds may optionally be reduced with 1M boron-tetrahydrofuran complex in tetrahydrofuran, affording 2,4-diamino-6-ethyl-5-[3-(substituted-amino)-4-chlorophenyl]pyrimidine (wherein W is —NHR$^5$).

Example 15 teaches a method of adding a substituent to the pyrimidine-containing molecule after the pyrimidine ring is formed.

Example 16 teaches a method of preparing a hydrochloride salt of a previously prepared pyrimidine.

Example 17 is similar to the method taught by Example 5, however Example 17 is an improvement over Example 5 in that it saves two synthesis steps in the preparation of the optionally substituted alkanenitrile intermediate. Example 17 also teaches a new method of forming the pyrimidine ring which is an improvement over that taught in Examples 2 and 5. This method replaces guanidine hydrochloride and sodium carbonate/DMF with guanidine carbonate and N,N-dimethylacetamide (compare Example 2, Step E, with Example 17, Step E).

Example 18 is similar to the method taught by Example 12; however, Example 18 teaches a preparation for those compounds wherein m and p are both 1, as depicted in the structure:

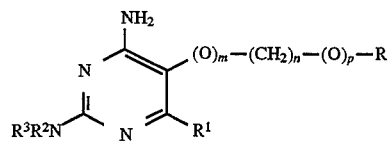

and the remaining substituents are as defined above.

Example 19 is similar to the method taught in Example 12. The compound, 2,4-diamino-5-(adamant-1-yl)-6-methylpyrimidine, prepared by the method of Example 19, is active in various tests, as shown below.

Examples 20–28 specifically disclose some of the preferred compounds, i.e., those compounds with a pI$_{50}$ value of ≧5.7 in the Diet test.

Examples 29 and 30 are similar to the method taught by Examples 4, 5, and 17; however, Examples 29 and 30 teach a preparation for those compounds wherein R is a substituted phenyl lower alkyl moiety, as depicted in the following structure:

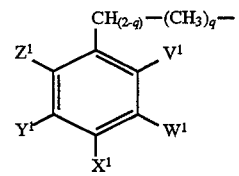

where q is 1.

Using the method taught in Example 29, a tertiary benzylic alcohol, for example 5-hydroxy-5-(3-trifluoromethylphenyl)hexanenitrile, was reduced to the corresponding arylalkanenitrile by the reaction of the alcohol with a chlorotrimethylsilane-sodium iodide-acetonitrile reagent in hexane. The arylalkanenitrile, for example, 5-(3-trifluoromethylphenyl)-hexanenitrile, was then reacted further by methods previously described to obtain the corresponding substituted-pyrimidine.

Compounds 142 to 172 may likewise be prepared by methods known to those skilled in the art. For example, those compounds prepared wherein R$^3$ and R$^8$ are the same and are straight or branched chain lower alkylcarbonyl may be prepared by the reaction of the corresponding 2,4-diaminopyrimidine with an acid anhydride, such as acetic anhydride or pivalic anhydride, in the presence of a base, yielding the targeted 2,4-di(substituted amino)pyrimidine derivatives. See, for instance, Examples 34 to 37, one which teaches a method of preparation of those compounds wherein $R^3$ and $R^8$ are as described above, and three others for compounds prepared using slight variations of the preceding examples.

EXAMPLES

The following examples, which disclose the preparation of representative compounds of this invention (Table 1), are for the purpose of illustrating known methods for the preparation of the compounds employed in the methods and formulations of this invention.

EXAMPLE 1

SYNTHESIS OF 2,4-DIAMINO-5-[3-(NAPHTH-1-YL)PROPYL]PYRIMIDINE (COMPOUND 47)

Step A Synthesis of 3-(naphth-1-yl)propyl iodide as an intermediate

Under a nitrogen atmosphere a solution of 6.8 grams (0.040 mole) of 3-(naphth-1-yl)-1-propene was stirred at 25° C., and 14 mL (0.013 mole) of 1M borane-tetrahydrofuran complex was added dropwise. The reaction mixture was maintained at 25° C. during the addition and for another hour upon completion of the addition. After this time 1 mL of methanol was added to destroy excess boron intermediates. Iodine, 7.7 grams (0.030 mole), was then added in one portion, followed by the dropwise addition of 10 mL of 3M methanolic sodium hydroxide. Upon completion of addition, the reaction mixture was stirred for five minutes and then was poured into a solution of 3.0 grams of sodium thiosulfate in 150 mL of water. The mixture was extracted with two 100 mL portions of methylene chloride. The combined extracts were dried with magnesium sulfate and filtered. The filtrate was concentrated under reduced pressure to a residual oil. The residual oil was subjected to column chromatography on silica gel. Elution was accomplished using petroleum ether. The eluate was concentrated under reduced pressure, yielding 4.0 grams of 3-(naphth-1-yl) propyl iodide. The NMR spectrum was consistent with tile proposed structure.

Step B Synthesis of 1-ethoxy-2-cyano-5-(naphth-1-yl)-1-pentene as an intermediate Under a nitrogen atmosphere a stirred solution of 1.5 mL (0.014 mole) of 3-ethoxyacrylonitrile in 45 mL of tetrahydrofuran was cooled to about −110° C., and 6.2 mL (0.015 mole) of 2.5M n- butyllithium in hexanes was added dropwise at a rate to keep the reaction mixture temperature below −65° C. Upon completion of addition, the reaction mixture was stirred for about ten minutes, and then a solution of 4.0 grams (0.014 mole) of 3-(naphth-1-yl)propyl iodide in 15 mL of tetrahydrofuran was added dropwise. Upon completion of addition, the reaction mixture was stirred at about −78° C. for two hours. After this time the reaction mixture was allowed to warm to ambient temperature as it stirred for about 16 hours. The reaction mixture was concentrated under reduced pressure, yielding a dark residual oil. The oil was passed through a short column of silica gel using methylene chloride as the eluant. The eluate was concentrated under reduced pressure to a residual oil. The oil was subjected to column chromatography on silica gel. Elution was accomplished using 2:1 methylene chloride and petroleum ether. The appropriate fractions were combined and concentrated under reduced pressure, yielding 1.0 gram of 1-ethoxy-2-cyano-5-(naphth-1-yl)-1-pentene. The NMR spectrum was consistent with the proposed structure.

Step C Synthesis of 2,4-diamino-5-[3-(naphth-1-yl)-propyl] pyrimidine (Compound 47)

Under a nitrogen atmosphere a stirred solution of 0.85 gram (0.003 mole) of 1-ethoxy-2-cyano-5-(naphth-1-yl)-1-pentene, 1.22 grams (0.013 mole) of guanidine hydrochloride, and 2.65 grams (0.01 9 mole) of potassium carbonate in 20 mL of N,N-dimethylformamide was heated at 110° C. for 20 hours. After this time the reaction mixture was analyzed by thin layer chromatography (TLC) which indicated the reaction was not complete. The reaction mixture was warmed to 125° C. where it was stirred for six hours. TLC analysis of the reaction mixture after this time indicated that the reaction was still not complete. An additional 10 mL of dimethylformamide was added, and the reaction mixture was stirred at 125° C. for an additional 64 hours. The reaction mixture was then poured into water, and the mixture was extracted with two 100 mL portions of ethyl acetate. The combined extracts were concentrated under reduced pressure, yielding a yellow solid. The solid was triturated with dichloromethane. The solid was collected by filtration and subjected to column chromatography on silica gel. Elution was accomplished with 10:1 methylene chloride and methanol. The eluate was concentrated under reduced pressure, yielding 0.30 gram of 2,4-diamino-5-[3-(naphth-1-yl)propyl]pyrimidine, mp 179°–181° C. The NMR spectrum was consistent with the proposed structure.

EXAMPLE 2

SYNTHESIS OF 2,4-DIAMINO-5-(4-PHENYLBUTYL)PYRIMIDINE (COMPOUND 37)

Step A Synthesis of 1-methylsulfonyloxy-5-phenylpentane as an intermediate

A stirred solution of 25.0 grams (0.152 mole) of 5-phenylpentanol and 23.3 mL (0.167 mole) of triethylamine in 250 mL of methylene chloride was cooled to 0° C., and a solution of 13.0 mL (0.167 mole) of methanesulfonyl chloride in 50 mL of methylene chloride was added dropwise at a rate to maintain the reaction mixture temperature at 0° C. to 5° C. The complete addition required about 45 minutes. Upon completion of addition, the reaction mixture was allowed to warm to ambient temperature. After this time the reaction mixture was washed with two 200 mL portions of an aqueous 5% sodium bicarbonate solution and then with 200 mL of an aqueous solution saturated with sodium chloride. The organic layer was dried with magnesium sulfate and filtered. The filtrate was concentrated under reduced pressure, yielding 36.8 grams of 1-methylsulfonyloxy-5-phenylpentane. The NMR spectrum was consistent with the proposed structure.

Step B Synthesis of 6-phenylhexanenitrile as an intermediate

A stirred solution of 15.0 grams (0.0062 mole) of 1-methylsulfonyloxy-5-phenylpentane and 9.1 grams (0.190 mole) of sodium cyanide in 150 mL of N,N-dimethylformamide was heated at 50° C. to 55° C. for about 60 hours. After this time the reaction mixture was poured into 400 mL of water. The mixture was extracted with three 250 mL portions of diethyl ether. The combined extracts were then washed with three 200 mL portions of water and 200 mL of an aqueous solution saturated with sodium chloride. The organic layer was dried with magnesium sulfate and filtered. The filtrate was concentrated under reduced pressure, yielding 10.2 grams of 6-phenylhexanenitrile. The NMR spectrum was consistent with the proposed structure.

Step C Synthesis of 2-cyano-6-phenyl-1-hexen-1-ol as an intermediate

A stirred solution of 2.2 mL (0.01 6 mole) of diisopropylamine in 200 mL of tetrahydrofuran was cooled to −80° C., and 6.4 mL (0.016 mole) of n-butyllithium (2.5 Molar in hexanes) was added dropwise during a 15 minute period. Upon completion of addition, the reaction mixture was stirred for an additional 15 minutes. While still maintaining the reaction mixture temperature at −80° C. to −75° C., a solution of 2.5 grams (0.016 mole) of 6-phenylhexanenitrile in 50 mL of tetrahydrofuran was added dropwise during a 30 minute period. Upon completion of addition, the reaction mixture was stirred at −80° C. for an additional 30 minutes. After this time, a solution of 1.3 mL (0.016 mole) of ethyl formate in 50 mL of tetrahydrofuran was added dropwise during a ten minute period. Upon completion of addition, the reaction mixture was stirred for two hours at −80° C. to −70° C. The reaction was quenched with 100 mL of water, and the mixture was acidified with 6N hydrochloric acid. The mixture was extracted with two 150 mL portions of diethyl ether. The combined extracts were dried with magnesium sulfate and filtered. The filtrate was concentrated under reduced pressure to a residue. The residue was subjected to column chromatography using silica gel. Elution was accomplished using 1% to 3% methanol in methylene chloride. The appropriate fractions were combined and concentrated under reduced pressure, yielding 2.7 grams of 2-cyano-6-phenyl-1-hexen-1-ol. The NMR spectrum was consistent with the proposed structure.

Step D Synthesis of 1-methoxy-2-cyano-6-phenyl-1-hexene as an intermediate

A solution of 3.0 grams of potassium hydroxide in 6 mL of water was placed in a commercially available diazomethane generator. Ethanol, 8 mL, was added to the generator, and the contents of the generator were slowly warmed to 60° C. to 70° C. To this was added dropwise a solution of 4.6 grams (0.021 mole) of Diazald® in a minimum amount of diethyl ether. The diazomethane generated was condensed on a cold finger and, in turn, was allowed to drip into a stirred, cooled, solution of 2.5 grams (0.012 mole) of 2-cyano-6-phenyl-1-hexen-1-ol in a minimum of diethyl ether. The complete generation of diazomethane required about 30 to 45 minutes. Upon completion of the diazomethane generation, the reaction mixture was allowed to warm to ambient temperature. After this time the reaction mixture was concentrated under reduced pressure, yielding 2.4 grams of 1-methoxy-2-cyano-6-phenyl-1-hexene. The NMR spectrum was consistent with the proposed structure. Diazald® (N-methyl-N-nitroso-p-toluenesulfonamide) from Aldrich Chemical Company, Inc., Milwaukee, Wis.

Step E Synthesis of 2,4-diamino-5-(4-phenylbutyl) pyrimidine

A stirred solution of 2.4 grams (0.011 mole) of 1-methoxy-2- cyano-6-phenyl-1-hexene, 4.2 grams (0.044 mole) of guanidine hydrochloride, and 7.6 grams (0.055 mole) of potassium carbonate in 40 mL of N,N-dimethylformamide was heated at 100° C. to 105° C. for about 20 hours. After this time the reaction mixture was diluted with 100 mL of water. The mixture was then extracted with two 100 mL portions of ethyl acetate. The combined extracts were washed with three 75 mL portions of an aqueous 10% lithium chloride solution. The organic layer was dried with sodium sulfate and filtered. The filtrate was concentrated under reduced pressure to a residual oil. The residue was subjected to column chromatography on basic alumina that was deactivated to Level III with water. Elution was accomplished with 1% to 3% methanol in methylene chloride. The appropriate fractions were combined and concentrated under reduced pressure, yielding 1.4 grams of 2,4-diamino-5-(4-phenylbutyl)pyrimidine; mp 126°–127° C. The NMR spectrum was consistent with the proposed product.

EXAMPLE 3

SYNTHESIS OF 2,4-DIAMINO-5-[5-(NAPHTH-1-YL) PENTYL]PYRIMIDINE (Compound 54)

Step A Synthesis of 5-(naphth-1-yl)-4-pentyn-1-ol as an intermediate

Under a nitrogen atmosphere, a mixture of 4.0 mL (0.027 mole) of 1-iodonaphthalene, 0.1 gram (0.0003 mole) of copper(I)iodide, and 0.19 gram (0.0003 mole) of bis (triphenylphosphine)palladium(II) chloride in 75 mL of diethylamine was stirred, and 2.6 mL. (0.027 mole) of 4-pentyn-1-ol was added in one portion. Upon completion of addition, the reaction mixture was stirred at ambient temperature for about 18 hours. Gas chromatographic (GC) analysis of the reaction mixture indicated that the reaction had not gone to completion. An additional 0.5 mL of the 4-pentyn-1-ol was added, and the reaction mixture was stirred for an additional six hours. GC analysis of the reaction mixture indicated that the reaction was complete. The reaction mixture was passed through a column of silica gel. Elution was accomplished using methylene chloride. The eluate was concentrated under reduced pressure, yielding 3.9 grams of 5-(naphth-1-yl)-4-pentyn-1-ol. The NMR spectrum was consistent with the proposed structure.

Step B Synthesis of 5-(naphth-1-yl)pentanol as an intermediate

A mixture of 3.5 grams (0.017 mole) of 5-(naphth-1-yl) -4-pentyn-1-ol and 0.5 gram (catalyst) of 10% palladium on carbon in 30 mL of ethanol was shaken in a Parr hydrogenator until the theoretical amount of hydrogen gas was taken up. The reaction mixture was filtered to remove the catalyst, and the filtrate was concentrated under reduced pressure, yielding 3.4 grams of 5-(naphth-1-yl)pentanol. The NMR spectrum was consistent with the proposed structure.

Step C Synthesis of 1-methylsulfonyloxy-5-(naphth-1-yl) pentane as an intermediate This compound was prepared in a manner analogous to that of Example 2, Step A, using 3.1 grams (0.015 mole) of 5-(naphth-1-yl)pentanol, 2.1 mL (0.015 mole) of triethylamine, and 1.2 mL (0.015 mole) of methanesulfonyl chloride. The yield of 1-methylsulfonyloxy-5-(naphth-1-yl) pentane was 4.1 grams. The NMR spectrum was consistent with the proposed structure.

Step D Synthesis of 5-(naphth-1-yl)pentyl iodide as an intermediate

Under a nitrogen atmosphere, a stirred solution of 4.1 grams (0.014 mole) of 1-methylsulfonyloxy-5-(naphth-1-yl) pentane, and 4.2 grams (0.028 mole) of sodium iodide in 150 mL of acetone was heated at reflux for 2.5 hours. The reaction mixture was poured into 400 mL of water, and the mixture was extracted with two 100 mL portions of diethyl ether. The combined extracts were dried with magnesium sulfate and filtered. The filtrate was concentrated under reduced pressure, yielding 3.9 grams of 5-(naphth-1-yl) pentyl iodide. The NMR spectrum was consistent with the proposed structure.

Step E Synthesis of 1-ethoxy-2-cyano-7-(naphth-1-yl)-1-heptene as an intermediate This compound was prepared in a manner analogous to that of Example 1, Step B, using 3.9 grams (0.012 mole) of 5-(napth-1-yl)pentyl iodide, 1.4 mL (0.013 mole) of 3-ethoxyacrylonitrile and 5.3 mL (0.013 mole) of n-butyllithium (2.5M in hexanes)in 75 mL of tetrahydrofuran. The yield of 1-ethoxy-2-cyano-7-(naphth-1-yl)-1-heptene was 1.3 grams. The NMR spectrum was consistent with the proposed structure.

Step F Synthesis of 2,4-diamino-5-[5-(naphth-1-yl)pentyl] pyrimidine

This compound was prepared in a manner analogous to that of Example 2, Step E, using 1.3 grams (0.004 mole) of 1-ethoxy-2-cyano-7-(naphth-1-yl)-1-heptene, 1.7 grams (0.018 mole) of guanidine hydrochloride, and 3.6 grams (0.026 mole) of potassium carbonate in 25 mL of N,N-dimethylformamide. The yield of 2,4-diamino-5-[5-(naphth-1yl)pentyl]pyrimidine was 0.8 gram, mp 128°–133° C. The NMR spectrum was consistent with the proposed structure.

EXAMPLE 4

SYNTHESIS OF 2,4-DIAMINO-5-[3-(3-PHENYLPHENYL)PROPYL]-6-ETHYLPYRIMIDINE (Compound 33)

Step A Synthesis of ethyl 3-(3-bromophenyl)-2-propenoate as an intermediate

Under a nitrogen atmosphere, a stirred solution of 10.1 grams (0.045 mole) of 3-bromocinnamic acid and 40 drops of concentrated sulfuric acid in 75 mL of ethanol was heated at reflux for about 19 hours. After this time the reaction mixture was concentrated under reduced pressure to a residual oil. The oil was dissolved in methylene chloride, and the solution was washed with 50 mL of water and then with 50 mL of an aqueous solution saturated with sodium bicarbonate. The organic layer was dried with magnesium sulfate and filtered. The filtrate was concentrated under reduced pressure, yielding about 11.4 grams of ethyl 3-(3-bromophenyl)-2-propenoate. The NMR spectrum was consistent with the proposed structure.

Step B Synthesis of ethyl 3-(3-phenylphenyl)-2-propenoate as an intermediate

A stirred mixture of 11.0 grams (0.043 mole) of ethyl 3-(3-bromophenyl)-2-propenoate, 5.8 grams (0.047 mole) of phenylboronic acid, 0.25 gram (catalyst) of tetrakis-(triphenylphosphine)palladium(0), and 54.0 mL (0.110 mole) of a 2M solution of aqueous sodium carbonate in 100 mL of toluene was heated at reflux during a two hour period. After this time the reaction mixture was cooled, and the aqueous layer was separated. The toluene layer was washed with two 100 mL portions of water and then with 100 mL of an aqueous solution saturated with sodium chloride. The toluene layer was dried with magnesium sulfate and filtered. The filtrate was concentrated under reduced pressure, yielding 12.0 grams of ethyl 3-(3-phenylphenyl)-2-propenoate. The NMR spectrum was consistent with the proposed structure.

Step C Synthesis of ethyl 3-(3-phenylphenyl)propanoate as an intermediate

This compound was prepared in a manner analogous to that of Example 3, Step B, using 11.8 grams (0.047 mole) of ethyl 3-(3-phenylphenyl)-2-propenoate, hydrogen gas, 0.5 gram (catalyst) of 5% palladium on carbon, 25 mL of ethanol and 25 mL of ethyl acetate. The yield of ethyl 3-(3-phenylphenyl)propanoate was 10.8 grams. The NMR spectrum was consistent with the proposed structure.

Step D Synthesis of 3-oxo-5-(3-phenylphenyl)pentanenitrile as an intermediate

Under a nitrogen atmosphere, a stirred solution of 2.3 mL (0.044 mole) of acetonitrile in 50 mL of tetrahydrofuran was cooled to about –80° C., and 17.7 mL (0.044 mole) of n-butyllithium (2.5M in hexanes) was added dropwise at a rate to maintain the reaction mixture temperature below –75° C. Upon completion of addition, the reaction mixture was stirred at –78° C. for 30 minutes. After this time a solution of 10.3 grams (0.040 mole) of ethyl 3-(3-phenylphenyl)propanoate in 100 mL of tetrahydrofuran was added dropwise at a rate to maintain the reaction mixture temperature below –75° C. Upon completion of addition, the reaction mixture was stirred at –78° C. for one hour. After this time the reaction mixture was allowed to warm to ambient temperature, then was cooled to about 0° C., and 30 mL of aqueous 6N hydrochloric acid was added dropwise. Upon completion of addition, the reaction mixture was allowed to Warm to ambient temperature where it was stirred for 30 minutes. The mixture was poured into 200 mL of water, and then it was extracted with two 100 mL portions of diethyl ether. The combined extracts were dried with magnesium sulfate and filtered. The filtrate was concentrated under reduced pressure to a residual oil. NMR analysis of the residual oil indicated that it was impure. The oil was dissolved in 10:1 methylene chloride and acetone, and the solution was passed through a column of basic alumina that was deactivated to Level III with water. The eluate was concentrated under reduced pressure, yielding 5.9 grams of 3-oxo-5-(3-phenylphenyl)pentanenitrile. The NMR spectrum was consistent with the proposed structure.

Step E Synthesis of 3-hydroxy-5-(3-phenylphenyl)pentanenitrile as an intermediate Under a nitrogen atmosphere a stirred solution of 5.5 grams (0.022 mole) of 3-oxo-5-(3-phenylphenyl)pentanenitrile and 0.5 gram (0.013 mole) of sodium borohydride in 75 mL of tetrahydrofuran was heated at reflux for four hours. After this time the reaction mixture was allowed to cool to ambient temperature where it stood for about 16 hours. The reaction mixture was then poured into 300 mL of aqueous 1N hydrochloric acid. The mixture was extracted with two 150 mL portions of diethyl ether. The combined extracts were dried with magnesium sulfate and filtered. The filtrate was concentrated under reduced pressure to a residual oil. NMR analysis of the residual oil indicated that it was impure. The oil was dissolved in 20:1 methylene chloride and ethyl acetate, and the solution was passed through a column of silica gel. The eluate was concentrated under reduced pressure, yielding 3.8 grams of 3-hydroxy-5-(3-phenyl-phenyl)pentanenitrile. The NMR spectrum was consistent with the proposed structure.

Step F Synthesis of 3-methylsulfonyloxy-5-(3-phenylphenyl)pentanenitrile as an intermediate This compound was prepared in a manner analogous to that of Example 2, Step A, using 3.4 grams (0.014 mole) of 3-hydroxy-5-(3-phenylphenyl)pentanenitrile, 1.1 mL ((:) .014 mole) of methanesulfonyl chloride, and 1.9 mL (0.014 mole) of triethylamine in 100 mL of ethylene chloride. The yield of 3-methylsulfonyloxy-5-(3-phenylphenyl) pentanenitrile was 3.4 grams. The NMR spectrum was consistent with the proposed structure.

Step G Synthesis of 5-(3-phenylphenyl)pentanenitrile as an intermediate

A stirred mixture of 3.4 grams (0.010 mole) of 3-methylsulfonyloxy-5-(3-phenylphenyl)pentanenitrile, 3.4 grams (0.023 mole) of sodium iodide, 3.4 grams (0.052 mole) of zinc powder, and 3.4 mL of water in 50 mL of ethylene glycol dimethyl ether was heated at reflux for about 22 hours. The reaction mixture was cooled, and 150 mL of diethyl ether was added. The mixture was filtered, and the filtrate was washed in succession with water, an aqueous 5% hydrochloric acid solution, an aqueous 5% sodium bicarbonate solution, an aqueous 5% sodium bicarbonate solution, an aqueous 5% sodium thiosulfate solution, and finally with water. The organic layer was dried with magnesium sulfate and filtered. The filtrate was concentrated under reduced pressure to a residual oil. NMR analysis of the residual oil indicated that it was impure. The oil was dissolved in 10:1 petroleum ether and diethyl ether, and the solution was passed through a column of silica gel. Early fractions of eluate were combined and concentrated under reduced pressure, yielding an intermediate product, 5-(3-phenylphenyl)-2-pentenenitrile. Later fractions of the eluate were combined and concentrated under reduced pressure, yielding the intended product, 5-(3-phenylphenyl) pentanenitrile. The intermediate was hydrogenated in a manner analogous to that of Example 3, Step B, yielding an additional amount of 5-(3-phenylphenyl)pentanenitrile. All samples of the pentanenitrile were combined, yielding 1.4 grams of that product. The NMR spectrum was consistent with the proposed structure.

Step H Synthesis of 1-(3-phenylphenyl)-4-cyano-5-heptanone as an intermediate

This compound was prepared in a manner analogous to that of Step D, of this Example, using 1.4 grams (0.006 mole) of 5-(3-phenylphenyl)pentanenitrile, 0.8 mL (0.007 mole) of ethyl propanoate, and 2.8 mL (0.007 mole) of n-butyllithium (2.5M in hexanes)in 50 mL of tetrahydrofuran. The yield of 1-(3-phenylphenyl)-4-cyano-5-heptanone was 1.0 gram. The NMR spectrum was consistent with the proposed structure.

Step 1 Synthesis of 1-(3-phenylphenyl)-4-cyano-5-methoxy-4-heptene as an intermediate This compound was prepared in a manner analogous to that of Example 2, Step D, using 1.0 gram (0.004 mole) of 1-(3-phenylphenyl)-4-cyano-5-heptanone, 1.3 grams (0.006 mole) of Diazald, 3.5 grams (0.063 mole) of potassium hydroxide, 7 mL of water and 12 mL of ethanol. The yield of 1-(3-phenylphenyl)-4-cyano-4-methoxy-4-heptene was 1.0 gram. The NMR spectrum was consistent with the proposed structure.

Step J Synthesis of 2,4-diamino-5-[3-(3-phenylphenyl)propyl]-6-ethylpyrimidine

This compound was prepared in a manner analogous to that of Example 1, Step C, using 1.0 gram (0.003 mole) of 1-(3-phenylphenyl)-4-cyano-5-methoxy-4-heptene, 1.3 grams (0.01 3 mole) of guanidine hydrochloride, and 2.7 grams (0.020 mole) of potassium carbonate in 15 mL of N,N-dimethylformamide. The yield of 2,4-diamino-5-[3-(3-phenylphenyl)propyl]-6-ethylpyrimidine was 0.3 gram, mp 128°–133° C. The NMR spectrum was consistent with the proposed structure.

EXAMPLE 5

SYNTHESIS OF 2,4-DIAMINO.5-[3-(2,4,5,-TRICHLOROPHENYL)PROPYL]-6-ETHYLPYRIMIDINE (Compound 34)

Step A Synthesis of 4-(2,4,5-trichlorophenyl)-3-butyn-1-ol as an intermediate

This compound was prepared in a manner analogous to that of Example 3, Step A, using 10.0 grams (0.033 mole) of 2,4,5-trichloroiodobenzene, 2.5 mL (0.033 mole) of 3-butyn-1-ol, 0.23 gram (0.0003 mole) of bis(triphenylphosphine)palladium(II) chloride and 0.1 gram (0.0003 mole) of copper(II) iodide in 100 mL of diethylamine. The yield of 4-(2,4,5-trichlorophenyl)-3-butyn-1-ol was 7.3 grams. The NMR spectrum was consistent with the proposed structure.

Step B Synthesis of 4-(2,4,5-trichlorophenyl)butanol as an intermediate

This compound was prepared in a manner analogous to that of Example 3, Step B, using 7.0 grams (0.0030 mole) of 4-(2,4,5-trichlorophenyl)-3-butyn-1-ol, hydrogen gas, and 0.25 gram (catalyst) of 10% palladium on carbon in 50 mL of ethanol. The yield of 4-(2,4,5-trichlorophenyl)butanol was 7.0 grams. The NMR spectrum was consistent with the proposed structure.

Step C Synthesis of 1-methylsulfonyloxy-4-(2,4,5-trichlorophenyl)butane as an intermediate This compound was prepared in a manner analogous to that of Example 2, Step A, using 6.6 grams (0.026 mole) of 4-(2,4,5-trichlorophenyl)butanol, 2.0 mL (0.026 mole) of methanesulfonyl chloride, and 3.6 mL of triethylamine in 75 mL of methylene chloride. The yield of 1-methylsulfonyloxy-4-(2,4,5-trichlorophenyl)butane was 7.9 grams. The NMR spectrum was consistent with the proposed structure.

Step D Synthesis of 5-(2,4,5-trichlorophenyl)pentanenitrile as an intermediate

This compound was prepared in a manner analogous to that of Example 2, Step B, using 7.9 grams (0.024 mole) of 1-methylsulfonyloxy-4-(2,4,5-trichlorophenyl)butane and 3.5 grams (0.072 mole) of sodium cyanide in 50 mL of N,N-dimethylformamide. The yield of 5-(2,4,5-trichlorophenyl)pentanenitrile was 6.1 grams. The NMR spectrum was consistent with the proposed structure.

Step E Synthesis of 1-(2,4,5-trichlorophenyl)-4-cyano-5-heptanone as an intermediate This compound was prepared in a manner analogous to that of Example 4, Step D, using 5.8 grams (0.022 mole) of 5-(2,4,5-trichlorophenyl)pentanenitrile, 2.8 mL (0.024 mole) of ethyl propanoate, and 9.8 mL (0.024 mole) of n-butyllithium (2.5M in hexanes)in 100 mL of tetrahydrofuran. The yield of 1-(2,4,5-trichlorophenyl)-4-cyano-5-heptanone was 7.1 grams. The NMR spectrum was consistent with the proposed structure.

Step F Synthesis of 1-(2,4,5-trichlorophenyl)-4-cyano-5-methoxy-4-heptene as an intermediate This compound was prepared in a manner analogous to that of Example 2, Step D, using 7.1 grams (0.022 mole) of 1-(2,4,5-trichlorophenyl)-4-cyano-5-heptanone, 8.2 grams (0.037 mole) of Diazald, 10.0 grams (0.175 mole) of potassium hydroxide, 16 mL of water, and 20 mL of ethanol. The yield of 1-(2,4,5-trichlorophenyl)-4-cyano-5-methoxy-4-heptene was 7.2 grams. The NMR spectrum was consistent with the proposed structure.

Step G Synthesis of 2,4-diamino-5-[3-(2,4,5-trichlorophenyl)propyl]-6-ethylpyrimidine This compound was prepared in a manner analogous to that of Example 2, Step E, using 6.6 grams (0.020 mole) of 1-(2,4,5-trichlorophenyl)-4-cyano-5-methoxy-4-heptene, 7.6 grams (0.08 mole) of guanidine hydrochloride, and 16.6 grams (0.12 mole) of potassium carbonate in 50 mL of N,N-dimethylformamide. The yield of 2,4-diamino-5-[3-(2,4,5-trichlorophenyl)propyl]-6-ethylpyrimidine was 0.9 gram, mp 168°–182° C. The NMR spectrum was consistent with the proposed structure.

EXAMPLE 6

SYNTHESIS OF 2,4-DIAMINO-5-[3-(4-METHOXYPHENYL)PROPYL]PYRIMIDINE (Compound 32)

Step A Synthesis of 3-(4-methoxyphenyl)propyl iodide as an intermediate

Under a nitrogen atmosphere, a solution of 8.0 grams (0.048 mole) of 3-(4-methoxyphenyl)propanol and 7.9 grams (0.053 mole) of sodium iodide in 50 mL of acetone was stirred, and 5.7 mL (0.053 mole) of 1-chloroethyl chloroformate was slowly added. Upon completion of addition, the reaction mixture was heated to reflux where it was stirred for four hours. After this time the reaction mixture was cooled, and 50 mL of toluene was added. The acetone was removed by distillation after which the reaction mixture was heated for one hour at reflux in the toluene. The reaction mixture was then cooled and poured into 300 mL of water. The mixture was extracted with 200 mL of diethyl ether. The ether extract was washed with 100 mL of an aqueous 5% sodium thiosulfate solution and then with water. The organic layer was dried with magnesium sulfate and filtered. The filtrate was concentrated under reduced pressure to a residual oil, and the oil was dissolved in methylene chloride and filtered through a pad of silica gel. The filtrate was concentrated under reduced pressure to a residual oil. The oil was subjected to column chromatography on silica gel. Elution was accomplished with 40:1 petroleum ether and diethyl ether. The appropriate fractions were combined and concentrated under reduced pressure, yielding 4.3 grams of 3-(4-methoxyphenyl)propyl iodide. The NMR spectrum was consistent with tile proposed structure.

Step B Synthesis of 1-ethoxy-2-cyano-5-(4-methoxyphenyl)-1-pentene as an intermediate This compound was prepared in a manner analogous to that of Example 1, Step B, using 4.2 grams (0.015 mole) of 3-(4-methoxyphenyl) propyl iodide, 1.7 mL (0.017 mole) of 3-ethoxyacrylonitrile, and 6.7 mL of n-butyllithium (2.5M in hexanes) in 75 mL of tetrahydrofuran. The yield of 1-ethoxy-2-cyano-5-(4-methoxyphenyl)-1-pentene was 0.8 gram. The NMR spectrum was consistent with the proposed structure.

Step C Synthesis of 2,4-diamino-5-[3-(4-methoxyphenyl)-propyl]pyrimidine

This compound was prepared in a manner analogous to that of Example 2, Step E, using 0.8 gram (0.003 mole) of 1-ethoxy-2-cyano-5-(4-methoxyphenyl)-1-pentene, 1.3 grams (0.012 mole) of guanidine hydrochloride, and 2.7 grams (0.018 mole) of potassium carbonate in 15 mL of N,N-dimethylformamide. The yield of 1,4-diamino-5-[3-(4-methoxyphenyl)propyl]pyrimidine was 0.5 gram, mp 151°–154° C. The NMR spectrum was consistent with the proposed structure.

EXAMPLE 7

SYNTHESIS OF 2,4-DIAMINO-5-(5-PHENYLPENTYL)-6-(4-PHENYLBUTYL)PYRIMIDINE (Compound 43)

Step A Synthesis of ethyl 5-phenylpentanoate as an intermediate

This compound was prepared in a manner analogous to that of Example 4, Step A, using 19.9 grams (0.112 mole) of 5-phenylpentanoic acid and 15 drops of concentrated sulfuric acid in 150 mL of ethanol. The yield of ethyl 5-phenylpentanoate was 22.0 grams. The NMR spectrum was consistent with the proposed structure.

Step B Synthesis of 1,11-diphenyl-6-cyano-5-undecanone as an intermediate

This compound was prepared in a manner analogous to that of Example 2, Step C, using 8.4 grams (0.041 mole) ethyl 5-phenyl-pentanoate, 7.7 grams (0.041 mole) of 7-phenylheptanenitrile (prepared in a manner analogous to that of Example 2, Steps A and B), 5.8 mL (0.041 mole) of diisopropylamine, and 16.4 mL (0.041 mole) of n-butyllithium (2.5M in hexanes) in about 250 mL of tetrahydrofuran. The yield of 1,11-diphenyl-6-cyano-5-undecanone was 6.4 grams. The NMR spectrum was consistent with the proposed structure.

Step C Synthesis of 1,11-diphenyl-5-methoxy-6-cyano-5-undecene as an intermediate This compound was prepared in a manner analogous to that of Example 2, Step D, using 6.4 grams (0.018 mole) of 1,11-diphenyl-6-cyano-5-undecanone, 6.8 grams (0.032 mole) of Diazald, 7.5 grams (0.132 mole) of potassium hydroxide, 12 mL of water, and 16 mL of ethanol. The yield of 1,11-diphenyl-5-methoxy-6-cyano-5-undecene was 6.7 grams. The NMR spectrum was consistent with the proposed structure.

Step Synthesis of 2,4-diamino-5-(5-phenylpentyl)-6-(4-phenylbutyl)pyrimidine

This compound was prepared in a manner analogous to that of Example 2, Step E, using 6.4 grams (0.018 mole) of 1,11-diphenyl-5-methoxy-6-cyano-5-undecene, 6.7 grams (0.070 mole) of guanidine hydrochloride, and 12.1 grams (0.090 mole) of potassium carbonate in 50 mL of N,N-dimethylformamide. The yield of 2,4-diamino-5-(5-phenylpentyl)-6-(4-phenylbutyl)pyrimidine was 1.1 grams; mp 75°–78° C. The NMR spectrum was consistent with the proposed structure.

EXAMPLE 8

SYNTHESIS OF 2,4-DIAMINO-5-(3-PHENYLPHENYL-METHYL)PYRIMIDINE (Compound 22)

Method A Synthesis of 3-(3-phenylphenyl)propanenitrile as an intermediate

Step A Synthesis of 3-phenylphenylmethanol as an intermediate

This compound was prepared in a manner analogous to that of Example 4, Step B, using 10.0 grams (0.054 mole) of 3- bromophenyl-methanol, 7.2 grams (0.059 mole) of phenylboronic acid, 0.25 gram (catalyst) of tetrakis (triphenylphosphine)palladium(0), and 66 mL (0.135 mole) of aqueous 2M sodium carbonate in 50 mL of toluene. The crude product from this reaction was combined with a previous smaller run conducted on 4.6 grams (0.020 mole) of 3-bromophenylmethanol. The combination was subjected to column chromatography on silica gel. Elution was accomplished using 20:1 methylene chloride and ethyl acetate. The appropriate fractions were combined and concentrated under reduced pressure, yielding 12.9 grams of 3-phenylphenylmethanol. The NMR spectrum was consistent with the proposed structure.

Step B Synthesis of 3-phenylphenylmethyl bromide as an intermediate

Under a nitrogen atmosphere a stirred solution of 12.9 grams of 3-phenylphenylmethanol in 50 mL of 47–49% hydrobromic acid was heated at reflux for two hours. Thin layer chromatographic analysis of the reaction mixture indicated that the reaction was incomplete. An additional 50 mL of 47–49% hydrobromic acid was added, and the stirred reaction mixture was heated at reflux for an additional two hours. After this time the reaction mixture was poured into ice-water, and the mixture was extracted with 100 mL of diethyl ether. The extract was dried with magnesium sulfate and filtered. The filtrate was concentrated under reduced pressure, yielding 16.2 grams of 3-phenylphenylmethyl bromide. The NMR spectrum was consistent with the proposed structure.

Step C Synthesis of 3-(3-phenylphenyl)propane nitrile as an intermediate

This compound was prepared in a manner analogous to that of Example 4, Step D, using 6.0 grams (0.024 mole) of 3-phenylphenylmethyl bromide, 2.5 mL (0.048 mole) of acetonitrile, and 19.5 mL (0.048 mole) of n-butyllithium (2.5M in hexanes) in 75 mL of tetrahydrofuran. The yield of 3-(3-phenylphenyl)propanenitrile was 0.6 gram. The NMR spectrum was consistent with the proposed structure. The reaction was repeated in the manner of Method B, below.

Method B Synthesis of 3-(3-phenylphenyl)propanenitrile as an intermediate

Step A Synthesis of 3-phenylbenzaldehyde as an intermediate

This compound was prepared in a manner analogous to that of Example 4, Step B, using 7 mL (0.060 mole) of 3-bromobenzaldehyde, 8.1 grams (0.066 mole) of phenylboronic acid, 0.25 gram (catalyst) of tetrakis (triphenylphosphine)palladium(0), and 75 mL (0.150 mole) of aqueous 2M sodium carbonate in 50 mL of toluene. The yield of 3-phenylbenzaldehyde was 9.4 grams. The NMR spectrum was consistent with the proposed structure.

Step B Synthesis of 3-hydroxy-3-(3-phenylphenyl) propanenitrile as an intermediate This compound was prepared in a manner analogous to that of Example 4, Step D, using 9.4 grams (0.052 mole) of 3-phenylbenz-aldehyde, 3.0 mL (0.057 mole) of acetonitrile, and 22.7 mL (0.057 mole) of n-butyllithium (2.5M in hexanes) in 100 mL of tetrahydrofuran. The yield of 3-hydroxy-3-(3-phenylphenyl)propanenitrile was 10.7 grams. The NMR spectrum was consistent with the proposed structure.

Step C Synthesis of 3-(3-phenylphenyl)-2-propenenitrile as an intermediate

Under a nitrogen atmosphere a mixture of 1.9 grams (0.048 mole) of sodium hydride (60% in mineral oil) in 50 mL of tetrahydrofuran was stirred, and a solution of 10.7 grams (0.048 mole) of 3-hydroxy-3-(3-phenylphenyl) propanenitrile in 100 mL of tetrahydrofuran was added dropwise. Upon completion of addition, the reaction mixture was stirred until the evolution of hydrogen gas ceased. After this time the reaction mixture was cooled in an ice-bath, and 4.6 mL (0.048 mole) of acetic anhydride was added dropwise. Upon completion of addition, the reaction was allowed to warm to ambient temperature where it was stirred for about 18 hours. The reaction mixture was poured into 300 mL of water, and the mixture was extracted with 200 mL of diethyl ether. The extract was dried with magnesium sulfate and filtered. The filtrate was concentrated under reduced pressure to a residual oil. The oil was subjected to column chromatography on silica gel using methylene chloride as an eluant. The appropriate fractions were combined and concentrated under reduced pressure, yielding 4.0 grams of 3-(3-phenylphenyl)-2-propenenitrile. The NMR spectrum was consistent with the proposed structure.

Step D Synthesis of 3-(3-phenylphenyl)propanenitrile as an intermediate

This compound was prepared in a manner analogous to that of Example 3, Step B, using 4.0 grams (0.020 mole) of 3-(3-phenylphenyl)-2-propenenitrile, hydrogen gas, and 0.4 gram (catalyst) of 10% palladium on carbon in 30 mL of ethanol. The yield of 3-(3-phenyphenyl)propanenitrile was 3.2 grams. The NMR spectrum was consistent with the proposed structure.

The 0.6 gram from Method A was combined with the 3.2 grams from Method B, giving 3.8 grams of 3-(3-phenylphenyl)propanenitrile for use in the next reaction designated Step A.

Step A Synthesis of 1-(3-phenylphenyl)-2-cyano-3-pentanone as an intermediate

This compound was prepared in a manner analogous to that of Example 2, Step C, using 3.6 grams (0.017 mole) of 3-(3-phenylphenyl) propanenitrile, 2.0 mL (0.017 mole) of ethyl propanoate, 2.4 mL (0.017 mole) of diisopropylamine, and 6.9 mL (0.017 mole) of n-butyllithium (2.5M in hexanes) in 75 mL of tetrahydrofuran. The yield of 1-(3-phenylphenyl)-2-cyano-3-pentanone was 1.5 grams. The NMR spectrum was consistent with the proposed structure.

Step B Synthesis of 1-(3-phenylphenyl)-2-cyano-3-methoxy-2-pentene as an intermediate This compound was prepared in a manner analogous to that of Example 2, Step D, using 1.4 grams (0.005 mole) of 1-(3-phenylphenyl)-2-cyano-3-pentanone, 2.1 grams (0.010 mole) of Diazald, 2.5 grams (0.044 mole) of potassium hydroxide, 5 mL of water, and 8 mL of ethanol. The yield of 1-(3-phenylphenyl)-2-cyano-3-methoxy-2-pentene was 1.4 grams. The NMR spectrum was consistent with the proposed structure.

Step C Synthesis of 2,4-diamino-5-(3-phenylphenylmethyl) pyrimidine

This compound was prepared in a manner analogous to that of Example 2, Step E, using 1.4 grams (0.005 mole) of 1-(3-phenylphenyl)-2-cyano-3-methoxy-2-pentene, 2.0 grams (0.020 mole) of guanidine hydrochloride, and 4.2 grams (0.031 mole) of potassium carbonate in 15 mL of N,N-dimethylformamide. The yield of 2,4-diamino-5-(3-phenylphenylmethyl)pyrimidine was 0.6 gram; mp 108°–115° C. The NMR spectrum was consistent with the proposed structure.

EXAMPLE 9

SYNTHESIS OF 2-ETHYLAMINO-4-AMINO-5-[3-(NAPHTH-1-YL)PROPYL]PYRIMIDINE (Compound 50)

Step A Synthesis of ethyl 3-(naphth-1-yl)propanoate as an intermediate

A stirred solution of 50 grams (0.25 mole) of 3-(naphth-1-yl) propanoic acid and 20 drops (catalyst) of concentrated sulfuric acid in 250 mL of ethanol was heated at reflux for about 24 hours. After this time the reaction mixture was concentrated under reduced pressure to a residue. The residue was dissolved in diethyl ether, and the solution was washed with two 150 mL portions of an aqueous solution saturated with sodium bicarbonate and then with 150 mL of an aqueous solution saturated with sodium chloride. The organic layer was dried with magnesium sulfate and filtered. The filtrate was concentrated under reduced pressure, yielding 56.0 grams of ethyl 3-(naphth-1-yl)propanoate. The NMR spectrum was consistent with the proposed structure.

Step B Synthesis of 3-(naphth-1-yl)propanol as an intermediate

Under a nitrogen atmosphere, a mixture of 1.3 grams (0.033 mole) of lithium aluminum hydride in 40 mL of diethyl ether was stirred for one hour. The mixture was then cooled, and a solution of 10.0 grams (0.044 mole) of ethyl 3-(naphth-1-yl)propanoate in 35 mL of diethyl ether was added dropwise at a rate to keep the reaction mixture temperature below 25° C. Upon completion of addition, the reaction mixture was allowed to warm to ambient temperature where it was stirred for one hour. The reaction mixture was again cooled, and 50 mL of ethyl acetate was added to destroy excess lithium aluminum hydride. After this time 30 mL of an aqueous 10% sodium hydroxide solution was added dropwise. The reaction mixture was then acidified with aqueous 6N hydrochloric acid, and then it was poured into 300 mL of water. The organic layer was separated, dried with magnesium sulfate, and filtered. The filtrate was concentrated under reduced pressure, yielding 8.2 grams of 3-(naphth-1-yl)propanol. The NMR spectrum was consistent with the proposed structure.

Step C Synthesis of 1-methylsulfonyloxy-3-(naphth-1-yl) propane as an intermediate This compound was prepared in a manner analogous to that of Example 2, Step A, using 8.2 grams (0.044 mole) of 3-(naphth-1-yl)propanol, 3.4 grams (0.044 mole) of methanesulfonyl chloride, and 6.2 mL (0.044 mole) of triethylamine in 75 mL of methylene chloride. The yield of 1-methylsulfonyloxy-3-(naphth-1-yl)propane was 11.6 grams. The NMR spectrum was consistent with the proposed structure.

Step D Synthesis of 3-(naphth-1-yl)propyl iodide as an intermediate

An alternate preparation of this compound is shown in Example 1, Step A. In the present example, this compound was prepared in a manner analogous to that of Example 3, Step D, using 11.6 grams (0.044 mole) of 1-methylsulfonyloxy-3-(naphth-1-yl)propane, and 13.2 grams (0.088 mole) of sodium iodide in 250 mL of acetone. The yield of 3-(naphth-1-yl)propyl iodide was 12.1 grams. The NMR spectrum was consistent with the proposed structure.

Step E Synthesis of 1-ethoxy-2-cyano-5-(naphth-1-yl)-1-pentene as an intermediate This is the same compound as shown in Example 1, Step B. In the present example it was prepared in an analogous manner, using 12.1 grams (0.042 mole) of 3-(naphth-1-yl) propyl iodide, 48.0 mL (0.046 mole) of 3-ethoxyacrylonitrile, and 19.0 mL (0.046 mole) of n-butyllithium (2.5M in hexanes) in 200 mL of tetrahydrofuran. The yield of 1-ethoxy-2-cyano-5-(naphth-1-yl)-1-pentene was 5.3 grams. The NMR spectrum was consistent with the proposed structure.

Step F Synthesis of 2-ethylamino-4-amino-5-[3-(naphth-1-yl)propyl]pyrimidine

This compound was prepared in a manner analogous to that of Example 2, Step E, using 1.2 grams (0.005 mole) of 1-ethoxy-2-cyano-5-(naphth-1-yl)-1-pentene, 2.2 grams (0.020 mole) of 1-ethylguanidine hydrochloride and 3.7 grams (0.03 mole) of potassium carbonate in 12 mL of N,N-dimethylformamide. The yield of 2-ethylamino-4-amino-5-[3-(naphth-1yl)propyl]pyrimidine was 0.5 gram. The NMR spectrum was consistent with the proposed structure.

EXAMPLE 10

SYNTHESIS OF 2,4-DIAMINO-5-PHENYLPYRIMIDINE (Compound 15)

Step A Synthesis of 1-cyano-phenyl-2-(N,N-dimethylamino)ethene as an intermediate A stirred solution of 5.1 grams (0.044 mole) of benzyl cyanide and 8.7 grams (0.065 mole) of N,N-dimethylformamide dimethyl acetal in 150 mL of methanol was heated at reflux for about 20 hours. After this time gas chromatographic analysis of the reaction mixture indicated that the reaction was not complete. An additional 3.0 mL of the intermediate acetal (total—0.088 mole) was added, and the heating at reflux was continued an additional 24 hours. After this time the reaction mixture was concentrated under reduced pressure to a residue. The residue was triturated with 25% methylene chloride in petroleum ether, yielding 5.9 grams of 1-cyano-1-phenyl-2-(N,N-dimethylamino) ethene. The NMR spectrum was consistent with the proposed structure.

Step B Synthesis of 2,4-diamino-5-phenylpyrimidine

This compound was prepared in a manner analogous to that of Example 2, Step E, using 4.9 grams (0.031 mole) of 1-cyano-1-phenyl-2-(N,N-dimethylamino)ethene, 11.8 grams (0.124 mole) of guanidine hydrochloride, and 21.4 grams (0.1 56 mole) of potassium carbonate in N,N-dimethylformamide. The yield of 2,4.-diamino-5-phenylpyrimidine was 0.7 gram; mp 162°–164° C. The NMR spectrum was consistent with the proposed structure.

EXAMPLE 11

SYNTHESIS OF 2,4,6-TRIAMINO-5-[3-(NAPHTH-1-YL) PROPYL]PYRIMIDINE (Compound 48)

Step A Synthesis of 2-cyano-5-(naphth-1-yl)pentanenitrile as an intermediate

A solution of 0.7 gram (0.011 mole) of malononitrile in 50 mL of tetrahydrofuran was stirred, and 0.5 gram (0.011 mole) of sodium hydride (60% in mineral oil) was added portionwise during a ten minute period. Upon completion of addition, the reaction mixture was stirred for 30 minutes at ambient temperature. After this time a solution of 3.0 grams (0.010 mole) of 3-(naphth-1-yl)propyl iodide (prepared as in Example 9, Steps A–D) in about 5 mL of tetrahydrofuran was added in one portion. Upon completion of addition, the reaction mixture was stirred at ambient temperature for about 20 hours. The reaction mixture was acidified with aqueous 6N hydrochloric acid and then was further diluted with 100 mL of water. The mixture was extracted with two 100 mL portions of diethyl ether. The combined extracts were washed with an aqueous solution saturated with sodium chloride. The organic layer was dried with magnesium sulfate and filtered. The filtrate was concentrated to a residue which was subjected to column chromatography on silica gel. Elution was accomplished using 40% to 65% methylene chloride and petroleum ether. The appropriate fractions were combined and concentrated under reduced pressure, yielding 1.1 grams of 2-cyano-5-(naphth-1-yl) pentanenitrile. The NMR spectrum was consistent with the proposed structure.

Step B Synthesis of 2,4,6-triamino-5-[3-(naphth-1-yl) propyl]pyrimidine (Compound 48)

A solution of sodium ethoxide, prepared from 0.04 gram (0.002 mole) of sodium metal in 50 mL of ethanol, was stirred, and 0.2 gram (0.002 mole) of guanidine hydrochloride was added in one portion. The reaction mixture was stirred for 15 minutes and filtered to remove a precipitate. The filtrate was stirred, and 0.4 gram (0.002 mole) of 2-cyano-5-(naphth-1-yl)pentanenitrile was added in one portion. Upon completion of addition, the reaction mixture was heated at reflux for about 16 hours. After this time the reaction mixture was concentrated under reduced pressure to a residue. The residue was triturated with warm water, yielding, when dried, 0.4 gram of 2,4,6-triamino-5-[3-(naphth-1-yl)propyl]-pyrimidine, mp 181°–183° C., (dec.). The NMR spectrum was consistent with the proposed structure.

EXAMPLE 12

SYNTHESIS OF 2,4-DIAMINO-5-(2-ETHYLBUTOXY) PYRIMIDINE (Compound 56)

Step A Synthesis of 2,4-diaminopyrimidine as an intermediate

This compound was prepared in a manner analogous to that of Example 2, Step E, using 7.3 grams (0.075 mole) of 3-ethoxyacrylonitrile, 28.7 grams (0.300 mole) of guanidine hydrochloride and 55.3 grams (0.400 mole) of powdered potassium carbonate in 250 mL of N,N-dimethylformamide. The yield of 2,4-diaminopyrimidine was 7.0 grams; mp 146°–147° C. The NMR spectrum was consistent with the proposed structure. The reaction was repeated on a large scale.

Step B Synthesis of 2,4-diamino-5-pyrimidinyl hydrogen sulfate as an intermediate Under a nitrogen atmosphere, a stirred mixture of 53.7 grams (0.49 mole) of finely ground 2,4-diaminopyrimidine and 167.0 grams (0.73 mole) of ammonium persulfate was cooled to 18° C., and a solution of 144.0 grams of sodium hydroxide in 250 mL of water was added dropwise during a 3.5 hour period. Upon completion of addition, the reaction mixture was allowed to warm to ambient temperature as it stirred during about a 16 hour period. After this time the reaction mixture was cooled to 0° C., and 300 mL of 12N hydrochloric acid was added dropwise. Upon completion of addition, the reaction mixture was cooled to -5° C., and the resultant solid was collected by filtration. The solid was recrystallized from water, yielding 47.5 grams of 2,4-diamino-5-pyrimidinyl hydrogen sulfate. The NMR spectrum was consistent with the proposed structure.

Step C Synthesis of 2,4-diamino-5-hydroxypyrimidine hydrosulfate salt as an intermediate A stirred solution of 23.0 grams ((:).235 mole) of concentrated sulfuric acid and about 18 mL of water was heated to reflux, and 48.5 grams (0.235 mole) of 2,4-diamino-5-pyrimidinyl hydrogen sulfate was added in one portion. Upon completion of addition, the reaction mixture was heated at reflux for ten minutes and then was immediately cooled in an ice-water bath. The resultant solid was collected by filtration, and the filter cake was washed with 100 mL of cold water. The solid was dried, yielding 34.0 grams of 2,4-diamino-5-hydroxypyrimidine hydrosulfate salt, mp 290° C., dec. The NMR spectrum was consistent with the proposed structure.

Step D Synthesis of 2,4-diamino-5-(2-ethylbutoxy) pyrimidine

A stirred solution of 0.50 gram (0.003 mole) of 2,4-diamino-5-hydroxypyrimidine hydrosulfate salt, 0.47 gram (0.007 mole) of 1-bromo-2-ethylbutane and 0.95 gram (0.007 mole) of anhydrous potassium carbonate in 5 mL of N,N-dimethylformamide was heated at 84°–86° C. for about two hours. After this time the reaction mixture was allowed to cool to ambient temperature as it stirred during about a 16 hour period. The reaction mixture was then stirred with 50 mL of water and 50 mL of methylene chloride. The methylene chloride layer was separated and washed with 50 mL of water. The organic layer was dried with sodium sulfate and filtered. The filtrate was concentrated under reduced pressure to a solid residue. The residue was recrystallized from 2:1 water and methanol, yielding, when dried, 0.20 gram of 2,4-diamino-5-(2- ethylbutoxy)pyrimidine. The NMR spectrum was consistent with the proposed structure.

EXAMPLE 13

SYNTHESIS OF 2,4-DIAMINO-6-ETHYL-5-(4-CHLORO-3-UNDECYLAMINOPHENYL)PYRIMIDINE (Compound 74)

Step A Synthesis of 2,4-diamino-6-ethyl-5-( 4-chloro-3-nitrophenyl)pyrimidine as an intermediate (Compound 71)

Concentrated sulfuric acid, 90 mL, and 70% nitric acid, 90 mL, were stirred together during which time the mixture warmed to about 65° C. The mixture was allowed to cool to about 50° C., and 30.0 grams (0.12 mole) of 2,4-diamino-6-ethyl-5-(4-chlorophenyl)pyrimidine (commercially available) was added portionwise during a 45 minute period, while maintaining the reaction mixture temperature at about 50°–53° C. Upon completion of addition, the reaction mixture was stirred for one hour, while still maintaining the reaction mixture temperature at about 50° C. After this time, the reaction mixture was cooled and poured into ice. The resultant mixture was cooled further and, with stirring, was made basic with concentrated ammonium hydroxide. A precipitate was collected by filtration, rinsed with water and dried, yielding 35.4 grams of 2,4-diamino-6-ethyl-5-(4-chloro3-nitrophenyl)pyrimidine, mp 220°–223° C., dec. The NMR spectrum was consistent with the proposed structure.

Step B Synthesis of 2,4-diamino-6-ethyl-5-(3-amino-4-chlorophenyl)pyrimidine as an intermediate A heterogeneous mixture of 76.4 grams of stannous chloride dihydrate in 315 mL of aqueous 10M hydrochloric acid was stirred and cooled to about 5°–10° C. To this was added portionwise during a 15 minute period, 32.2 grams (0.11 mole) of 2,4-diamino-6-ethyl-5-(4-chloro-3-nitrophenyl)pyrimidine, while maintaining the reaction mixture temperature between about 5°–10° C. Upon completion of addition, the reaction mixture was allowed to warm to ambient temperature where it was stirred for about 16 hours. The resultant solid precipitate was collected by filtration, and stirred with 1500 mL of water. The solution was cooled in an ice bath, and the pH was adjusted to 12 with aqueous 20% sodium hydroxide. The resultant precipitate was collected by filtration and dried, yielding 26.2 grams of solid. The solid was dissolved in 350 mL of ethanol, and the solution was heated at reflux. The solution was filtered hot, and the filtrate was allowed to cool. The resultant solid was collected by filtration and dried, yielding 9.6 grams of product. The NMR spectrum was consistent with the proposed structure. The filtrate was concentrated under reduced pressure, and the residue was recrystallized from 125 ml of ethanol, yielding an additional 8.9 grams of product. The NMR spectrum was consistent with the proposed structure. The filtrate from the recrystallization was concentrated under reduced pressure, yielding another 2.3 grams of product. The NMR spectrum of this crop was also consistent with the proposed structure. The total yield of 2,4-diamino-6-ethyl-5-(3-amino-4-chlorophenyl)pyrimidine was 20.8 grams.

Step C Synthesis of undecanoyl chloride as an intermediate

Under a nitrogen atmosphere, a solution of 5.0 grams (0.027 mole) of undecanoic acid in 75 mL of methylene chloride was stirred and 2.8 ml (0.032 mole) of oxalyl chloride and 5 drops of N,N-dimethylformamide were added. Upon completion of addition, the reaction mixture was stirred for about 16 hours, then it was concentrated under reduced pressure, yielding 2.2 grams of undecanoyl chloride.

Step D Synthesis of 2,4-diamino-6-ethyl-5-(4-chloro-3-decylcarbonylaminophenyl)pyrimidine (Compound 85) for biological testing and as an intermediate Under a nitrogen atmosphere, a solution of 2.5 grams (0.001 mole) of 2,4-diamino-6-ethyl-5-(3-amino-4-chlorophenyl)pyrimidine (prepared in Step B of this Example) in 75 mL of pyridine and 25 mL of tetrahydrofuran was stirred and cooled in an ice bath. To this was added dropwise during a 10 minute period, a solution of 2.2 grams (0.001 mole) of undecanoyl chloride in 50 mL of tetrahydrofuran. The reaction mixture was maintained below about 10° C. throughout the addition. Upon completion of addition, the reaction mixture was stirred under a nitrogen atmosphere for about 4 days. After this time, the reaction mixture was taken up in 100 mL of water and poured into 500 mL of water. The mixture was then extracted with two 200 mL portions of ethyl acetate. The combined extracts were washed with 150 mL of aqueous 10% lithium chloride. The organic layer was dried with magnesium sulfate and filtered. The filtrate was concentrated under reduced pressure to a residue. In an effort to remove any excess pyridine, the residue was taken up in 50 mL of toluene, and the solution was concentrated under reduced pressure to a residue. This procedure was repeated two more times. The residue was subjected to column chromatography on silica gel. Elution was accomplished with 10:1 methylene chloride and methanol. The product-containing fractions were combined and concentrated under reduced pressure, yielding 2.8 grams of 2,4-diamino-6-ethyl-5-(4-chloro-3-decylcarbonylaminophenyl)pyrimidine. The NMR spectrum was consistent with the proposed structure.

Step E Synthesis of 2,4-diamino-6-ethyl-5-(4-chloro-3-undecylaminophenyl)pyrimidine Under a nitrogen atmosphere, a stirred solution of 40 mL of 1M boranetetrahydrofuran complex was cooled to below 10° C., and a solution of 2.4 grams (0.006 mole) of 2,4-diamino-6-ethyl-5-(4-chloro-3-decylcarbonylaminophenyl) pyrimidine in 60 mL of tetrahydrofuran was added dropwise during about a 5 minute period. The reaction mixture temperature was maintained below 10° C. throughout the addition. Upon completion of addition, the reaction mixture was heated at 60° C. for about 18 hours. After this time, the reaction mixture was allowed to cool to ambient temperature, where it was stirred for about 24 hours. The reaction mixture was then made acidic with aqueous 2N hydrochloric acid, after which time it was stirred for about 15 minutes. The mixture was made basic with aqueous 10% sodium hydroxide, and then it was extracted with two 150 mL portions of ethyl acetate. The combined extracts were dried with magnesium sulfate and filtered. The filtrate was concentrated under reduced pressure to a residue. The residue was subjected to column chromatography on silica gel. Elution was accomplished using 10:1 methylene chloride and methanol. The product-containing fractions were combined and concentrated under reduced pressure, yielding when dried, 0.7 gram of 2,4-diamino-6-ethyl-5-(4-chloro-3-undecylaminophenyl)pyrimidine. The NMR spectrum was consistent with the proposed structure.

EXAMPLE 14

SYNTHESIS OF 2,4-DIAMINO-6-ETHYL-5-(3-UNDECYLPHENOXY)PYRIMIDINE (Compound 100)

Step A Synthesis of 3-(phenylmethoxy)phenyl bromide as an intermediate

Under a nitrogen atmosphere, a solution of 50.0 grams (0.29 mole) of 3-bromophenol and 120.0 grams (0.87 mole) of potassium carbonate in 400 mL of N,N-dimethylformamide was stirred, and heated to 80° C. To this was added portionwise, 36.1 mL (0.30 mole) of phenylmethyl bromide during a 20 minute period. Upon completion of addition, the reaction mixture was stirred at 80° C. during a one hour period. After this time, the reaction mixture was allowed to cool to ambient temperature, where it was diluted with 600 mL of water. The mixture was extracted with 600 mL of diethyl ether. The extract was then washed with three 50 mL portions of water, and then it was concentrated under reduced pressure to a residual solid. The solid was recrystallized with 250 mL of methanol, yielding 68.3 grams of 3-(phenylmethoxy)phenyl bromide. The NMR spectrum was consistent with the proposed structure.

Step B Synthesis of 1-[3-(phenylmethoxy)phenyl]undecanol as an intermediate

Under a nitrogen atmosphere, a solution of 17.0 grams (0.065 mole) of 3-(phenylmethoxy)phenyl bromide in 125 mL of tetrahydrofuran was stirred and cooled to −70° C. To this was added dropwise 28.0 mL (0.071 mole) of 2.5M n-butyllithium (in hexanes) during a 15 minute period. The reaction mixture temperature was maintained below −60° C. during the addition. Upon completion of addition, a solution of 11.5 grams (0.068 mole) of undecanaldehyde in 15 mL of tetrahydrofuran was added dropwise during a 5 minute period. Upon completion of addition, the reaction mixture was allowed to warm to 0° C. during a one hour period. The reaction mixture was again cooled to −60° C., and 100 mL of water was added. The reaction mixture was allowed to warm to ambient temperature, and then it was extracted with 200 mL of diethyl ether. The ether extract was washed with 50 mL of water, and then it was concentrated under reduced pressure to a residue. The residue was subjected to column chromatography on silica gel. Elution was accomplished using 9:1 petroleum ether and diethyl ether, and 7:3 petroleum ether and diethyl ether. The product-containing fractions were combined and concentrated under reduced pressure, yielding 20.5 grams of 1-[3-(phenylmethoxy) phenyl]undecanol. The NMR spectrum was consistent with the proposed structure.

Step C Synthesis of 3-undecylphenol as an intermediate

A mixture of 3.0 grams (0.008 mole) of 1-(3-(phenylmethoxy) phenyl]undecanol and 0.5 gram (catalyst) of 10% palladium on charcoal and 50 mL of acetic acid in 50 mL of ethanol was hydrogenated using a Parr hydrogenator. Upon the uptake of the theoretical amount of hydrogen, the reaction mixture was filtered and concentrated under reduced pressure to a residual oil. NMR analysis of the oil indicated that the phenol portion of the molecule was completely unprotected, and the benzylic hydroxyl was about 70% removed. The oil was then mixed with 16.5 grams (0.047 mole) of 1-[3-(phenylmethoxy)phenyl] undecanol, 2.0 grams of 1.0% palladium on charcoal, 10 mL of water, and 50 mL of ethanol in 130 mL of acetic acid. The mixture was then hydrogenated as previously described, using the Parr hydrogenator. The reaction mixture was filtered and concentrated under reduced pressure to a residue. The residue was subjected to column chromatography on silica gel. Elution was accomplished using 9:1 petroleum ether and diethyl ether and 8:2 petroleum ether and diethyl ether. The product-containing fractions were combined and concentrated under reduced pressure, yielding 7.7 grams of 3-undecylphenol. The NMR spectrum was consistent with the proposed structure.

Step D Synthesis of ethyl 2-chloro-3-oxopentanoate as an intermediate

Ethyl 3-oxopentanoate, 20.0 grams (0.175 mole), was stirred at ambient temperature, and 23.6 grams (0.175 mole) of sulfuryl chloride was added dropwise during a 20 minute period. Upon completion of addition, the reaction mixture was stirred for about 16 hours. The reaction mixture was then distilled under reduced pressure, yielding 23.3 grams of ethyl 2-chloro-3-oxopentanoate; bp 100°–103° C. at 21 mm.

Step E Synthesis of ethyl 2-(3-undecylphenoxy)-3-oxopentanoate as an intermediate A mixture of 7.0 grams (0.028 mole) of 3-undecylphenol (prepared in Steps A–C of this Example).and 1.1 grams (0.028 mole) of 60% sodium hydride ( in mineral oil) in 100 mL of toluene was stirred for about 20 minutes, and 4.2 grams (0.028 mole) of ethyl 2-chloro-3-oxopentanoate (prepared in Step D of this example) was added dropwise during about a 12 minute period. Upon completion of addition, the reaction mixture was heated to reflux, where it was stirred for about 6.5 hours. After this time, the reaction mixture was allowed to cool to ambient temperature, where it stood for about 16 hours. The reaction mixture was then taken up in 50 mL of water and 5 mL of acetic acid. The mixture was washed with an additional 50 mL of water and then with 25 mL of an aqueous solution saturated with sodium chloride. The organic layer was dried with sodium sulfate and filtered. The filtrate was concentrated under reduced pressure, yielding 8.9 grams of ethyl 2-(3-undecylphenoxy)-3-oxopentanoate. The NMR spectrum was consistent with the proposed structure.

Step F Synthesis of 2-amino-6-ethyl-4-hydroxy-5-(3-undecylphenoxy)pyrimidine as an intermediate A stirred solution of 8.9 grams (0.028 mole) of ethyl 2-(3-undecylphenoxy)-3-oxopentanoate and 2.5 grams (0.028 mole) of guanidine carbonate in 30 mL of ethanol was heated at reflux for about 6 hours. The reaction mixture was then concentrated under reduced pressure to a residue. The residue was taken up in 50 mL of water and 5 mL of acetic acid, and the mixture was extracted with 50 mL of diethyl ether. The ether layer was extracted with 20 grams of aqueous 10% sodium hydroxide and then with 100 mL of water. The water extract was made acidic with acetic acid, and then it was extracted with 50 mL of diethyl ether. The ether extract was concentrated under reduced pressure to a residue. The residue was then taken up in 25 mL of heptane, and the mixture was again concentrated under reduced pressure to a residual solid. The solid was slurried in an additional 25 mL of heptane, and then it was collected by filtration. The solid was dried under reduced pressure, yielding 1.7 grams of 2-amino-6-ethyl-4-hydroxy-5-(3-undecylphenoxy) pyrimidine. The NMR spectrum was consistent with the proposed structure.

Step G Synthesis of 2-amino-4-chloro-6-ethyl-5-(3-undecylphenoxy) pyrimidine as an intermediate A stirred solution of 1.7 grams (0.004 mole) of 2-amino-6-ethyl-4-hydroxy-5-(3-undecylphenoxy)pyrimidine in 5 mL of phosphorus oxychloride was heated at reflux for about 1.5 hours. The reaction mixture was then poured into 50 grams of ice. The mixture was made basic with concentrated ammonium hydroxide. The liquid was then decanted from a tarry residue. The residue was washed with 50 ml of water, and the water was decanted from the residue. The residue, which was crude 2-amino-4-chloro-6-ethyl-5-(3-undecylphenoxy)pyrimidine, was used without further purification in the next reaction.

Step H Synthesis of 2,4-diamino-6-ethyl-5-(3-undecylphenoxy) pyrimidine

The tarry residue from Step G, which was 2-amino-4-chloro-6-ethyl-5-(3-undecylphenoxy)pyrimidine, was dissolved in 50 mL of ethanol and placed in a pressure bottle. The ethanol solution was cooled in an ice bath, and an excess amount of ammonia gas was bubbled in. The pressure bottle was sealed, and the reaction mixture was heated to about 126° C., where it was stirred for about 16 hours. After this time the reaction mixture was cooled and removed from the pressure bottle. The reaction mixture was concentrated under reduced pressure to a residue. The residue was taken up in 40 mL of water, 10 mL of aqueous 10% sodium hydroxide, and 50 mL of diethyl ether. The ether was removed under reduced pressure, and 40 mL of heptane was added. The heptane was also removed under reduced pressure, and 40 mL of ethyl acetate was added. The mixture was shaken, and the organic layer was removed. The organic layer was washed with 25 mL of a solution saturated with sodium chloride, and then it was dried with sodium sulfate. The mixture was filtered, and the filtrate was concentrated under reduced pressure to a residue. The residue was taken up in 15 mL of diethyl ether and cooled in dry ice. The resultant solid was collected by filtration and washed with cold diethyl ether. Upon washing the solid with cold ether, some of the solid dissolved into the filtrate. The remaining solid and 10 mL of heptane were combined with the filtrate. The combination was concentrated under reduced pressure to remove the diethyl ether. The mixture was then filtered to collect a solid. The solid was washed with heptane and dried, yielding 0.5 gram of 2,4-diamino-6-ethyl-5-(3-undecylphenoxy)pyrimidine; mp 97°–99° C. The NMR spectrum was consistent with the proposed structure.

EXAMPLE 15

SYNTHESIS OF 2,4-DIAMINO-5-[3-NITRO-4-[(3,4-DICHLOROPHENYL)METHYLAMINO]PHENYL]-6-ETHYLPYRIMIDINE (Compound 112)

Step A Synthesis of 2,4-diamino-5-(4-chloro-3-nitrophenyl)-6-ethylpyrimidine as an intermediate A stirred solution of 75 mL of 70% nitric acid and 75 mL of concentrated sulfuric acid warmed to about 50° C. from the heat of solution. To this was added 25 grams (0.10 mole) of 2,4-diamino-5-(4-chloro-phenyl)-6-ethylpyrimidine (commercially available) during a 10 minute period. Upon completion of addition, the reaction mixture was stirred at 50° C. for about 1 hour. After this time, the reaction mixture was allowed to cool to ambient temperature where it was stirred for about 18 hours. The reaction mixture was then poured into 1000 mL of ice containing 110 mL of concentrated ammonium hydroxide. The resultant solid was collected by filtration and recrystallized from aqueous ethanol, yielding 29.2 grams of 2,4-diamino-5-(4-chloro-3-nitrophenyl)-6-ethylpyrimidine. The NMR spectrum was consistent with the proposed structure.

Step B Synthesis of 2,4-diamino-5-[3-nitro-4-[(3,4-dichlorophenyl)methylamino]phenyl]-6-ethylpyrimidine (Compound 112)

A mixture of 2.0 grams (0.007 mole) of 2,4-diamino-5-(4-chloro-3-nitrophenyl)-6-ethylpyrimidine and 15 mL of 3,4-dichlorophenylethyl-amine was stirred at 100° C. for about 4 hours. After this time, the reaction mixture was poured into 250 mL of water. The water layer was decanted from an oily material, and the oily material was stirred with an additional 200 mL of water. The resultant solid was collected by filtration and dried, yielding 0.8 gram of 2,4-diamino-5-[3-nitro-4-[( 3,4-dichlorophenyl)methylamino]phenyl]-6-ethylpyrimidine, mp 244°–246° C. The NMR spectrum was consistent with the proposed structure.

EXAMPLE 16

SYNTHESIS OF THE HYDROCHLORIDE SALT OF 2,4-DIAMINO-5-[3-(2,4,5-TRICHLOROPHENYL)PROPYL]-6-ETHYLPYRIMIDINE (Compound 118)

Ethanol, 25 mL, was stirred and cooled in an ice bath and saturated with hydrogen chloride gas during a 15 minute period, while keeping the temperature of the reaction mixture below about 40° C. With continued stirring and cooling, a solution of 0.3 gram (0.0008 mole) of 2,4-diamino-5-[3-(2,4,5-trichlorophenyl)propyl]-6-ethylpyrimidine (Compound 34-prepared in Example 5) in 25 mL of ethanol was added dropwise during a 2 hour period. Upon completion of addition, the reaction mixture was allowed to warm to ambient temperature, where it was allowed to stir during a 19 hour period. After this time, the reaction mixture was concentrated under reduced pressure, yielding 0.3 gram of the hydrochloride salt of 2,4-diamino-5-[3-(2,4,5-trichlorophenyl)propyl]-6-ethylpyrimidine. The NMR spectrum was consistent with the proposed structure.

EXAMPLE 17

SYNTHESIS OF 2,4-DIAMINO-5-[3-(2-TRIFLUOROMETHYLPHENYL)PROPYL]-6-METHYLPYRIMIDINE (Compound 120)

Step A Synthesis of 5-(2-trifluoromethylphenyl)-4-pentynenitrile as an intermediate Under a nitrogen atmosphere, a solution of 15.0 grams (0.055 mole) of 2-trifluoromethylphenyl iodide, 4.8 grams (0.061 mole) of 4-pentynenitrile, 30.6 mL (0.22 mole) of triethylamine, 0.4 gram (0.0006 mole) of bis(triphenylphosphine)palladium(II) chloride, and 0.1 gram (0.0006 mole) of copper(II) iodide in 50 mL of acetonitrile was stirred at ambient temperature for 5 hours. After this time, gas chromatographic analysis (GC) of the reaction mixture indicated that the reaction was about 60% complete. The reaction mixture was warmed to 40°–45° C., where it was stirred for 16 hours. After this time the reaction mixture was poured into 300 mL of water, and the mixture was extracted with two 100 mL portions of diethyl ether. The combined extracts were washed with aqueous dilute hydrochloric acid and then were dried with magnesium sulfate. The mixture was filtered and concentrated under reduced pressure to a residual oil. The oil was subjected to column chromatography on silica gel. Elution was accomplished using 1:1 - methylene chloride and petroleum ether. The product-containing fractions were combined and concentrated under reduced pressure, yielding 11.4 grams of 5-(2-trifluoromethylphenyl)-4-pentynenitrile. The NMR spectrum was consistent with the proposed structure.

Step B Synthesis of 5-(2-trifluoromethylphenyl) pentanenitrile as an intermediate A sample of 11.1 grams (0.05 mole) of 5-(2-trifluoromethylphenyl)-4-pentynenitrile and 0.8 grams of 10% palladium on charcoal in 150 mL of ethanol was subjected to hydrogenation using a Parr hydrogenator. The reaction did not take up the theoretical amount of hydrogen gas. The reaction mixture was filtered to remove the catalyst, and the filtrate was concentrated to a residue. The residue was subjected to column chromatography on silica gel. Elution was accomplished using 2:1 petroleum ether and methylene chloride. The product-containing fractions were combined and concentrated under reduced pressure, yielding 8.7 grams of residue. The residue was hydrogenated as described above during a 3 hour period, using 0.3 gram of platinum oxide catalyst. The reaction mixture was filtered, and the filtrate was concentrated under reduced pressure to a residue. An NMR spectrum of the residue indicated that some starting material remained. The residue was again subjected to hydrogenation for 2 hours, using 0.3 gram of platinum oxide catalyst. After this time the reaction mixture was filtered, and the filtrate was concentrated under reduced pressure to a residue. The residue was subjected to column chromatography as previously described. The product-containing fractions were combined and concentrated under reduced pressure, yielding 6.8 grams of 5-(2-trifluoromethylphenyl)pentanenitrile. The NMR spectrum was consistent with the proposed structure.

Step C Synthesis of 3-cyano-6-(2-trifluoromethylphenyl)-2-hexanone as an intermediate This compound was prepared in a manner analogous to that of Step D of Example 4, using 6.5 grams (0.029 mole) of 5-(2-trifluoromethylphenyl)pentanenitrile, 4.2 mL (0.044 mole) of ethyl acetate, and 12.6 mL (0.032 mole) of n-butyllithium (2.5M in hexanes) in 75 mL of tetrahydrofuran. The yield of 3-cyano-6-(2-trifluoromethylphenyl)-2-hexanone was 7.6 grams. The NMR spectrum was consistent with the proposed structure.

Step D Synthesis of 3-cyano-2-methoxy-6-(2-trifluoromethylphenyl)-2-hexene as an intermediate This compound was prepared in a manner analogous to that of Step D of Example 2, using 7.6 grams (0.028 mole) of 3-cyano-6-(2-trifluoromethylphenyl)-2-hexanone, 10.3 grams (0.048 mole) of Diazald, 7.0 grams (0.125 mole) of potassium hydroxide, 12 mL of water, and 16 mL of ethanol. The yield of 3-cyano-2-methoxy-6-(2-trifluoromethylphenyl)-2-hexene was 7.6 grams. The NMR spectrum was consistent with the proposed structure.

Step E Synthesis of 2,4-diamino.-5-[3-(2-trifluoromethylphenyl)propyl]-6-methylpyrimidine (Compound 120)

Under a nitrogen atmosphere, a stirred solution of 7.6 grams (0.027 mole) of 3-cyano-2-methoxy-6-(2-trifluoromethylphenyl)-2-hexene and 12.2 grams (0.068 mole) of guanidine carbonate in 35 mL of N,N-dimethylacetamide was heated at about 150° C. for 40 hours. After this time, the reaction mixture was poured into 300 mL of water. The resultant solid was collected by filtration, and was then slurried in 100 mL of diethyl ether. The solid was again collected by filtration and was subjected to column chromatography on silica gel. Elution was accomplished using 10% methanol in methylene chloride. The product-containing fractions were combined and concentrated under reduced pressure, yielding 3.4 grams of 2,4-diamino-5-[3-(2-trifluoromethylphenyl)propyl]-6-methyl-pyrimidine, mp 151°–158° C. The NMR spectrum was consistent with the proposed structure.

EXAMPLE 18

SYNTHESIS OF 2,4-DIAMINO-5-[3-(2-TRIFLUOROMETHYLPHENOXY)PROPOXY]-6-METHYLPYRIMIDINE (Compound 135)

Step A Synthesis of 2,4-diamino-6-methylpyrimidine as an intermediate

A mixture of 50.0 grams (0.348 mole) of 2-amino-4-chloro-6-methylpyrimidine (commercially available) and 100 mL of aqueous 30% ammonia in 400 mL of methanol was placed in a high pressure vessel and heated to 130°–165° C. under a pressure of 140–250 psig, where it was stirred for 13 hours. After this time, the reaction mixture was allowed to cool to ambient temperature. The reaction vessel was then opened and the reaction mixture was removed. The reaction vessel was washed with 200 mL of methanol, and the wash was combined with the reaction mixture. The combination was concentrated under reduced pressure to a residual solid. The solid was then stirred for 2 hours at ambient temperature with 100 mL of aqueous 30% ammonia. The mixture was cooled to 0° C., and the solid was collected by filtration. The solid was dried, yielding 40.8 grams of 2,4-diamino-6-methylpyrimidine. The NMR spectrum was consistent with the proposed structure.

Step B Synthesis of 2,4-diamino-6-methyl-5-pyrimidinyl hydrogen sulfate as an intermediate This compound was prepared in a manner analogous to that of Step C of Example 12, using 30.0 grams (0.242 mole) of 2,4-diamino-6-methylpyrimidine, 82.8 grams (0.363 mole) of ammonium persulfate and 360 mL of aqueous 5N sodium hydroxide. The product was recrystallized from water, yielding 27.3 grams of 2,4-diamino-6-methyl-5-pyrimidinyl hydrogen sulfate, mp 285° C., dec. The IR spectrum was consistent with the proposed structure.

Step C Synthesis of 2,4-diamino-5-hydroxy-6-methylpyrimidine hydrosulfate salt as an intermediate This compound was prepared in a manner analogous to that of Step C of Example 12, using 26.7 grams (0.121 mole)

of 2,4-diamino-6-methyl-5-pyrimidinyl hydrogen sulfate and 12.3 grams (0.125 mole) of concentrated sulfuric acid in 50 mL of water. The yield of 2,4-diamino-5-hydroxy-6-methylpyrimidine hydrosulfate salt was 27.0 grams, mp 270° C., dec.. The NMR spectrum was consistent with the proposed structure.

Step D Synthesis of 2-trifluoromethylphenyl 3-bromopropyl ether as an intermediate Under a nitrogen atmosphere, a stirred mixture of 4.0 grams (0.025 mole) of 2-trifluoromethylphenol, 17.8 mL (0.178 mole) of 1,3-dibromopropane, and 9.0 grams (0.065 mole) of potassium carbonate in 120 mL of acetone was heated at reflux for about 18 hours. After this time, the reaction mixture was concentrated under reduced pressure to a residual oil. The oil was subjected to column chromatography on silica gel. Elution was accomplished using petroleum ether. The product containing fractions were combined and concentrated under reduced pressure, yielding 5.9 grams of 2-trifluoromethylphenyl 3-bromopropyl ether. The NMR spectrum was consistent with the proposed structure.

Step E Synthesis of 2,4-diamino-5-[3-(2-trifluoromethylphenoxy)-propoxy]-6-methylpyrimidine (Compound 135)

This compound was prepared in a manner analogous to that of Step D of Example 12, using 2.4 grams (0.010 mole) of 2,4-diamino-5-hydroxy-6-methylpyrimidine hydrosulfate salt (prepared in Steps A–C of this Example), 3.0 grams (0.011 mole) of 2-trifluoromethylphenyl 3-bromopropyl ether, and 8.3 grams (0.060 mole) of finely ground potassium carbonate in 50 mL of N,N-dimethylformamide. The product was recrystallized from methanol and water, yielding 0.8 gram of 2,4-diamino-5-[3-(2-trifluoromethylphenoxy)propoxy]-6-methylpyrimidine, mp 132°–134° C. The NMR spectrum was consistent with the proposed structure.

EXAMPLE 19

SYNTHESIS OF 2,4-DIAMINO-5-(ADAMANT-1-YL)-6-METHYLPYRIMIDINE (Compound110)

Step A Synthesis of ethyl 2-(adamant-1-yl)-3-oxobutanoate as an intermediate

A stirred solution of 5.0 grams (0.033 mole) of adamantan-1-ol and 4.7 grams (0.036 mole) of ethyl acetoacetate in 60 mL of pentane was cooled to 7° C., and 5.1 grams (0.036 mole) of boron trifluoride etherate was added during a 2 minute period. An additional 3.8 mL of boron trifluoride etherate was then added, also during a 2 minute period. Upon completion of addition, the reaction mixture was allowed to warm to ambient temperature, where it was stirred for about 16 hours. After this time, the reaction mixture was again cooled to 7° C., and 24 grams of aqueous 50% potassium hydroxide was added. The reaction mixture was then made acidic with 12 mL of acetic acid. The reaction mixture was poured into a separatory funnel with 50 mL of water and 130 mL of diethyl ether. The mixture was shaken and the layers were separated. The water layer was washed with two portions of 30 mL each of toluene. The toluene washes were combined with the diethyl ether layer, and 100 mL of water was added to the combination. The mixture was filtered and the layers were separated. The organic layer was dried with sodium sulfate and filtered. The filtrate was concentrated under reduced pressure, yielding 6.4 grams of ethyl 2-(adamant-1-yl)-3-oxobutanoate. The NMR spectrum was consistent with the proposed structure.

Step B Synthesis of 2-amino-4-hydroxy-5-( adamant- 1 -yl)-6-methylpyrimidine as an intermediate A stirred mixture of 5.4 grams (0.02 mole) of ethyl 2-(adamant-1-yl)-3-oxobutanoate, 2.0 grams (0.02 mole) of guanidine hydrochloride and sodium ethoxide [prepared by adding 1.6 grams (0.04 mole) of 60% sodium hydride (in mineral oil) to 30 mL of ethanol]in 67.5 mL of ethanol was heated at reflux for about 20 hours. After this time, the reaction mixture was concentrated under reduced pressure to a residue. The residue was taken up in 50 mL of water and 5 mL of acetic acid. The mixture was filtered, and the filter cake was washed with two 50 mL portions of water. The filter cake was triturated in hot ethanol, and the mixture was allowed to cool. A solid was collected by filtration, yielding when dried, 2.6 grams of 2-amino-4-hydroxy-5-(adamant-1-yl)-6-methyl-pyrimidine, mp 280°–287° C. The NMR spectrum was consistent with the proposed structure.

Step C Synthesis of 2-amino-4-chloro-5-(adamant-1-yl)-6-methylpyrimidine hydrochloride as an intermediate A stirred solution of 2.4 grams (0.009 mole) of 2-amino-4-hydroxy-5-(adamant-1-yl)-6-methylpyrimidine and 2.4 grams (0.012 mole) of phosphorus pentachloride in 24 mL of phosphorus oxychloride was heated at reflux for about 90 minutes. After this time, the reaction mixture was poured into 600 mL of ice. The resultant solid was collected by filtration and washed with water, yielding, when dried, about 1.8 grams of 2-amino-4-chloro 5-(adamant-1-yl)-6-methylpyrimidine hydrochloride. The NMR spectrum was consistent with the proposed structure.

Step D Synthesis of 2,4-diamino-5-(adamant-1-yl)-6-methylpyrimidine (Compound 110)

This compound was prepared in a manner analogous to that of Step H of Example 12, using 0.92 gram (0.003 mole) of 2-amino-4-chloro-5-(adamant-1-yl)-6-methylpyrimidine hydrochloride and 50 mL of aqueous 30% ammonium hydroxide. The yield of 2,4-diamino-5-(adamant-1-yl)-6-methylpyrimidine was 0.13 gram, mp 254°–258° C. The NMR spectrum was consistent with the proposed structure.

EXAMPLE 20

SYNTHESIS OF 2,4-DIAMINO-5-[4-(2,4,5-TRICHLOROPHENYL)BUTYL]-6-ETHYLPYRIMIDINE (Compound 38)

This compound was prepared in a manner analogous to that of Example 5, using 7.0 grams (0.020 mole) of 1-(2,4,5-trichlorophenyl)-5-cyano-6-methoxy-5-octene, 7.7 grams (0.080 mole) of guanidine hydrochloride, and 11.0 grams (0.080 mole) of potassium carbonate in 40 mL of N,N-dimethylformamide. The yield of 2,4-diamino-5-[4-(2,4,5-trichlorophenyl)butyl]-6-ethylpyrimidine was 1.5 grams, mp 158°–163° C. The NMR spectrum was consistent with the proposed structure.

EXAMPLE 21

SYNTHESIS OF 2,4-DIAMINO-5-(2-ETHYLBUTOXY) PYRIMIDINE (Compound 56)

The compound of this example was prepared in a manner analogous to that of Example 12, using 0.50 gram (0.003 mole) of 2,4-diamino-5-hydroxypyrimidine hydrosulfate salt, 0.47 gram (0.007 mole) of 1-bromo-2-ethylbutane, and 0.95 gram (0.007 mole) of anhydrous potassium carbonate in 5 mL of N,N-dimethylformamide. The yield of 2,4-diamino-5-(2-ethylbutoxy)pyrimidine was 0.21 gram, mp 173°–174° C. The NMR spectrum was consistent with the proposed structure.

EXAMPLE 22

SYNTHESIS OF 2,4-DIAMINO-5-[4-(4-CHLOROPHENYL)BUTYL]PYRIMIDINE (Compound 67)

This compound was prepared in a manner analogous to that of Example 3, using 2.7 grams (0.010 mole) of 1-ethoxy-2-cyano-6-(4-chlorophenyl)-1-hexene, 3.9 grams (0.041 mole) of guanidine hydrochloride, and 5.7 grams (0.041 mole) of anhydrous potassium carbonate in 5 mL of N,N-dimethylformamide. The yield of 2,4-diamino-5-[4-(4chlorophenyl)butyl]pyrimidine was 0.9 gram, mp 159°–162° C. The NMR spectrum was consistent with the proposed structure.

EXAMPLE 23

SYNTHESIS OF 2,4-DIAMINO-5-[3-(2,4,5-TRICHLOROPHENYL)PROPYL]-6-METHYLPYRIMIDINE (Compound 117)

This compound was prepared in a manner analogous to that of Example 5, using 2.7 grams (0.008 mole) of 1-(2,4,5-trichlorophenyl)-4-cyano-5-methoxy-4-hexene, 2.1 grams (0.022 mole) of guanidine hydrochloride, and 3.0 grams (0.022 mole) of anhydrous potassium carbonate in 40 mL of N,N-dimethylformamide. The yield of 2,4-diamino-5-[3-(2,4,5-trichlorophenyl)propyl]-6-methylpyrimidine was 0.5 gram, mp 215°–218° C. The NMR spectrum was consistent with the proposed structure.

EXAMPLE 24

SYNTHESIS OF 2,4-DIAMINO-5-[3-(2-METHYLPHENYL)PROPYL]-6-METHYLPYRIMIDINE (Compound 123)

This compound was prepared in a manner analogous to that of Steps A–F of Example 5, and Step E of Example 17, using 3.2 grams (0.014 mole) of 1-(2-methylphenyl)-4-cyano-5-methoxy-4-hexene, and 6.3 grams (0.035 mole) of guanidine carbonate in 75 mL of N,N-dimethylacetamide. The yield of 2,4-diamino-5-[3-(2-methylphenyl)propyl]-6-methylpyrimidine was 0.5 gram, mp 213°–215° C. The NMR spectrum was consistent with the proposed structure.

EXAMPLE 25

SYNTHESIS OF 2,4-DIAMINO-5-[3-(4-METHYLPHENYL)PROPYL]-6-METHYLPYRIMIDINE (Compound 125)

This compound was prepared in a manner analogous to that of Steps A–F of Example 5, and Step E of Example 17, using 1.4 grams (0.006 mole) of 1-(4-methylphenyl)-4-cyano-5-methoxy-4-hexene, and 2.7 grams (0.015 mole) of guanidine carbonate in 20 mL of N,N-dimethylacetamide. The yield of 2,4-diamino-5-[3-(4-methylphenyl)propyl]-6-methylpyrimidine was 0.1 gram, mp 210°–213° C. The NMR spectrum was consistent with the proposed structure.

EXAMPLE 26

SYNTHESIS OF 2,4-DIAMINO-5-[3-(2,4,5-TRIMETHYLPHENYL)PROPYL]-6-METHYLPYRIMIDINE (Compound 128)

This compound was prepared in a manner analogous to that of Steps A–F of Example 5, and Step E of Example 17, using 4.4 grams (0.017 mole) of 1-(2,4,5-trimethylphenyl)-4-cyano-5-methoxy-4-hexene, and 7.1 grams (0.042 mole) of guanidine carbonate in 25 mL of N,N-dimethylformamide. The yield of 2,4-diamino-5-[3-(2,4,5-trimethyl-phenyl)propyl]-6-methylpyrimidine was 2.9 grams, mp 188°–190° C. The NMR spectrum was consistent with the proposed structure.

EXAMPLE 27

SYNTHESIS OF 2,4-DIAMINO-5-(2-ETHYLBUTOXY)-6METHYLPYRIMIDINE (Compound 132)

This compound was prepared in a manner analogous to that of Examples 12 and 18, using 2.4 grams (0.01 0 mole) of 2,4-diamino-6-methyl-5-hydroxypyrimidine hydrosulfate salt, 2.8 mL (0.020 mole) of 1-bromo-2-ethylbutane, and 8.3 grams (0.060 mole) of anhydrous potassium carbonate in 5 mL of N,N-dimethylformamide. The yield of 2,4-diamino-5-(2-ethylbutoxy)-6-methylpyrimidine was 0.6 gram, mp 142°–143° C. The NMR spectrum was consistent with the proposed structure.

EXAMPLE 28

SYNTHESIS OF 2,4-DIAMINO-5-(3-PHENYLPROPOXY)-6-METHYLPYRIMIDINE (Compound 134)

This compound was prepared in a manner analogous to that of Examples 12 and 18, using 2.1 grams (0.009 mole) of 2,4-diamino-5-hydroxy-6-methylpyrimidine hydrosulfate salt, 2.7 mL (0.018 mole) of 3-phenylpropyl bromide, and 7.6 grams (0.055 mole) of anhydrous potassium carbonate in 40 mL of N,N-dimethylformamide. The yield of 2,4-diamino-5-(3-phenylpropoxy)-6-methylpyrimidine was 0.7 gram, mp 160.5°–161.5° C. The NMR spectrum was consistent with the proposed structure.

EXAMPLE 29

SYNTHESIS OF 2,4-DIAMINO-5-[3-(3-TRIFLUOROMETHYLPHENYL)BUTYL]-6-ETHYLPYRIMIDINE (Compound 137)

Step A Synthesis of 5-hydroxy-5-(3-trifluoromethylphenyl) hexanenitrile as an intermediate A mixture of 7.0 mL (0.05 mole) of 3-trifluoromethylphenyl bromide, 1.2 grams (0.05 mole) of magnesium and a crystal of iodine in about 70 mL of tetrahydrofuran was warmed to 35° C. to initiate the formation of the Grignard reagent. Upon formation of the Grignard reagent, the reaction mixture was cooled to ambient temperature and, with stirring, a solution of 5.8 mL (0.05 mole) of 5-oxohexanenitrile j:n 10 mL of tetrahydrofuran was added dropwise. The reaction mixture temperature increased to about 35° C., at which time the rate of addition was slowed to keep the reaction mixture temperature at about 35°–40° C. The complete addition required about 15 minutes. Upon completion of the addition, the reaction mixture was allowed to warm to ambient temperature, where it was stirred for 2 hours. After this time, the reaction mixture was poured into 200 mL of water and was acidified with aqueous 2N hydrochloric acid. The mixture was then extracted with two 150 mL portions of diethyl ether. The combined extracts were dried with magnesium sulfate and filtered. The filtrate was concentrated under reduced pressure to a residual oil. The oil was subjected to column chromatography on silica gel. Elution was accomplished using methylene chloride. The product-containing fractions were combined and concentrated under reduced pressure, yielding 6.3 grams of 5-hydroxy-5-(3-trifluoromethylphenyl)hexanenitrile. The NMR spectrum was consistent with the proposed structure.

Step B Synthesis of 5-(3-trifluoromethylphenyl) hexanenitrile as an intermediate Under a nitrogen atmosphere, a solution of 4.4 grams (0.017 mole) of 5-hydroxy-5-(3-trifluoromethylphenyl) hexanenitrile, 13 mL (0.102 mole) of chlorotrimethylsilane, 15.4 grams (0.102 mole) of sodium iodide, and 8.0 mL (0.153 mole) of acetonitrile in 30 mL of hexane was stirred for about 30 minutes. After this time, gas chromatographic analysis of the reaction mixture indicated that the reaction was complete. The reaction mixture was then stirred with 100 mL of water, and then it was extracted with 100 mL of diethyl ether. The combined extracts were dried with magnesium sulfate and filtered. The filtrate was concentrated under reduced pressure to a residue. The residue was subjected to column chromatography on silica gel. Elution was accomplished using methylene chloride. The methylene chloride eluate was dried with magnesium sulfate and filtered. The filtrate was concentrated under reduced pressure, yielding 1.9 grams of 5-(3-trifluoromethylphenyl) hexanenitrile. The NMR spectrum was consistent with the proposed structure.

Step C Synthesis of 4-cyano-7-(3-trifluoromethylphenyl)-3-octanone as an intermediate This compound was prepared in a manner analogous to that of Step E of Example 4, using 1.9 grams (0.008 mole) of 5-(3-trifluoromethylphenyl)hexanenitrile, 1.0 mL (0.009 mole) of ethyl propionate, and 3.6 mL (0.009 mole) of n-butyllithium (2.5M in hexanes) in 75 mL of tetrahydrofuran. The yield of 4-cyano-7-(3-trifluoromethylphenyl)-3-octanone was about 2.1 grams. The NMR spectrum was consistent with the proposed structure.

Step D Synthesis of 4-cyano-3-methoxy-7-(3-trifluoromethylphenyl)-3-octene as an intermediate This compound was prepared in a manner analogous to that of Step E of Example 2, using 2.1 grams (0.007 mole) of 4-cyano-7-(3-trifluoromethyphenyl)-3-octanone, 2.6 grams (0.012 mole) of Diazald, 4.0 grams of potassium hydroxide, and 7.0 mL of water in 12 mL of ethanol. The yield of -cyano-3-methoxy-7-(3-trifluoromethylphenyl)-3-octene was 2.1 grams. The NMR spectrum was consistent with the proposed structure.

Step E Synthesis of 2,4-diamino-5-[3-(3-trifluoromethylphenyl)butyl]-6-ethylpyrimidine (Compound 137)

This compound was prepared in a manner analogous to that of Step E of Example 17, using 2.1 grams (0.007 mole) of 4-cyano-3-methoxy-7-(3-trifluoromethylphenyl)-3-octene, and 3.1 grams (0.018 mole) of guanidine carbonate in 25 mL of N,N-dimethylacetamide. The yield of 2,4-diamino-5-[3-(3-trifluoromethylphenyl)butyl]-6-ethylpyrimidine was 0.7 gram, mp 93°–96° C. The NMR spectrum was consistent with the proposed structure.

EXAMPLE 30

SYNTHESIS OF 2,4-DIAMINO-5-[3-(4-TRIFLUOROMETHYLPHENYL)BUTYL]-6-ETHYLPYRIMIDINE (Compound 138)

This compound was prepared in a manner analogous to that of Example 9, using 7.3 grams (0.023 mole) of 4-cyano-3-methoxy-7-(4-trifluoromethylphenyl)-3-octene, and 10.5 grams (0.058 mole) of guanidine carbonate in 30 mL of N,N-dimethylacetamide. The yield of 2,4-diamino-5-[3-(4-trifluoromethylphenyl)butyl]-6-ethylpyrimidine was 2.4 grams, mp 48°–55° C. The NMR spectrum was consistent with the proposed structure.

EXAMPLE 31

SYNTHESIS OF 2,4-DIAMINO-5-[3-(2,4-DICHLOROPHENYL)BUTYL]-6-METHYLPYRIMIDINE (Compound 139)

This compound was prepared in a manner analogous to that of Example 29, using 1.9 grams (0.006 mole) of 3-cyano-2-methoxy-6-(2,4-dichlorophenyl)-2-heptene and 2.8 grams(0.015 mole) of guanidine carbonate in 30 mL of N,N-dimethylacetamide. The yield of 2,4-diamino-5-[3-(2,4-dichlorophenyl)butyl]-6-methylpyrimidine was 0.6 gram, mp 164°–168° C. The NMR spectrum was consistent with the proposed structure.

EXAMPLE 32

SYNTHESIS OF 2,4-DIAMINO-5-[3-(4-CHLOROPHENYL)BUTYL]-6-METHYLPYRIMIDINE (Compound 140)

This compound was prepared in a manner analogous to that of Example 29, using 5.3 grams (0.02 mole) of 3-cyano-2-methoxy-6-(4-dichlorophenyl)-2-heptene and 9.2 grams (0.05 mole) of guanidine carbonate in 30 mL of N,N-dimethylacetamide. The yield of 2,4-diamino-5-[3-(4-dichlorophenyl)butyl]-6-methylpyrimidine was 1.7 grams, mp 125°–128° C. The NMR spectrum was consistent with the proposed structure.

EXAMPLE 33

SYNTHESIS OF 2,4-DIAMINO-5-[3-(2,4-DICHLOROPHENYL)PROPYL]-6-METHYLPYRIMIDINE (Compound 136)

The intermediates to Compound 136 were prepared in a manner analogous to that of Steps A–F of Example 5. Compound 136 was prepared as taught in Step D of Example 17, using 7.8 grams (0.028 mole) of 3-cyano-2-methoxy-6-(2,4-dichlorophenyl)-2-hexene and 12.4 grams (0.069 mole) of guanidine carbonate in 30 mL of N,N-dimethylacetamide. The yield of 2,4-diamino-5-[3-(2,4-dichlorophenyl)propyl]-6-methyl-pyrimidine was 1.0 gram; mp 181°–185° C. The NMR spectrum was consistent with the proposed structure.

EXAMPLE 34

SYNTHESIS OF 2,4-DIAMINO-5-[3-[3-(4-TRIFLUOROMETHYLPHENYL)PHENYL]BUTYL]-6-METHYLPYRIMIDINE (Compound 144)

Step A Synthesis of 4-triflurophenylboronic acid as an intermediate

A stirred solution of 20.0 grams (0.089 mole) of 4-trifluoromethylphenyl bromide in 150 mL of tetrahydrofuran was cooled in a dry ice/acetone bath, and 47 mL (0.093 mole) of a 2.0 molar solution of n-butyllithium in tetrahydrofuran was added dropwise. Upon completion of addition, the reaction mixture was stirred for about 1.5 hours with continued cooling with the dry ice/acetone bath. After this time, 30 mL (0.270 mole) of trimethyl borate was added dropwise. Upon completion of addition, the reaction mixture was allowed to warm to ambient temperature as it stirred during about an 18 hour period. The reaction mixture was then concentrated under reduced pressure to a residual oil. The oil was poured into 250 mL of aqueous 10% hydrochloric acid, at which time a white precipitate formed. The mixture was stirred for about 18 hours, and the precip-itate was collected by filtration, yielding 13.7 grams of 4-trifluorophenylboronic acid. The NMR spectrum was consistent with the proposed structure.

Step B Synthesis of 3-(4-trifluoromethylphenyl)phenyl bromide as an intermediate A solution of 13.7 grams (0.072 mole) of 4-trifluorophenylboronic acid, 50.0 grams (0.21 0 mole) of 1,3-dibromobenzene, and 0.2 gram (catalyst) of tetrakis-(triphenylphosphine)palladium(0) in 150 mL of toluene was stirred, and 150 mL of an aqueous 2.0 molar solution of sodium carbonate was added. Upon comp-letion of addition, the reaction mixture was warmed to reflux where it was stirred for about 18 hours. After this time the reaction mixture was cooled, and excess 1,3-dibromobenzene was removed by vacuum distillation. The residue from the distillation was subjected to column chromatography, using heptane as the eluant. The product-containing fractions were combined and concentrated under reduced pressure to a residue. A small amount of remaining 1,3-dibromo-benzene was removed by vacuum distillation, yielding 15.7 grams of 3-(4-tri-fluoromethylphenyl)phenyl bromide. The NMR spectrum was consistent with the proposed structure.

Step C Synthesis of 5-hydroxy-5-[3-(4-trifluoromethylphenyl)phenyl]hexanenitrile as an intermediate Under a nitrogen atmosphere a stirred solution of 7.5 grams (0.025 mole) of 3-(4-trifluoromethylphenyl)phenyl bromide in 100 mL of tetrahydrofuran was cooled to about −78 ° C., and 10.0 mL (0.025 mole) of n-butyllithium (2.5 molar in hexane) was added dropwise. Upon completion of addition, the reaction mixture was stirred at -78 ° C. for about one hour. After this time a solution of 2.8 grams (0.025 mole) of 5-oxohexanenitrile in 10 mL of tetrahydrofuran was added dropwise. Upon completion of addition, the reaction mixture was allowed to warm to ambient temperature as it stirred for about 18 hours. After this time the reaction mixture was diluted with diethyl ether and partitioned between an aqueous dilute solution of hydrochloric acid and diethyl ether. The organic layer was separated and dried with sodium sulfate. The mixture was filtered and concentrated under reduced pressure to a residue. The residue was subjected to column chromatography on silica gel, using 1:1 ethyl acetate and hexane as the eluant. The product-containing fractions were concentrated under reduced pressure, yielding about 3.0 grams of 5-hydroxy-5-[3-(4-trifluoromethylphenyl)phenyl]hexanenitrile. The NMR spectrum was consistent with the proposed structure. This reaction was repeated.

Step D Synthesis of 5-[3-(4-trifluoromethylphenyl)phenyl] hexanenitrile as an intermediate Under a nitrogen atmosphere a stirred solution of 4.8 grams (0.014 mole) of 5-hydroxy-5-[3-(4-trifluoromethylphenyl)phenyl]hexanenitrile in 40 mL (0.760 mole) of acetonitrile was cooled to 0 ° C., and 9.4 grams (0.086 mole) of trimethyl-silyl chloride was added slowly. Upon completion of addition, the reaction mixture was stirred for about 15 minutes, and then 40 mL of hexane was added. After this time the reaction mixture was again stirred for 15 minutes, and 13.0 grams (0.086 mole) of sodium iodide was added. The reaction mixture was then stirred as it was allowed to warm to ambient temperature. Thin layer chroma-tographic analysis of the reaction mixture indicated that the reaction was not complete. The reaction mixture was then warmed to reflux where it stirred for two hours. After this time the reaction mixture was allowed to cool to ambient temperature as it stirred for about 18 hours. The reaction mixture was then partitioned between ethyl acetate and water. The organic layer was separated and washed with an aqueous dilute solution of sodium metabisulfite to remove iodine. The organic layer was then dried with sodium sulfate and filtered. The filtrate was concentrated under reduced pressure to a residue. The residue was subjected to column chromatography on silica gel, using 25% ethyl acetate in hexane as the eluant. The product-containing fractions were combined and concentrated under reduced pressure, yielding about 3.2 grams of 5-[3-(4-trifluoromethylphenyl)phenyl] hexanenitrile. The NMR spectrum was consistent with the proposed structure.

Step E Synthesis of 3-cyano-2-oxo-6-[3-(4-trifluoromethylphenyl)phenyl]heptane as an intermediate Under a nitrogen atmosphere a stirred solution of 2.5 grams (0.008 mole) of 5-[3-(4-trifluoromethylphenyl) phenyl]hexanenitrile in 20 mL of tetrahydrofuran was cooled to about −78 ° C., and 3.2 mL (0.008 mole) of n-butyllithium (2.5 molar in hexane) was added dropwise. Upon completion of addition, the reaction mixture was stirred at −78 ° C. for 30 minutes, and then 1.1 grams (0.012 mole) of ethyl acetate was added dropwise. Upon completion of addition, the reaction mixture was allowed to warm to ambient temperature as it stirred for about 60 hours. The reaction mixture was partitioned between ethyl acetate and aqueous dilute hydro-chloric acid. The organic layer was dried with sodium sulfate and filtered. The filtrate was concentrated under reduced pressure to a residue. The residue was subjected to column chromatography on silica gel, using 25% ethyl acetate in hexane as the eluant. The product-containing fractions were combined and concentrated under reduced pressure, yielding about 0.9 gram of 3-cyano-2-oxo-6-[3-(4-trifluoromethylphenyl)phenyl] heptane. The NMR spectrum was consistent with the proposed structure.

Step F Synthesis of 2-methoxy-3-cyano-6-[3-(4-trifluoromethylphenyl)phenyl]-2-heptene as an intermediate This compound was prepared in a manner analogous to that of Step D of Example 2, using 0.4 gram (0.001 mole) of 3-cyano-2-oxo-6-[3-(4-trifluoromethylphenyl)heptane and 0.4 gram (0.002 mole) of Diazald in 50 mL of diethyl ether. The yield of 2-methoxy-3-cyano-6-[3-(4-trifluoromethylphenyl)phenyl]-2-heptene was about 0.6 gram. The NMR spectrum was consistent with the proposed structure.

Step G Synthesis of 2,4-diamino-5-[3-[3-(4-trifluoromethylphenyl)phenyl]butyl]-6-methylpyrimidine (Compound 144)

This compound was prepared in a manner analogous to that of Step E of Example 17, using 0.5 gram (0.001 mole) of 2-methoxy-3-cyano-6-[3-(4-trifluoromethylphenyl) phenyl]-2-heptene and 0.6 gram (0.003 mole) of guanidine carbonate in 25 mL of N,N-dimethylacetamide. The yield of 2,4-diamino-5-[3-[3-( 4-trifluoromethylphenyl)phenyl] butyl]-6-methylpyrimidine was about 0.2 gram; mp 67°–68 ° C. The NMR spectrum was consistent with the proposed structure.

EXAMPLE 35

SYNTHESIS OF 2,4-DIAMINO-5-[3-(3,5-DICHLOROPHENYL)BUTYL]-6-METHYLPYRIMIDINE (Compound 141 )

Step A Synthesis of 5-hydroxy-5-(3,5-dichlorophenyl) hexanenitrile as an intermediate The Grignard reagent of 3,5-dichlorophenyl iodide was prepared by the reaction of 20.0 grams (0.073 mole) of 3,5-dichlorophenyl iodide and 1.8 grams (0.073 mole) of magnesium turnings in 350 mL of diethyl ether. The reaction mixture was heated at reflux for about three hours and then allowed to cool to ambient temperature. To the Grignard reagent, with stirring, was added dropwise during a 15 minute period a solution of 8.4 mL (0.073 mole) of 5-oxohexanenitrile in 25 mL of diethyl ether. The exothermic reaction caused the reaction mixture temperature to rise to about 30 ° C. Upon completion of addition, the reaction mixture was stirred for one hour and then was poured into 400 mL of water. The mixture was made acidic with about 80 mL of aqueous 2N hydrochloric acid and extracted with two 200 mL portions of diethyl ether. The combined extracts were dried with magnesium sulfate and filtered. The filtrate was concentrated under reduced pressure to a residue. The residue was subjected to column chroma-tography on silica gel, using 5% diethyl ether in methylene chloride as the eluant. The product-containing fractions were combined and concentrated under reduced pressure, yielding 8.4 grams of 5-hydroxy-5-(3,5-dichlorophenyl)hexanenitrile. The NMR spectrum was consistent with the proposed structure.

Step B Synthesis of 5-(3,5-dichlorophenyl)hexanenitrile as an intermediate

This compound was prepared in a manner analogous to that of Step D of Example 34, using 8.4 grams (0.033 mole) of 5-hydroxy-5-(3,5-dichlorophenyl)hexanenitrile, 24.7 mL (0.198 mole) of trimethylsilyl chloride, 29.3 grams (0.198 mole) of sodium iodide, and 15.3 mL (0.297 mole) of acetonitrile in 10 mL of hexane. The yield of 5-(3,5-dichlorophenyl)hexanenitrile was 3.6 grams. The NMR spectrum was consistent with the proposed structure.

Step C Synthesis of 3-cyano-2-oxo-6-(3,5-dichlorophenyl) heptane as an intermediate This compound was prepared in a manner analogous to that of Step E of Example 34, using 3.6 grams (0.015 mole) of 5-(3,5-dichlorophenyl)hexanenitrile, 2.2 mL (0.01 7 mole) of ethyl acetate, and 6.6 mL (0.023 mole) of n-butyllithium (2.5M in hexanes) in 75 mL of tetrahydrofuran. The yield of 3-cyano-2-oxo-6-(3,5-dichlorophenyl) heptane was 4.3 grams.

Step D Synthesis of 2-methoxy-3-cyano-6-(3,5-dichlorophenyl)-2-heptene as an intermediate This compound was prepared in a manner analogous to that of Step D of Example 2, using 4.3 grams (0.015 mole) of 3-cyano-2-oxo-6-(3,5-dichlorophenyl)heptane, 5.5 grams (0.026 mole) of Diazald, 10 grams of potassium hydroxide, and 16 mL of water in 20 mL of ethanol. The yield of 2-methoxy-3-cyano-6-(3,5-dichlorophenyl)-2-heptene was about 4.4 grams. The NMR spectrum was consistent with the proposed structure.

Step F Synthesis of 2,4-diamino-5,-[3-(3,5-dichlorophenyl) butyl]-6-methylpyrimidine (Compound 141)

This compound was prepared in a manner analogous to that of Step E of Example 17, using 4.4 grams (0.015 mole) of 2-methoxy-3-cyano-6-(3,5-dichlorophenyl)-2-heptene and 6.7 grams (0.038 mole) of guanidine carbonate in 30 mL of N,N-dimethylacetamide. The yield of 2,4-diamino-5-[3-(3,5-dichlorophenyl)butyl]-6-methylpyrimidine was about 3.5 grams. The NMR spectrum was consistent with the proposed structure.

EXAMPLE 36

SYNTHESIS OF 2,4-DIAMINO-5-[4-[4-(3,5-DIFLUOROPHENYL)PHENYL]PENTYL]-6-METHYLPYRIMIDINE (Compound 148)

Step A Synthesis of ethyl 5-(4-methoxyphenyl)-2,4-hexadienoate as an intermediate A stirred solution of 25.3 grams (0.230 mole) of potassium tert.-butoxide in 250 mL of tetrahydrofuran was cooled to 0° C., and a solution of 56.5 grams (0.230 mole) triethyl 4-phosphonocrotonate in 50 mL of tetrahydrofuran was added dropwise while maintaining the reaction mixture temperature at about 0°–10° C. The complete addition required about 30 minutes. The reaction mixture was then stirred for one hour at 0°–5° C., and then 26.6 grams (0.180 mole) of 4-methoxyacetophenone was added in one portion. Upon completion of addition, the reaction mixture was allowed to warm to ambient temperature as it stirred for about 18 hours. After this time the reaction mixture was made acidic with an aqueous 2N hydrochloric acid solution and diluted with about 200 mL of water. The mixture was extracted with two 250 mL portions of diethyl ether. The combined extracts were washed with one 250 mL portion of an aqueous solution saturated with sodium chloride. The organic layer was dried with magnesium sulfate and filtered. The filtrate was taken up in 150 grams of silica gel, and the solvent was removed under reduced pressure. The silica gel mixture was placed on top of a column of silica gel, and the mixture was eluted with 10% ethyl acetate in petroleum ether. The product-Containing fractions were combined and concentrated under reduced pressure, yielding 6.9 grams of ethyl 5-(4-methoxyphenyl)-2,4-hexadienoate. The NMR spectrum was consistent with the proposed structure. This reaction was repeated several times.

Step B Synthesis of ethyl 5-(4-methoxyphenyl)hexanoate as an intermediate

This compound was prepared in a manner analogous to that of Step B of Example 3, using 24.3 grams (0.099 mole) of ethyl 5-(4-methoxyphenyl)-2,4-hexadienoate, hydrogen gas, and 0.3 gram (catalyst) of platinum oxide in 300 mL of ethanol. The yield of ethyl 5-(4-methoxyphenyl)hexanoate was 24.3 grams. The NMR spectrum was consistent with the proposed structure.

Step C Synthesis of 5-(4-methoxyphenyl)hexan-1-ol as an intermediate

This compound was prepared in a manner analogous to that of Step B of Example 9, using 24.3 grams (0.097 mole) of ethyl 5-(4-methoxyphenyl)hexanoate and 2.4 grams (0.063 mole) of lithium aluminum hydride in 300 mL of diethyl ether. The yield of 5-(4-methoxyphenyl)hexan-1-ol was 19.8 grams. The NMR spectrum was consistent with the proposed structure. This reaction was repeated several times Step D Synthesis of 1-methylsulfonyloxy-5-(4-methoxyphenyl)hexane as an intermediate This compound was prepared in a manner analogous to that of Step A of Example 2, using 41.4 grams (0.199 mole) of 5-(4-methoxyphenyl)hexan-1-ol, 17.6 mL (0.228 mole) of methanesulfonyl chloride, and 31.8 mL (0.228 mole) of triethylamine in 400 mL of m, ethylene chloride. The yield of 1methylsulfonyloxy-5-(4-methoxyphenyl)hexane was 56.9 grams. The NMR spectrum was consist-ent with the proposed structure.

Step E Synthesis of 6-(4-methoxyphenyl)heptanenitrile as an intermediate

This compound was prepared in a manner analogous to that of Step B of Example 2, using 56.9 grams (0.199 mole) of 1-methylsulfonyloxy-5-(4methoxyphenyl)hexane and 19.6 grams (0.400 mole) of sodium cyanide in 400 mL of N,N-dimethylformamide. The yield of 6-(4-methoxyphenyl) heptanenitrile was 42.1 grams. The NMR spectrum was consistent with the proposed structure.

Step F Synthesis of 3-cyano-2-oxo-7-(4-methoxyphenyl) octane as an intermediate

This compound was prepared in a manner analogous to that of Step E of Example 34, using 23.0 grams (0.106 mole) of 6-(4-methoxyphenyl)heptanenitrile, 13.9 mL (0.142 mole) of ethyl acetate, and 46.8 mL (0.117 mole) of n-butyllithium (2.5M in hexanes) in 330 mL of tetrahydrofuran. The yield of 3-cyano-2-oxo-7-(4-methoxyphenyl) octane was 27.5 grams. The NMR spectrum was consistent with the proposed structure.

Step G Synthesis of 2-methoxy-3-cyan0°–7-(4-methoxyphenyl)-2-octene as an intermediate This compound was prepared in a manner analogous to that of Step D of Example 2, using 14.0 grams (0.054 mole) of 3-cyano-2-oxo-7-(4-methoxyphenyl)octane, 19.1 grams (0.089 mole) of Diazald, 16.8 grams of potassium hydroxide, and 18 mL of water in 20 mL of ethanol. The yield of 2-methoxy-3-cyano-7-(4-methoxyphenyl)-2-octene was 14.8 grams. The NMR spectrum was consistent with the proposed structure.

Step H Synthesis of 2,4-diamino-5-[4-( 4-methoxyphenyl) pentyl]-6-methylpyrimidine (Compound 147) for insecticide testing and as an intermediate This compound was prepared in a manner analogous to that of Step E of Example 17, using 14.8 grams (0.054 mole) of 2-methoxy-3-cyano-7-(4-methoxyphenyl)-2-octene and 26.0 grams (0.144 mole) of guanidine carbonate in 100 mL of N,N-dimethylacetamide. The yield of 2,4-diamino-5-[4-(4-methoxyphenyl)-pentyl]-6-methylpyrimidine was about 7.1 grams, mp 135°–137 ° C. The NMR spectrum was consistent with the proposed structure.

Step I Synthesis of 2,4-diamino-5-[4-(4-hydroxyphenyl) pentyl]-6-methylpyrimidine (Compound 146) for insecticide testing and as an intermediate A stirred mixture of 5.2 grams (0.01 7 mole) of 2,4-diamino-5-[4-(4methoxyphenyl)pentyl]-6-methylpyrimidine in 200 mL of methylene chloride was cooled to about 0 ° C., and 52 ml (0.052 mole) of boron tribromide (1M in methylene chloride) was added dropwise during a 20 minute period while maintaining the reaction mixture temperature between –5 ° C. and +5 ° C. Upon completion of addition, the reaction was allowed to warm to ambient temperature as it stirred for about 18 hours. After this time the reaction mixture was poured into about 200 grams of ice. The mixture was made slightly basic with concentrated ammonium hydroxide and was stirred until the ice melted. A solid precipitate was collected by filtration and dried at 60° C., yielding 4.9 grams of 2,4-diamino-5-[4-(4-hydroxyphenyl)pentyl]-6-methylpyrimidine, mp 197°–201 ° C., dec. The NMR spectrum was consistent with the proposed structure.

Step J Synthesis of 2,4-diamino-5-[4-(4-trifluoromethylsulfonyloxyphenyl)pentyl]-6-methylpyrimidine as an intermediate A mixture of 1.4 grams (0.005 mole) of 2,4-diamino-5-[4-(4-hydroxyphenyl)pentyl]-6-methylpyrimidine and 1.0 mL (0.012 mole) of pyridine in about 20 mL of methylene chloride was stirred, and 1.1 grams (0.007 mole) of trifluoromethanesulfonic anhydride was added in one portion. Upon completion of addition, the reaction mixture was stirred at ambient temperature for about 90 minutes. The reaction mixture was then concentrated under reduced pressure to a residue. The residue was washed with three 75 mL portions of an aqueous 10% lithium chloride solution. The organic layer was dried with sodium sulfate, filtered, and concentrated under reduced pressure to a residue. The residue was taken up in 50 mL of toluene and concentrated under reduced pressure to a residue to remove excess pyridine. The residue was again taken up in 50 mL of toluene and concentrated under reduced pressure, yielding about 1.9 grams of 2,4-diamino-5-[4-( 4-trifluoromethylsulfonyloxyphenyl)pentyl]-6-methylpyrimidine. The NMR spectrum was consistent with the proposed structure.

Step K Synthesis of 3,5-difluorophenylboronic acid as an intermediate

The Grignard reagent of 3,5-difluorophenyl bromide was prepared using 21.0 grams (0.109 mole) of 3,5-difluorophenyl bromide and 2.7 grams (0.109 mole) of magnesium turnings in about 30 mL of tetrahydrofuran.

In a separate reaction vessel, 40 mL of tetrahydrofuran was cooled to –78 ° C., and the Grignard reagent of 3,5-difluorophenyl bromide and a solution of 11.3 grams (0.109 mole) of trimethyl borate in 15 mL of tetrahydrofuran were added simultaneously dropwise in an effort to provide an equimolar addition of each. An additional 115 mL of tetrahydrofuran was added during the additions to dilute the thickening reaction mixture. The completion of additions required about 15 minutes. After this time the reaction mixture was allowed to warm to ambient temperature as it stirred for about 18 hours. The reaction mixture was then poured into 300 mL of an aqueous dilute solution of hydrochloric acid. The resultant mixture was extracted with two 150 mL portions of ethyl acetate. The combined extracts were dried with magnesium sulfate and filtered. The filtrate was concentrated under reduced pressure, yielding 13.6 grams of 3,5-difluoro-phenylboronic acid. The NMR spectrum was consistent with the proposed structure.

Step L Synthesis of 2,4-diamino-5-[4-[4-(3,5-difluorophenyl)phenyl]pentyl]-6-methylpyrimidine (Compound 148)

A solution of 2.0 grams (0.005 mole) of 2,4-diamino-5-[4-(4-trifluoromethylsulfonyloxyphenyl)pentyl]-6-methylpyrimidine (prepared in Step K of this Example), 2.4 grams (0.015 mole) of 3,5-difluorophenylboronic acid, and 0.3 gram (catalyst) of tetrakis(triphenylphosphine)palladium (0) in 90 mL of N,N-dimethylformamide was stirred, and 3.5 grams (0.025 mole) of potassium carbonate was added in one portion. Upon completion of addition, the reaction mixture was warmed slowly to 115 ° C. where it was maintained for about 40 hours. The reaction mixture was cooled and poured into 250 mL of water. The mixture was then extracted with three 1 50 mL portions of ethyl acetate. The combined extracts were washed with three 150 mL portions of an aqueous 10% lithium chloride solution and dried with sodium sulfate. The mixture was filtered, and the filtrate was concentrated under reduced pressure to a residue. The residue was subjected to column chromatography on neutral alumina (deactivated with 6% wt/wt water), using 2–10% methanol in methylene chloride as the eluants. The product-containing fractions were combined and concentrated under reduced pressure, yielding about 0.5 gram of 2,4-diamino-5-[4-[4-(3,5-difluorophenyl)phenyl]pentyl]-6-methylpyrimidine, mp 129°–134° C. The NMR spectrum was consistent with the proposed structure.

EXAMPLE 37

SYNTHESIS OF 2,4-DI(METHYLCARBONYLAMINO)-5-[3-(4-CHLOROPHENYL)BUTYL]-6-METHYLPYRIMIDINE (Compound 149)

Under a nitrogen atmosphere, a stirred mixture of 1.2 grams (0.004 mole) of 2,4-diamino-5-[3-(4-chlorophenyl) butyl]-6-methylpyrimidine (Compound 140-prepared in Example 32), 2.0 grams (0.020 mole) of acetic anhydride, and a catalytic amount of 4-dimethylaminopyridine was heated at reflux for about 18 hours. After this time the reaction mixture was poured into 200 grams of ice/water and stirred until the ice melted. The mixture was then extracted with two portions of diethyl ether. The combined extracts were washed with three portions of aqueous 5% sodium hydroxide. The organic layer was dried with magnesium sulfate and filtered. The filtrate was concentrated under reduced pressure, yielding about 0.3 gram of 2,4-di(methylcarbonylamino)-5-[3-(4-chlorophenyl)butyl]-6-methylpyrimidine, mp 136°–138 ° C. The NMR spectrum was consistent with the proposed structure.

Tables 1 and 1-a.

Appended TABLE 1 lists 180 species of pyrimidines and salts thereof falling within Formula I (supra) of this invention, the preparation of certain of which species are illustrated in accordance with foregoing Examples 1–37. Table 1-a lists the physical properties of the compounds of Table 1.

TABLE 1

5-SUBSTITUTED-2,4-DIAMINOPYRIMIDINES

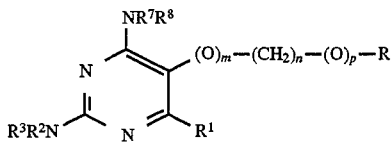

where m and p are 0, and $R^2$, $R^3$, $R^7$ and $R^8$ are hydrogen

| Cmpd No. | n | R | $R^1$ |
|---|---|---|---|
| 1 | 0 | H | —CH₃ |
| 2 | 0 | H | n-pentyl |
| 3 | 5 | CH₃ | H |
| 4 | 11 | —CH₃ | H |
| 5 | 1 | —CH₃ | phenyl |
| 6 | 2 | cyclohexyl | H |
| 7 | 1 | H | n-propyl |
| 8 | 1 | CH₃ | 4-phenylbutyl |
| 9 | 2 | CH₃ | 2-phenylethyl |
| 10 | 3 | CH₃ | phenylmethyl |
| 11 | 3 | CH₃ | 5-phenylpentyl |
| 12 | 4 | CH₃ | 3-phenylpropyl |
| 13 | 1 | cyclohexyl | ethyl |
| 14 | 3 | cyclohexyl | ethyl | where m and p are 0, $R^2$, $R^3$, $R^7$ and $R^8$ are hydrogen, and R is

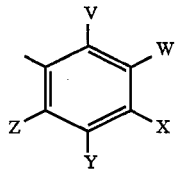

| Cmpd. No. | n | $R^1$ | V | W | X | Y | Z |
|---|---|---|---|---|---|---|---|
| 15 | 0 | H | H | H | H | H | H |
| 16 | 1 | H | H | H | H | H | H |
| 17 | 1 | H | H | H | —OCH₃ | H | H |
| 18 | 1 | H | H | F | H | F | H |
| 19 | 1 | H | H | Cl | Cl | H | Cl |
| 20 | 1 | H | H | —OCH₃ | —OCH₃ | —OCH₃ | H |
| 21 | 1 | —C₂H₅ | H | H | H | H | H |
| 22 | 1 | —C₂H₅ | H | ø | H | H | H |
| 23 | 1 | —C₂H₅ | Cl | H | Cl | Cl | H |
| 24 | 1 | n-butyl | H | H | H | H | H |
| 25 | 2 | H | H | H | H | H | H |
| 26 | 2 | H | H | H | Cl | H | H |
| 27 | 2 | H | H | ø | H | H | H |
| 28 | 2 | H | Cl | H | Cl | Cl | H |
| 29 | 2 | —CH₃ | H | H | H | H | H |
| 30 | 2 | —C₂H₅ | H | H | —OCH₃ | H | H |
| 31 | 3 | H | H | H | H | H | H |
| 32 | 3 | H | H | H | —OCH₃ | H | H |
| 33 | 3 | —C₂H₅ | H | ø | H | H | H |
| 34 | 3 | —C₂H₅ | Cl | H | Cl | Cl | H |
| 35 | 3 | n-propyl | H | H | H | H | H |
| 36 | 3 | n-pentyl | H | H | H | H | H |
| 37 | 4 | H | H | H | H | H | H |
| 38 | 4 | —C₂H₅ | Cl | H | Cl | Cl | H |
| 39 | 4 | —C₂H₅ | Cl | H | Cl | Cl | H |
| | | | | | hydrochloride salt | | |
| 40 | 4 | ø | H | H | H | H | H |
| 41 | 5 | H | H | H | H | H | H |
| 42 | 5 | 2-phenylethyl | H | H | H | H | H |
| 43 | 5 | 4-phenylbutyl | H | H | H | H | H |
| 44 | 6 | H | H | H | H | H | H |

TABLE 1-continued

5-SUBSTITUTED-2,4-DIAMINOPYRIMIDINES where m and p are 0 $R^7$ and $R^8$ are hydrogen, and R is

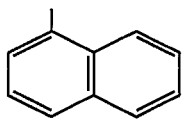

| Cmpd No. | n | $R^1$ | $R^2$ | $R^3$ |
|---|---|---|---|---|
| 45 | 1 | H | H | H |
| 46 | 2 | —$C_2H_5$ | H | H |
| 47 | 3 | H | H | H |
| 48 | 3 | —$NH_2$ | H | H |
| 49 | 3 | H | —$CH_3$ | H |
| 50 | 3 | H | —$C_2H_5$ | H |
| 51 | 3 | H | —$CH_3$ | —$CH_3$ |
| 52 | 3 | H | —$CH_2CH_2OCH_2CH_2$— | |
| 53 | 4 | H | H | H |
| 54 | 5 | H | H | H |
| 55 | 6 | H | H | H | where m is 1, p is 0 and $R^1$, $R^2$, $R^3$, $R^7$ and $R^8$ are hydrogen

| Cmpd No. | n | R |
|---|---|---|
| 56 | 1 | —$CH(C_2H_5)_2$ |
| 57 | 11 | —$CH_3$ |
| 58 | 4 | —CN | where m is 1, p is 0, $R^1$, $R^2$, $R^3$, $R^7$ and $R^8$ are hydrogen, and R is

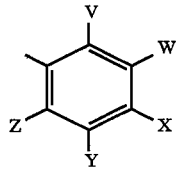

| Cmpd No. | n | V | W | X | Y | Z |
|---|---|---|---|---|---|---|
| 59 | 1 | H | F | H | F | H |
| 60 | 1 | Cl | H | Cl | Br | H |
| 61 | 5 | H | H | —$CO_2C_2H_5$ | H | H | where m and p are 0; $R^1$, $R^2$, $R^3$, $R^7$ and $R^8$ are hydrogen

| Cmpd No. | n | R |
|---|---|---|
| 62 | 7 | —$CH_3$ |
| 63 | 7 | —$CH_3$ Hydrochloride |
| 64 | 1 | —$Si(CH_3)_3$ |
| 65 | 3 | —$Si(CH_3)_3$ |
| 66 | 3 | —N⟨ ⟩O (morpholino) |

TABLE 1-continued

5-SUBSTITUTED-2,4-DIAMINOPYRIMIDINES where m and p are 0, $R^1$, $R^2$, $R^3$, $R^7$ and $R^8$ are hydrogen, and R is

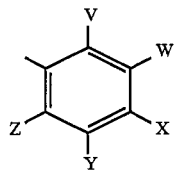

where V, W, Y, and Z are hydrogen

| Cmpd No. | n | X |
|---|---|---|
| 67 | 4 | —Cl |
| 68 | 4 | —Cl Hydrochloride |
| 69 | 5 | —OCH₃ |
| 70 | 7 | —OCH₃ | where m, n and p are 0, $R^2$, $R^3$, $R^7$ and $R^8$ are hydrogen, $R^1$ is ethyl, and R is

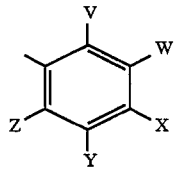

where V, Y, and Z are hydrogen; and X is chloro.

| Cmpd No. | W | $R^5$ |
|---|---|---|
| 71 | —NO₂ | — |
| 72 | —NHR⁵ | —C₅H₁₁ |
| 73 | —NHR⁵ | —C₅H₁₁·3HCl |
| 74 | —NHR⁵ | —C₁₁H₂₃ |
| 75 | —NHR⁵ | cyclopentyl |
| 76 | —NHR⁵ | cyclopentyl ·3HCl |
| 77 | —NHR⁵ | —CH₂—C₆H₄—Cl |
| 78 | —NHR⁵ | —C₄H₈—C₆H₄—Cl |
| 79 | —NHR⁵ | —C₂H₄O—C₆H₄—SO₂C₃H₇ |
| 80 | —NHR⁵ | —CH₂—(2-pyridyl) |

TABLE 1-continued

5-SUBSTITUTED-2,4-DIAMINOPYRIMIDINES

| | | |
|---|---|---|
| 81 | —NHR$^5$ | 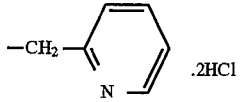 .2HCl |

| Cmpd No. | W | R$^4$ |
|---|---|---|
| 82 | —NHC(O)R$^4$ | —C$_4$H$_9$ |
| 83 | —NHC(O)R$^4$ | —C(CH$_3$)$_3$ |
| 84 | —NHC(O)R$^4$ | —C$_9$H$_{19}$ |
| 85 | —NHC(O)R$^4$ | —C$_{10}$H$_{21}$ |
| 86 | —NHC(O)R$^4$ | —C$_3$F$_7$ |
| 87 | —NHC(O)R$^4$ | 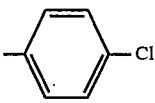 |
| 88 | —NHC(O)R$^4$ | 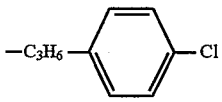 |
| 89 | —NHC(O)R$^4$ |  | where m is 0, p is 1, n is 3, R$^1$, R$^2$, R$^3$, R$^7$ and R$^8$ are hydrogen

| Cmpd No. | R |
|---|---|
| 90 | —C$_4$H$_9$ |
| 91 | 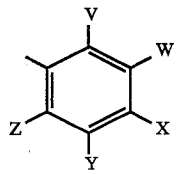 | where m is 0, p is 1, R$^1$, R$^2$, R$^3$, R$^7$ and R$^8$ are hydrogen, and R is

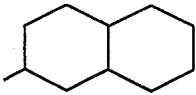

where V, W, Y, and Z are hydrogen

| Cmpd No. | n | X |
|---|---|---|
| 92 | 3 | —SC$_3$H$_7$ |
| 93 | 3 | —SO$_2$C$_3$H$_7$ |
| 94 | 3 | —SO$_2$C$_3$H$_7$ Hydrochloride |
| 95 | 5 | —SC$_3$H$_7$ |
| 96 | 5 | —SO$_2$C$_3$H$_7$ |

| Cmpd No. | m | n | p | R | R$^1$ | R$^2$ | R$^3$ | R$^7$ | R$^8$ |
|---|---|---|---|---|---|---|---|---|---|
| 97 | 1 | 1 | 0 | —CH(C$_2$H$_5$)$_2$ | H | H | H | H | H |

TABLE 1-continued

5-SUBSTITUTED-2,4-DIAMINOPYRIMIDINES where m is 1, p is 0, and $R^2$, $R^3$, $R^7$ and $R^8$ are hydrogen, and R is

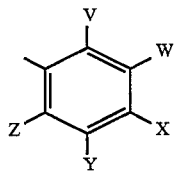

where Z is hydrogen.

| Cmpd No. | n | $R^1$ | V | W | X | Y |
|---|---|---|---|---|---|---|
| 98 | 1 | H | H | H hydrochloride | —$C_2H_5$ | H |
| 99 | 1 | H | Cl | H | Cl | Br |
| 100 | 0 | —$C_2H_5$ | H | —$C_{11}H_{23}$ | H | H |
| 101 | 0 | —$C_2H_5$ | H | —$CH(C_2H_5)_2$ | H | H |
| 102 | 0 | —$C_2H_5$ | H | —$OC_4H_9$ | H | H |
| 103 | 0 | —$C_2H_5$ | H | —$CH_2Si(CH_3)_3$ | H | H |
| 104 | 5 | H | H | H | —$CO_2C_2H_5$ | H |
| 105 | 0 | —$C_2H_5$ | H | —$CH_2$—⟨C₆H₄⟩—Cl | H | H |
| 106 | 0 | —$C_2H_5$ | H | —$C_4H_8$—⟨C₆H₄⟩—$OCH_3$ | H | H |
| 107 | 0 | —$C_2H_5$ | H | —CH(OH)—⟨C₆H₅⟩ | H | H |
| 108 | 0 | —$C_2H_5$ | H | —$C_2H_2O$—⟨C₆H₄⟩—$SO_2C_3H_7$ | H | H |
| 109 | 0 | —$C_2H_5$ | H | —O—(decahydronaphthyl) | H | H | where m, p are 0, $R^2$, $R^3$, $R^7$ and $R^8$ are hydrogen;

| Cmpd No. | n | R | $R^1$ |
|---|---|---|---|
| 110 | 0 | adamantyl | —$CH_3$ |
| 111 | 4 | cyclohexyl | H |

TABLE 1-continued

5-SUBSTITUTED-2,4-DIAMINOPYRIMIDINES where m, p are 0, $R^2$, $R^3$, $R^7$, $R^8$ and Z are hydrogen, and R is

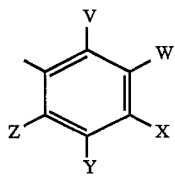

| Cmpd No. | n | $R^1$ | V | W | X | Y |
|---|---|---|---|---|---|---|
| 112 | 0 | $-C_2H_5$ | H | $-NO_2$ | —NHCH₂-(3,5-dichlorophenyl) | H |
| 113 | 0 | $-C_2H_5$ | H | $-NO_2$ | —NHCH₂-(4-methoxyphenyl) | H |
| 114 | 3 | $-CH_3$ | H | H | Cl | H |
| 115 | 3 | H | Cl | H | Cl | C |
| 116 | 3 | H | Cl | H | Cl | Cl |
|  |  | HCl salt |  |  |  |  |
| 117 | 3 | $-CH_3$ | Cl | H | Cl | Cl |
| 118 | 3 | $-C_2H_5$ | Cl | H | Cl | Cl |
|  |  | HCl salt |  |  |  |  |
| 119 | 5 | $-C_2H_5$ | Cl | H | Cl | Cl |
| 120 | 3 | $-CH_3$ | $-CF_3$ | H | H | H |
| 121 | 3 | $-CH_3$ | H | $-CF_3$ | H | H |
| 122 | 3 | $-CH_3$ | H | H | $-CF_3$ | H |
| 123 | 3 | $-CH_3$ | $-CH_3$ | H | H | H |
| 124 | 3 | $-CH_3$ | H | $-CH_3$ | H | H |
| 125 | 3 | $-CH_3$ | H | H | $-CH_3$ | H |
| 126 | 3 | $-CH_3$ | H | $-CH_3$ | $-CH_3$ | H |
| 127 | 3 | $-CH_3$ | H | $-CH_3$ | H | $-CH_3$ |
| 128 | 3 | $-CH_3$ | $-CH_3$ | H | $-CH_3$ | $-CH_3$ |
| 129 | 3 | $-CH_3$ | H | $-OC_2H_5$ | H | H |
| 130 | 3 | $-CH_3$ | H | H | $-OC_2H_5$ | H |
| 131 | 3 | $-CH_3$ | H | H | $-OC_3H_7$ | H | where m is 1, p is 0, $R^2$, $R^3$, $R^7$ and $R^8$ are hydrogen

| Cmpd No. | n | R | $R^1$ |
|---|---|---|---|
| 132 | 1 | $-CH(C_2H_5)_2$ | $-CH_3$ |
| 133 | 1 | cyclopentyl | H | where n is 3, $R^1$ is methyl, $R^2$, $R^3$, $R^7$ and $R^8$ are hydrogen, and R is

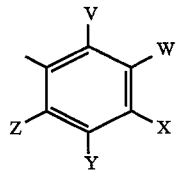

| Cmpd No. | m | p | V | W | X | Y | Z |
|---|---|---|---|---|---|---|---|
| 134 | 1 | 0 | H | H | H | H | H |
| 135 | 1 | 1 | $-CF_3$ | H | H | H | H |
| 136 | 0 | 0 | Cl | H | Cl | H | H |

TABLE 1-continued

5-SUBSTITUTED-2,4-DIAMINOPYRIMIDINES where m and p are 0, n is 2, $R^2$, $R^3$, $R^7$ and $R^8$ are hydrogen, and R is

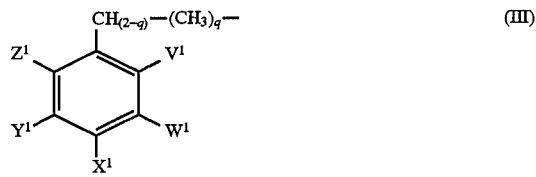
(III)

| Cmpd No. | q | $R^1$ | $V^1$ | $W^1$ | $X^1$ | $Y^1$ | $Z^1$ |
|---|---|---|---|---|---|---|---|
| 137 | 1 | —$C_2H_5$ | H | —$CF_3$ | H | H | H |
| 138 | 1 | —$C_2H_5$ | H | H | —$CF_3$ | H | H |
| 139 | 1 | —$CH_3$ | Cl | H | Cl | H | H |
| 140 | 1 | —$CH_3$ | H | H | Cl | H | H |
| 141 | 1 | —$CH_3$ | H | Cl | H | Cl | H | where m, p are 0; $R^1$ is methyl, $R^2$, $R^3$, $R^7$, and $R^8$ are hydrogen; and R is

| Cmpd. No. | n | q | $V^1$ | $W^1$ | $X^1$ | $Y^1$ | $Z^1$ |
|---|---|---|---|---|---|---|---|
| 142 | 2 | 1 | H | Cl | Cl | H | H |
| 143 | 2 | 1 | H | H | F | H | H |
| 144 | 2 | 1 | H | 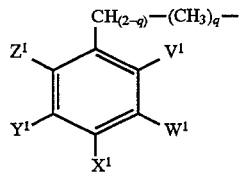 | H | H | H |
| 145 | 3 | 1 | H | H | Cl | H | H |
| 146 | 3 | 1 | H | H | OH | H | H |
| 147 | 3 | 1 | H | H | —$OCH_3$ | H | H |
| 148 | 3 | 1 | H | H | 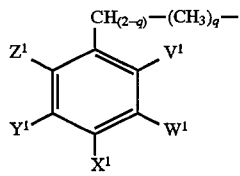 | H | H | where m, p are 0; n is 2; $R^1$ is methyl, $R^2$ and $R^7$ are hydrogen; and R is where q is 1; $V^1$, $W^1$, $Y^1$, and $Z^1$ are hydrogen; and $X^1$ is chloro

| Cmpd. No. | $R^3$ | $R^8$ |
|---|---|---|
| 149 | —C(O)CH₃ | —C(O)CH₃ |
| 150 | —C(O)C(CH₃)₃ | —C(O)C(CH₃)₃ |

TABLE 1-continued

5-SUBSTITUTED-2,4-DIAMINOPYRIMIDINES where m, p are 0; $R^1$ is methyl, $R^2$, $R^3$, $R^7$, and $R^8$ are hydrogen; and R is

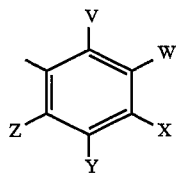

| Cmpd No. | n | V | W | X | Y | Z |
|---|---|---|---|---|---|---|
| 151 | 3 | H | H | F | H | H |
| 152 | 3 | H | Cl | Cl | H | H |
| 153 | 3 | H | H | $-C_2F_5$ | H | H |
| 154 | 3 | H | H | n-$C_4F_9$ | H | H |
| 155 | 3 | Cl | H | $-CF_3$ | H | H |
| 156 | 3 | H | H | $-OCF_3$ | H | H |
| 157 | 3 | H | H | $-OCH_3$ | H | H |
| 158 | 3 | H | H | $-CH_2OCH_3$ | H | H |
| 159 | 3 | H | H | $-SCH_3$ | H | H |
| 160 | 3 | H | H | $-SO_2CH_3$ | H | H |
| 161 | 3 | H | H | $-C\equiv N$ | H | H |
| 162 | 3 | $-C\equiv N$ | H | H | H | H contains molecule of DMF |
| 163 | 3 | H | H | NH2) | H | H |
| 164 | 3 | H | H | cc1) | H | H |
| 165 | 4 | Cl | H | Cl | H | H |
| 166 | 4 | Cl | H | $-OH$ | H | H |
| 167 | 4 | Cl | H | $-OCH_3$ | H | H |
| 168 | 4 | H | H | $-OH$ | H | H |
| 169 | 4 | H | H | $-OCH_3$ | H | H |
| 170 | 4 | H | H | ![3,5-difluorophenyl] | H | H |
| 171 | 4 | Cl | H | ![2-methoxypyridyl] | H | H | where m is 0; p is 1; $R^1$ is methyl, $R^2$, $R^3$, $R^7$, and $R^8$ are hydrogen; and R is

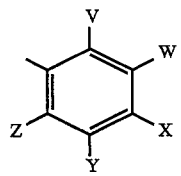

| Cmpd No. | n | V | W | X | Y | Z |
|---|---|---|---|---|---|---|
| 172 | 4 | $-CF_3$ | H | H | H | H |

TABLE 1-continued

5-SUBSTITUTED-2,4-DIAMINOPYRIMIDINES where m, p are 0; $R^1$ is methyl, $R^2$, $R^3$, $R^7$, and $R^8$ are hydrogen; and R is

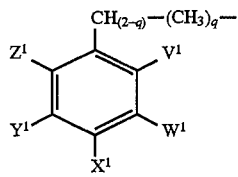

| Cmpd. No. | n | q | $V^1$ | $W^1$ | $X^1$ | $Y^1$ | $Z^1$ |
|---|---|---|---|---|---|---|---|
| 173 | 2 | 2 | H | H | Cl | H | H | where n is 3, $R^1$ is methyl, $R^2$, $R^3$, $R^7$ and $R^8$ are hydrogen, and R is

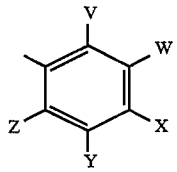

| Cmpd No. | m | p | V | W | X | Y | Z |
|---|---|---|---|---|---|---|---|
| 174 | 0 | 0 | Cl | H | Cl | H | H |
|  |  |  |  | HCl salt |  |  |  |
| 175 | 0 | 0 | Cl | H | Cl | H | H |
|  |  |  |  | Ethanesulfonic acid salt |  |  |  |
| 176 | 0 | 0 | Cl | H | Cl | H | H |
|  |  |  |  | Gluconic acid salt |  |  |  |
| 177 | 0 | 0 | Cl | H | Cl | H | H |
|  |  |  |  | Pamoic acid salt |  |  |  | where m and p are 0, n is 3, $R^1$ is methyl, $R^2$ and $R^7$ are hydrogen, and R is

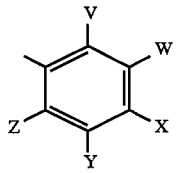

where W, Y, and Z are hydrogen; and V and W are chloro

| Cmpd. No. | $R^3$ | $R^8$ |
|---|---|---|
| 178 | —C(O)OCH$_3$ | —C(O)OCH$_3$ |
| 179 | —C(O)OC$_2$H$_5$ | —C(O)OC$_2$H$_5$ |
| 180 | —C(O)OC$_2$H$_4$OC$_2$H$_4$OCH$_3$ | —C(O)OC$_2$H$_4$OC$_2$H$_4$OCH$_3$ |

TABLE 1-a

MELTING POINT/EMPIRICAL FORMULA

| Compound Number | Melting Point (°C.) | Empirical Formula |
|---|---|---|
| 1 | 208–210 | $C_5H_8N$ |
| 2 | — | $C_9H_{16}N_4$ |
| 3 | 120–125 | $C_{10}H_{18}N_4$ |
| 4 | 123–125 | $C_{16}H_{30}N_4$ |
| 5 | 186–188 | $C_{12}H_{14}N_4$ |
| 6 | 177–179 | $C_{12}H_{20}N_4$ |

TABLE 1-a-continued

| Compound Number | Melting Point (°C.) | Empirical Formula |
|---|---|---|
| 7 | 164–165 | $C_8H_{14}N_4$ |
| 8 | 340–343, dec. | $C_{13}H_{10}Cl_2N_6$ |
| 9 | 127–128 | $C_{15}H_{20}N_4$ |
| 10 | 156–161 | $C_{15}H_{20}N_4$ |
| 11 | 96–98 | $C_{19}H_{28}N_4$ |
| 12 | 93–94 | $C_{18}H_{26}N_4$ |
| 13 | 172–176 | $C_{13}H_{22}N_4$ |
| 14 | 143–148 | $C_{15}H_{26}N_4$ |
| 15 | 162–164 | $C_{10}H_{10}N_4$ |
| 16 | 195–196 | $C_{11}H_{12}N_4$ |
| 17 | 195–200 | $C_{12}H_{14}N_4O$ |
| 18 | 243–245 | $C_{11}H_{10}F_2N_4$ |
| 19 | 246–248 | $C_{11}H_9Cl_3N_4$ |
| 20 | — | $C_{14}H_{18}N_4O_3$ |
| 21 | 157–160 | $C_{13}H_{16}N_4$ |
| 22 | 108–115 | $C_{19}H_{20}N_4$ |
| 23 | 176–180, dec. | $C_{13}H_{13}Cl_3N_4$ |
| 24 | 159–161 | $C_{15}H_{20}N_4$ |
| 25 | 143–145 | $C_{12}H_{14}N_4$ |
| 26 | 200–203 | $C_{12}H_{13}ClN_4$ |
| 27 | 138–141 | $C_{18}H_{18}N_4$ |
| 28 | 218–222 | $C_{12}H_{11}Cl_3N_4$ |
| 29 | 146–149 | $C_{13}H_{16}N_4$ |
| 30 | 143–147 | $C_{15}H_{20}N_4O$ |
| 31 | 140–142 | $C_{13}H_{16}N_4$ |
| 32 | 151–154 | $C_{14}H_{18}N_4O$ |
| 33 | 128–133 | $C_{21}H_{24}N_4$ |
| 34 | 168–182 | $C_{15}H_{17}Cl_3N_4$ |
| 35 | 137–139 | $C_{16}H_{22}N_4$ |
| 36 | 130–132 | $C_{18}H_{26}N_4$ |
| 37 | 126–127 | $C_{14}H_{18}N_4$ |
| 38 | 158–163 | $C_{16}H_{19}Cl_3N_4$ |
| 39 | 255 | $C_{16}H_{20}Cl_4N_4$ |
| 40 | 149–153 | $C_{20}H_{22}N_4$ |
| 41 | 111–113 | $C_{15}H_{20}N_4$ |
| 42 | 120–122 | $C_{23}H_{28}N_4$ |
| 43 | 75–78 | $C_{25}H_{32}N_4$ |
| 44 | 99–102 | $C_{16}H_{22}N_4$ |
| 45 | 226–231 | $C_{15}H_{14}N_4$ |
| 46 | 181–183 | $C_{18}H_{20}N_4$ |
| 47 | 179–181 | $C_{17}H_{18}N_4$ |
| 48 | 181–183, dec. | $C_{17}H_{19}N_5$ |
| 49 | 92–95 | $C_{18}H_{20}N_4$ |
| 50 | — | $C_{19}H_{22}N_4$ |
| 51 | 105–110 | $C_{19}H_{22}N_4$ |
| 52 | 103–107 | $C_{21}H_{24}N_4O$ |
| 53 | 152–155 | $C_{18}H_{20}N_4$ |
| 54 | 128–133 | $C_{19}H_{22}N_4$ |
| 55 | 98–102 | $C_{20}H_{24}N_4$ |
| 56 | 173–174 | $C_{10}H_{18}N_4O$ |
| 57 | 103–107 | $C_{16}H_{30}N_4O$ |
| 58 | 195–198 | $C_9H_{13}N_5O$ |
| 59 | 173–175 | $C_{11}H_{10}F_2N_4O$ |
| 60 | 201–202 | $C_{11}H_9BrCl_2N_4O$ |
| 61 | 132–134 | $C_{18}H_{24}N_4O_3$ |
| 62 | 115–119 | $C_{12}H_{22}N_4$ |
| 63 | 226–230 | $C_{12}H_{23}ClN_4$ |
| 64 | — | $C_8H_{16}N_4Si$ |
| 65 | 158–161 | $C_{10}H_{20}N_4Si$ |
| 66 | 200–202 | $C_{11}H_{19}N_5O$ |
| 67 | 159–162 | $C_{14}H_{17}ClN_4$ |
| 68 | 243–245 | $C_{14}H_{18}Cl_2N_4$ |
| 69 | 128–132 | $C_{16}H_{22}N_4O$ |
| 70 | 124–126 | $C_{18}H_{26}N_4O$ |
| 71 | 223–226 | $C_{12}H_{12}ClN_5O_2$ |
| 72 | 134–136 | $C_{17}H_{24}ClN_5$ |
| 73 | 292–294, dec. | $C_{17}H_{27}Cl_4N_5$ |
| 74 | 102–112 | $C_{23}H_{36}ClN_5$ |
| 75 | 178–182 | $C_{17}H_{22}ClN_5$ |
| 76 | 327–329, dec. | $C_{17}H_{25}Cl_4N_5$ |
| 77 | 84–92 | $C_{19}H_{19}Cl_2N_5$ |
| 78 | 61–70 | $C_{22}H_{25}Cl_2N_5$ |
| 79 | 92–96 | $C_{23}H_{28}ClN_5O_3S$ |
| 80 | 177–180 | $C_{18}H_{19}ClN_6$ |
| 81 | 182–192 | $C_{18}H_{21}Cl_3N_6$ |
| 82 | 104–105 | $C_{17}H_{22}ClN_5O$ |
| 83 | 260–261 | $C_{17}H_{22}ClN_5O$ |
| 84 | 77–85 | $C_{22}H_{32}ClN_5O$ |
| 85 | 55–66 | $C_{23}H_{34}ClN_5O$ |
| 86 | 136–140 | $C_{16}H_{13}ClF_7N_5O$ |
| 87 | 217–225 | $C_{19}H_{17}Cl_2N_5O$ |
| 88 | 134–137 | $C_{22}H_{23}Cl_2N_5O$ |
| 89 | 104–120 | $C_{23}H_{26}ClN_5O_4S$ |
| 90 | 77–80 | $C_{11}H_{20}N_4O$ |
| 91 | 117–124 | $C_{17}H_{28}N_4O$ |
| 92 | 89–93 | $C_{16}H_{22}N_4OS$ |
| 93 | 165–172 | $C_{16}H_{22}N_4O_3S$ |
| 94 | 218 | $C_{16}H_{23}ClN_4O_3S$ |
| 95 | 107–111 | $C_{18}H_{26}N_4OS$ |
| 96 | 138–148 | $C_{18}H_{26}N_4O_3S$ |
| 97 | 173–174 | $C_{10}H_{18}N_4O$ |
| 98 | 198, dec. | $C_{13}H_{17}ClN_4O$ |
| 99 | 201–202 | $C_{11}H_9BrCl_2N_4O$ |
| 100 | 97–99 | $C_{23}H_{36}N_4O$ |
| 101 | GUM | $C_{17}H_{24}N_4O$ |
| 102 | 130–133 | $C_{16}H_{22}N_4O_2$ |
| 103 | 84–96 | $C_{16}H_{24}N_4OSi$ |
| 104 | 132–134 | $C_{18}H_{24}N_4O_3$ |
| 105 | GUM | $C_{19}H_{19}ClN_4O$ |
| 106 | GUM | $C_{23}H_{28}N_4O_2$ |
| 107 | 250 | $C_{19}H_{20}N_4O_2$ |
| 108 | GUM | $C_{23}H_{28}N_4O_4S$ |
| 109 | GUM | $C_{22}H_{30}N_4O_2$ |
| 110 | 254–258 | $C_{15}H_{22}N_4$ |
| 111 | 148–153 | $C_{14}H_{24}N_4$ |
| 112 | 244–246 | $C_{19}H_{18}Cl_2N_6O_2$ |
| 113 | 246–247 | $C_{20}H_{22}N_6O_3$ |
| 114 | 148–149 | $C_{14}H_{17}ClN_4$ |
| 115 | 192–196 | $C_{13}H_{13}Cl_3N_4$ |
| 116 | — | $C_{13}H_{14}Cl_4N_4$ |
| 117 | 215–218 | $C_{14}H_{15}Cl_3N_4$ |
| 118 | — | $C_{15}H_{18}Cl_4N_4$ |
| 119 | 126–131 | $C_{17}H_{21}Cl_3N_4$ |
| 120 | 151–158 | $C_{15}H_{17}F_3N_4$ |
| 121 | — | $C_{15}H_{17}F_3N_4$ |
| 122 | 185–186 | $C_{15}H_{17}F_3N_4$ |
| 123 | 213–215 | $C_{15}H_{20}N_4$ |
| 124 | — | $C_{15}H_{20}N_4$ |
| 125 | 210–213 | $C_{15}H_{20}N_4$ |
| 126 | 169–172 | $C_{16}H_{22}N_4$ |
| 127 | 173–176 | $C_{16}H_{22}N_4$ |
| 128 | 188–190 | $C_{17}H_{24}N_4$ |
| 129 | — | $C_{16}H_{22}N_4O$ |
| 130 | 113–115 | $C_{16}H_{22}N_4O$ |
| 131 | 109–111 | $C_{17}H_{24}N_4O$ |
| 132 | 142–143 | $C_{11}H_{20}N_4O$ |
| 133 | 139–144 | $C_{10}H_{16}N_4O$ |
| 134 | 160.5–161.5 | $C_{14}H_{18}N_4O$ |
| 135 | 132–134 | $C_{15}H_{17}F_3N_4O_2$ |
| 136 | 181–185 | $C_{14}H_{16}Cl_2N_4$ |
| 137 | 93–96 | $C_{17}H_{21}F_3N_4$ |
| 138 | 48–55 | $C_{17}H_{21}F_3N_4$ |
| 139 | 164–168 | $C_{15}H_{18}Cl_2N_4$ |
| 140 | 125–128 | $C_{15}H_{19}ClN_4$ |
| 141 | 163–166 | $C_{15}H_{18}Cl_2N_4$ |
| 142 | SOLID | $C_{15}H_{18}Cl_2N_4$ |
| 143 | 142–144 | $C_{15}H_{19}FN_4$ |
| 144 | 67–68 | $C_{22}H_{23}F_3N_4$ |
| 145 | 94–101 | $C_{16}H_{21}ClN_4$ |
| 146 | 197–201 DEC | $C_{16}H_{22}N_4O$ |
| 147 | 135–137 | $C_{17}H_{24}N_4O$ |
| 148 | 129–134 | $C_{22}H_{24}F_2N_4$ |
| 149 | 136–138 | $C_{19}H_{23}ClN_4O_2$ |
| 150 | 192.193 | $C_{25}H_{35}ClN_4O_2$ |
| 151 | SOLID | $C_{14}H_{17}FN_4$ |
| 152 | 181–184 DEC | $C_{14}H_{16}Cl_2N_4$ |
| 153 | 145–147 | $C_{16}H_{17}F_5N_4$ |
| 154 | 143–146 | $C_{18}H_{17}F_9N_4$ |
| 155 | 146–147 | $C_{15}H_{16}ClF_3N_4$ |
| 156 | 118–119 | $C_{15}H_{17}F_3N_4O$ |

TABLE 1-a-continued

MELTING POINT/EMPIRICAL FORMULA

| Compound Number | Melting Point (°C.) | Empirical Formula |
| --- | --- | --- |
| 157 | 172–174 | $C_{15}H_{20}N_4O$ |
| 158 | 117–121 | $C_{16}H_{22}N_4O$ |
| 159 | 148–150 | $C_{15}H_{20}N_4S$ |
| 160 | 82–85 | $C_{15}H_{20}N_4O_2S$ |
| 161 | 172–175 | $C_{15}H_{17}N_5$ |
| 162 | 168–170 | $C_{15}H_{17}N_5.C_3H_7NO$ |
| 163 | 237.5–238 | $C_{15}H_{19}N_5O$ |
| 164 | 170–172 | $C_{20}H_{21}FN_4$ |
| 165 | 148–151 DEC | $C_{15}H_{18}Cl_2N_4$ |
| 166 | 213–221 DEC | $C_{15}H_{19}ClN_4O$ |
| 167 | 166–171 | $C_{16}H_{21}ClN_4O$ |
| 168 | 236–240 | $C_{15}H_{20}N_4O$ |
| 169 | 174–176 | $C_{16}H_{22}N_4O$ |
| 170 | 142–147 | $C_{21}H_{22}F_2N_4$ |
| 171 | 140–143 | $C_{20}H_{22}ClN_5O$ |
| 172 | 135–136 | $C_{16}H_{19}F_3N_4O$ |
| 173 | 130–132 | $C_{16}H_{21}ClN_4$ |
| 174 | — | $C_{14}H_{17}Cl_3N_4$ |
| 175 | — | $C_{16}H_{22}Cl_2N_4O_3S$ |
| 176 | — | $C_{20}H_{28}Cl_2N_4O_7$ |
| 177 | — | $C_{51}H_{48}Cl_4N_8O_6$ |
| 178 | — | $C_{18}H_{20}Cl_2N_4O_4$ |
| 179 | — | $C_{20}H_{24}Cl_4N_4O_4$ |
| 180 | — | $C_{26}H_{36}Cl_2N_4O_8$ |

Insecticide Formulations In the normal use of the insecticidal pyrimidines of the present invention, they usually will not be employed free from admixture or dilution, but ordinarily will be used in a suitable formulated composition compatible with the method of application and comprising an insecticidally effective amount of the pyrimidine. The pyrimidines of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present pyrimidines may be applied, for example, as sprays, dusts, or granules to the area where pest control is desired, the type of application varying of course with the pest and the environment. Thus, the pyrimidines of this invention may be formulated as granules of large particle size, as powdery dusts, as wettable powders, as emulsifiable concentrates, as solutions, and the like. It will be understood that the insecticides themselves may be present as essentially pure compounds, or as mixtures of these pyrimidine compounds.

Granules may comprise porous or nonporous particles, such as attapulgite clay or sand, for example, which serve as carriers for the pyrimidines. The granule particles are relatively large, a diameter of about 400–2500 microns typically. The particles are either impregnated with the pyrimidine from solution or coated with the pyrimidine, adhesive sometimes, being employed. Granules generally contain 0.05–10%, preferably 0.5–5%, active ingredient as the insecticidally effective amount.

Dusts are admixtures of the pyrimidines with finely divided solids such as talc, attapulgite clay, kieselguhr, pyrophyllite, chalk, diatomaceous earths, calcium phosphates, calcium and magnesium carbonates, sulfur, flours, and other organic and inorganic solids which acts carriers for the insecticide. These finely divided solids have an average particle size of less than about 50 microns. A typical:dust formulation useful for controlling insects contains 1 part of 2,4-diamino-5-[3-(2,4,5-trichlorophenyl) propyl]-6ethylpyrimidine (Compound 34) and 99 parts of talc.

The pyrimidines of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% pyrimidine, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects contains 1.5 parts each of sodium lignosulfonate and sodium lauryl sulfate as wetting agents, 25 parts of Compound 52 (above), and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the pyrimidines with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylaryl sulfonates, including alcohols; polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal composition.

Other useful formulations include simple solutions of the active ingredient in a solvent in which it is completely soluble at the desired concentrations, such as acetone or other organic solvents.

As shown in the biological test methods below, the compounds of the present invention were tested in the laboratory as dimethylsulfoxide solutions incorporated into an artificial insect diet or as aqueous acetone or methanol solutions containing a small amount of octylphenoxypolyethoxyethanol surfactant for use as foliar sprays. An insecticidally effective amount of pyrimidine in an insecticidal composition diluted for application is normally in the range of about 0.001% to about 8% by weight. Many variations of spraying and dusting compositions known in the art may be used by substituting the pyrimidine of this invention into compositions known or apparent in the art.

The insecticidal compositions of this invention may be formulated with other active ingredients, including other insecticides, nematicides, acaricides, fungicides, plant growth regulators, fertilizers, etc. In using the compositions to control insects, it is only necessary that an insecticidally effective amount of pyrimidine be applied to the locus where control is desired. Such locus may, e.g., be the insects themselves, plants upon which the insects feed, or the insect habitat. When the locus is the soil, e.g., soil in which agricultural crops are or will be planted, the active compound may be applied to and optionally incorporated into the soil. For most applications, an insecticidally effective amount will be about 75 to 4000 g per hectare, preferably 150 g to 3000 g per hectare.

Biological Data: Tables 2, 3, and 4

The 5-substituted 2,4-diaminopyrimidines of the present invention were incorporated into an artificial diet for evaluation of insecticidal activity against the tobacco budworm (*Heliothis virescens* [Fabricius]). The results are reported on Tables 2, 3, and 4 below.

Stock solutions of test chemical in dimethylsulfoxide were prepared for each rate of application. The rates of application, expressed as the negative log of the molar concentration, and the corresponding concentrations of the stock solution prepared for each rate are shown below:

| Stock Solution | Rate of Application |
|---|---|
| 50 micromolar | 4 |
| 5 | 5 |
| 0.5 | 6 |
| 0.05 | 7 |
| 0.005 | 8 |

One hundred microliters of each of the stock solutions was manually stirred into 50 mL of a molten (65°–70° C.) wheat germ-based artificial diet. The 50 mL of molten diet containing the test chemical was poured evenly into twenty wells in the outer four rows of a twenty-five well, five row plastic tray. Each well in the tray was about 1 cm in depth, with an opening of 3 cm by 4 cm at the lip. Molten diet containing only dimethylsulfoxide at the levels used in the test chemical-treated diet was poured into the five wells in the third row of the tray. Each tray therefore contained one test chemical at a single rate of application, together with an untreated control.

Single second instar tobacco budworm larvae were placed in each well. The larvae were selected at a stage of growth at which they uniformly weigh about 5 mg each. Upon completion of infestation, a sheet of clear plastic was heat-sealed over the top of the tray using a common household flat iron. The trays were held at 25C at 60% relative humidity for five days in a growth chamber. Lighting was set at 14 hours of light and 10 hours of darkness.

After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($pI_{50}$) was determined by linear regression, when possible, for each test chemical. Where possible, the negative log of the concentration of the test chemical that provided 50% mortality ($pLC_{50}$) was also determined.

Generally, the compounds of the present invention inhibited the growth of tobacco budworm. The most efficacious compounds were 32, 34, 38, 37, 48, 50, and 56, 67, 71, 74, 97, 100, and 110°–140, with $pI_{50}$ values of greater than 5. Compounds 34, 110, 117, 118, 136–140, were the most active of these compounds with a $pI_{150}$ value of 6.4. All of the compounds exemplified above caused some insect mortality in this test. These data are presented in Table 2.

Certain 5-substituted-2,4-diaminopyrimidine derivatives with high $pI_{50}$ values from the diet test were tested for insecticidal activity in foliar evaluations against the tobacco budworm, beet armyworm (*Spodoptera exigua* Hubner]), and the cabbage looper (*Trichoplusia ni* [Hubner]).

In these tests against the tobacco budworm and the beet armyworm, nine-day-old chick pea plants (*Cicer arietinum*) were sprayed at 20 psi to runoff on both upper and lower leaf surfaces with solutions of test chemical to provide application rates as high as 1000 ppm of test chemical. The solvent used to prepare the solutions of test chemical was 10% acetone or methanol (v/v) and 0.1% of the surfactant octylphenoxypolyethoxyethanol in distilled water. Four replicates, each containing four chick pea plants, for each rate of application of test chemical were sprayed. The treated plants were transferred to a hood where they were kept until the spray had dried.

The four chick pea plants in each replicate treated with test chemical as described above were removed from their pots by cutting the stems just above the soil line. The excised leaves and stems from the four plants in each replicate were placed in individual 8-ounce paper cups, which contained a moistened filter paper. Five second-instar (4–5 days old) tobacco budworms or beet armyworms were counted into each cup, taking care not to cause injury. An opaque plastic lid was place on each cup, which was then held in a growth chamber for a 96 hour exposure period at 25° C. and 50% relative humidity. At the end of the 96 hour exposure period the cups were opened, and the numbers of dead and live insects were counted. Moribund larvae which were disoriented or unable to crawl normally were counted as dead. Using the insect counts, the efficacy of the test chemical was expressed in percent mortality. The condition of the test plants was also observed for phytotoxicity and for reduction of feeding damage as compared to an untreated control. Where applicable, computer-generated $LC_{50}$ values were determined from the percentages of insect mortality.

Foliar tests with cabbage looper were conducted in the same manner as described above, the difference being that pinto bean plants (*Phaseolus vulgaris*) were used.

Of the compounds evaluated on foliage for insecticidal activity, some of the more active ones were compounds 32, 34, 47, 50, 56, and more particularly, each of compounds 110–137 of Table 1. Of these, compound 34 was one of the most effective, providing excellent mortality of all three insect species in the foliar tests. These results are evident from the data in Table 3. Very good results with most of compounds 110–137, which also represent preferred species of this invention, are likewise evident from this table.

Table 4, presents a comparison of the Insect Growth Inhibitory (INH) $pI_{50}$ values from the diet test of certain compounds of the present invention with the percent mortality data for those same compounds in the foliar test. These data clearly Show that the compounds of the present invention with INH $pI_{50}$ values of about 5.0 or higher are the most insecticidally active in the foliar test. Compound 34, with an INH $pI_{50}$ value of 6.4, in the diet test provides excellent insect mortality in the foliar tests against tobacco budworm, beet armyworm, and especially cabbage looper. The results obtained in the diet test are, thus, an excellent indication of the potential insecticidal efficacy of a compound when tested on the foliage of plants.

The diet test as described herein when compared to a foliar test is a more precise means of testing compounds for insecticidal activity, and is not subject to environmental stresses that might be found in a greenhouse, growth chamber, or from the whole plant itself. The results obtained from the diet test are more reproducible than those from a foliar test, and are based on quantitative measurement rather than observations.

A number of synthetic pyrethroids with known insecticidal activity in foliar tests against the tobacco budworm were also tested in the diet test and were found to have INH $pI_{50}$ values of 6.6 or higher. These known synthetic pyrethroids are cypermethrin, permethrin, cyfluthrin, flucythrinate, and biphenthrin.

TABLE 2

INSECTICIDAL ACTIVITY OF 5-SUBSTITUTED-2,4-DIAMINOPYRIMIDINES INCORPORATED INTO THE DIET OF TOBACCO BUDWORM

| Cmpd No. | Rate of Application[1] | Percent Growth Inhibition[2,3,4] | pI50[5] | Percent Mortality[6] | pLC50[7] |
|---|---|---|---|---|---|
| 1 | 7 | ND | — | 0 | — |
|  | 6 | ND |  |  |  |
|  | 5 | ND |  | 0 |  |
|  | 4 | 10 |  | 0 |  |
|  | 3.5 | 8 |  | 0 |  |
| 2 | 4 | 6 | — | 0 | — |
| 3 | 4 | −4 | — | 0 | — |
| 4 | 8 | ND | — | 0 | — |
|  | 7 | ND |  |  |  |
|  | 6 | ND |  |  |  |
|  | 5 | −5 |  |  |  |
|  | 4 | 13 |  |  |  |
| 5 | 7 | ND | — | 0 | — |
|  | 6 | ND |  |  |  |
|  | 5 | ND |  |  |  |
|  | 4 | −7 |  |  |  |
|  | 3.5 | 18 |  |  |  |
| 6 | 8 | ND | 4.6 | 0 | — |
|  | 7 | ND |  | 0 |  |
|  | 6 | −11 |  | 0 |  |
|  | 5 | 25 |  | 0 |  |
|  | 4 | 83 |  | 0 |  |
| 7 | 7 | 6 | — | 0 | — |
|  | 6 | −1 |  | 0 |  |
|  | 5 | −42 |  | 0 |  |
|  | 4 | −12 |  | 5 |  |
|  | 3 | −22 |  | 5 |  |
| 9 | 7 | ND | 3.6 | 0 | — |
|  | 6 | ND |  | 0 |  |
|  | 5 | 2 |  | 0 |  |
|  | 4 | 29 |  | 5 |  |
|  | 3.5 | 53 |  | 5 |  |
| 10 | 7 | ND | ≦3.5 | 0 | — |
|  | 6 | ND |  | 0 |  |
|  | 5 | 11 |  | 0 |  |
|  | 4 | 11 |  | 5 |  |
|  | 3.5 | 38 |  | 15 |  |
| 11 | 8 | −20 | — | 5 | — |
|  | 7 | 9 |  | 10 |  |
|  | 6 | 3 |  | 5 |  |
|  | 5 | −5 |  | 0 |  |
|  | 4 | −5 |  | 0 |  |
| 12 | 8 | 11 | — | 0 | — |
|  | 7 | −5 |  | 0 |  |
|  | 6 | 22 |  | 0 |  |
|  | 5 | −3 |  | 0 |  |
|  | 4 | −8 |  | 0 |  |
| 13 | 8 | ND | 4.7 | 0 |  |
|  | 7 | −11 |  | 0 |  |
|  | 6 | 19 |  | 0 |  |
|  | 5 | 34 |  | 0 |  |
|  | 4 | 71 |  | 0 |  |
| 14 | 6 | 10 | 4.5 | 0 | — |
|  | 5 | 23 |  | 0 |  |
|  | 4 | 80 |  | 5 |  |
| 15 | 8 | 31 | 4.4 | 0 | — |
|  | 7 | 23 |  | 0 |  |
|  | 6 | 7 |  | 0 |  |
|  | 5 | 14 |  | 0 |  |
|  | 4 | 74 |  | 15 |  |
| 16 | 8 | ND | — | 0 | — |
|  | 7 | ND |  | 0 |  |
|  | 6 | ND |  | 0 |  |
|  | 5 | −1 |  | 0 |  |
|  | 4 | −3 |  | 0 |  |
| 17 | 8 | ND | <3.5 |  |  |
|  | 7 | 30 |  | 0 |  |
|  | 6 | 34 |  | 0 |  |
|  | 5 | 38 |  | 5 |  |
|  | 4 | 32 |  | 5 |  |
|  | 3.5 | 43 |  | 5 |  |
| 18 | 5 | 9 | — | 0 | — |
|  | 4 | 15 |  | 0 |  |
| 19 | 4 | −8 | — | 0 | — |
| 21 | 8 | 22 | 4.4 | 0 | — |
|  | 7 | 22 |  | 0 |  |
|  | 6 | 38 |  | 20 |  |
|  | 5 | 42 |  | 0 |  |
|  | 4 | 53 |  | 10 |  |
|  | 3.5 | 58 |  | 10 |  |
| 22 | 8 | 21 | 4.3 | 0 | — |
|  | 7 | 25 |  | 0 |  |
|  | 6 | 25 |  | 0 |  |
|  | 5 | 12 |  | 0 |  |
|  | 4 | 70 |  | 15 |  |
|  | 8 | ND | — | ND | — |
|  | 7 | ND |  | ND |  |
|  | 6 | −28 |  | 0 |  |
|  | 5 | −14 |  | 0 |  |
|  | 4 | −11 |  | 0 |  |
| 23 | 8 | −16 | <4.0 |  |  |
|  | 7 | −20 |  | 0 |  |
|  | 6 | −15 |  | 0 |  |
|  | 5 | 4 |  | 0 |  |
|  | 4 | 42 |  | 20 |  |
| 24 | 7 | ND | 3.6 | 0 | — |
|  | 6 | 10 |  | 0 |  |
|  | 5 | 22 |  | 0 |  |
|  | 4 | 33 |  | 5 |  |
|  | 3.5 | 52 |  | 10 |  |
| 25 | 8 | ND | — | 0 | — |
|  | 7 | ND |  | 0 |  |
|  | 6 | ND |  | 0 |  |
|  | 5 | −15 |  | 0 |  |
|  | 4 | 16 |  | 0 |  |
| 26 | 5 | −10 | <4.0 | 0 |  |
|  | 4 | 27 |  | 0 |  |
| 27 | 8 | 5 | 4.8 | 0 | — |
|  | 7 | 17 |  | 0 |  |
|  | 6 | 25 |  | 0 |  |
|  | 5 | 38 |  | 0 |  |
|  | 4 | 70 |  | 10 |  |
| 28 | 8 | ND | <4.0 | 0 |  |
|  | 7 | ND |  | 0 |  |
|  | 6 | trace |  | 0 |  |
|  | 5 | 4 |  | 0 |  |
|  | 4 | 39 |  | 0 |  |
| 29 | 8 | ND | <3.5 | 0 |  |
|  | 7 | ND |  | 0 |  |
|  | 6 | 17 |  | 0 |  |
|  | 5 | 10 |  | 0 |  |
|  | 4 | 31 |  | 0 |  |
|  | 3.5 | 29 |  | 0 |  |
| 31 | 8 | ND | 4.8 | 0 | — |
|  | 7 | 6 |  | 0 |  |
|  | 6 | 19 |  | 0 |  |
|  | 5 | 39 |  | 0 |  |
|  | 4 | 74 |  | 0 |  |
| 32 | 7 | 16 | 5.2 | 0 | 3.8 |
|  | 6 | 15 |  | 5 |  |

TABLE 2-continued

INSECTICIDAL ACTIVITY OF 5-SUBSTITUTED-2,4-DIAMINOPYRIMIDINES INCORPORATED INTO THE DIET OF TOBACCO BUDWORM

| Cmpd No. | Rate of Application[1] | Percent Growth Inhibition[2,3,4] | pI50[5] | Percent Mortality[6] | pLC$_{50}$[7] |
|---|---|---|---|---|---|
|  | 5 | 66 |  | 25 |  |
|  | 4 | 94 |  | 45 |  |
|  | 3.5 | 97 |  | 55 |  |
| 33 | 8 | 13 | 6.3 | 0 |  |
|  | 7 | 29 |  | 0 |  |
|  | 6 | 39 |  | 5 |  |
|  | 5 | 93 |  | 0 |  |
|  | 4 | 97 |  | 45 |  |
| 34 | 8 | 10 | 6.4 | 0 | 5.7 |
|  | 7 | −2 |  | 0 |  |
|  | 6 | 89 |  | 30 |  |
|  | 5 | 95 |  | 85 |  |
|  | 4 | 100 |  | 85 |  |
| 35 | 8 | 35 | 4.6 | 0 | — |
|  | 7 | 13 |  | 0 |  |
|  | 6 | 20 |  | 0 |  |
|  | 5 | 34 |  | 0 |  |
|  | 4 | 73 |  | 5 |  |
| 36 | 7 | 3 | 3.6 | 0 | — |
|  | 6 | 9 |  | 5 |  |
|  | 5 | 9 |  | 10 |  |
|  | 4 | 25 |  | 15 |  |
|  | 3 | 85 |  | 10 |  |
| 37 | 8 | ND | 5.1 | 0 | — |
|  | 7 | −29 |  | 0 |  |
|  | 6 | 38 |  | 0 |  |
|  | 5 | 42 |  | 0 |  |
|  | 4 | 76 |  | 0 |  |
| 38 | 6 | −4 | 4.9 | 0 | — |
|  | 5 | 56 |  | 0 |  |
|  | 4 | 88 |  | 0 |  |
|  | 8 | 15 | 5.9 | 0 | — |
|  | 7 | 21 |  | 0 |  |
|  | 6 | 34 |  | 0 |  |
|  | 5 | 71 |  | 0 |  |
|  | 4 | 93 |  | 15 |  |
| 39 | 6 | 9 | 5.1 | 0 | — |
|  | 5 | 63 |  | 0 |  |
|  | 4 | 91 |  | 20 |  |
| 40 | 8 | 4 | — | 0 | — |
|  | 7 | 4 |  | 0 |  |
|  | 6 | 20 |  | 5 |  |
|  | 5 | 2 |  | 5 |  |
|  | 4 | 18 |  | 0 |  |
| 41 | 8 | ND | 4.7 | 0 | — |
|  | 7 | ND |  | 0 |  |
|  | 6 | 1 |  | 0 |  |
|  | 5 | 39 |  | 0 |  |
|  | 4 | 73 |  | 0 |  |
| 42 | 8 | 4 | — | 0 | — |
|  | 7 | 11 |  | 0 |  |
|  | 6 | 15 |  | 5 |  |
|  | 5 | −4 |  | 5 |  |
|  | 4 | −14 |  | 5 |  |
| 43 | 8 | −8 | 5.1 | 0 | — |
|  | 7 | 2 |  | 0 |  |
|  | 6 | 12 |  | 5 |  |
|  | 5 | 54 |  | 0 |  |
|  | 4 | ND |  | ND |  |
|  | 8 | 58 | — | 0 | — |
|  | 7 | 35 |  | 5 |  |
|  | 6 | 32 |  | 5 |  |
|  | 5 | 49 |  | 5 |  |
|  | 4 | 33 |  | 5 |  |
|  | 8 | 38 | — | 0 | — |
|  | 7 | 43 |  | 0 |  |
|  | 6 | 23 |  | 0 |  |
|  | 5 | 34 |  | 5 |  |
|  | 4 |  |  | 5 |  |
|  | 7 | 30 | 3.0 | 0 |  |
|  | 6 | 16 |  | 0 |  |
|  | 5 | 1 |  | 0 |  |
|  | 4 | 26 |  | 0 |  |
|  | 3 | 51 |  | 0 |  |
| 44 | 8 | ND | 4.9 | 0 | — |
|  | 7 | 1 |  | 0 |  |
|  | 6 | 15 |  | 0 |  |
|  | 5 | 41 |  | 0 |  |
|  | 4 | 80 |  | 15 |  |
| 45 | 8 | 19 | 3.6 | 0 | — |
|  | 7 | 14 |  | 0 |  |
|  | 6 | 24 |  | 10 |  |
|  | 5 | 35 |  | 5 |  |
|  | 4 | 42 |  | 5 |  |
|  | 3.5 | 54 |  | 5 |  |
| 46 | 8 | 11 | <4.0 | 0 |  |
|  | 7 | 0 |  | 0 |  |
|  | 6 | −7 |  | 0 |  |
|  | 5 | −2 |  | 0 |  |
|  | 4 | 42 |  | 0 |  |
| 47 | 8 | 6 | 5.9 | 0 | <4.0 |
|  | 7 | −17 |  | 0 |  |
|  | 6 | 66 |  | 5 |  |
|  | 5 | 90 |  | 20 |  |
|  | 4 | 95 |  | 30 |  |
|  | 8 | 10 | 6.1 | 0 | 4.1 |
|  | 7 | 22 |  | 0 |  |
|  | 6 | 50 |  | 5 |  |
|  | 5 | 76 |  | 15 |  |
|  | 4 | 98 |  | 60 |  |
|  | 3.5 | 98 |  | 70 |  |
| 48 | 8 | 2 | 6.0 | 0 | 4.4 |
|  | 7 | 10 |  | 0 |  |
|  | 6 | 60 |  | 10 |  |
|  | 5 | 85 |  | 20 |  |
|  | 4 | 98 |  | 70 |  |
| 49 | 8 | 7 | 4.5 | 0 | — |
|  | 7 | −22 |  | 0 |  |
|  | 6 | −16 |  | 0 |  |
|  | 5 | 20 |  | 0 |  |
|  | 4 | 84 |  | 15 |  |
| 50 | 8 | 21 | 6.0 | 0 | <4.0 |
|  | 7 | 23 |  | 0 |  |
|  | 6 | 37 |  | 5 |  |
|  | 5 | 75 |  | 5 |  |
|  | 4 | 94 |  | 30 |  |
| 51 | 8 | −29 | 4.9 | 0 | — |
|  | 7 | 12 |  | 5 |  |
|  | 6 | 14 |  | 0 |  |
|  | 5 | 30 |  | 5 |  |
|  | 4 | 88 |  | 15 |  |
| 52 | 8 | ND | — | 0 | — |
|  | 7 | ND |  | 0 |  |
|  | 6 | ND |  | 0 |  |
|  | 5 | −2 |  | 0 |  |
|  | 4 | 20 |  | 0 |  |
| 53 | 8 | ND | 4.9 | 0 | — |
|  | 7 | ND |  | 0 |  |
|  | 6 | 4 |  | 0 |  |
|  | 5 | 50 |  | 0 |  |
|  | 4 | 80 |  | 0 |  |
| 54 | 6 | 6 | 5.4 | 0 | <4.0 |
|  | 5 | 82 |  | 20 |  |
|  | 4 | 98 |  | 40 |  |
|  | 8 | −1 | 5.7 | 0 | — |
|  | 7 | 22 |  | 0 |  |
|  | 6 | 33 |  | 0 |  |
|  | 5 | 73 |  | 0 |  |
|  | 4 | 92 |  | 15 |  |
| 55 | 6 | 4 | 4.9 | 0 | — |
|  | 5 | 59 |  | 0 |  |
|  | 4 | 89 |  | 5 |  |

TABLE 2-continued

INSECTICIDAL ACTIVITY OF 5-SUBSTITUTED-2,4-DIAMINOPYRIMIDINES INCORPORATED INTO THE DIET OF TOBACCO BUDWORM

| Cmpd No. | Rate of Application[1] | Percent Growth Inhibition[2,3,4] | pI50[5] | Percent Mortality[6] | pLC$_{50}$[7] |
|---|---|---|---|---|---|
| 56 | 8 | −7 | 5.7 | 0 | — |
|  | 7 | −19 |  | 0 |  |
|  | 6 | 33 |  | 0 |  |
|  | 5 | 83 |  | 15 |  |
|  | 4 | 91 |  | 20 |  |
| 57 | 6 | −3 | 4.3 | 0 | — |
|  | 5 | 18 |  | 0 |  |
|  | 4 | 62 |  | 0 |  |
| 58 | 4 | 3 | — | 0 | — |
| 59 | 5 | 18 | 4.2 | 0 | — |
|  | 4 | 57 |  |  |  |
| 60 | 6 | −1 | 4.3 | 0 | — |
|  | 5 | 15 |  | 0 |  |
|  | 4 | 66 |  | 0 |  |
| 61 | 6 | −24 | 4.4 | 0 | — |
|  | 5 | 10 |  | 0 |  |
|  | 4 | 79 |  | 10 |  |
| 62 | 5 | 4 | 4.3 | 0 | — |
|  | 4 | 71 |  | 0 |  |
| 63 | 6 | 8 | 4.2 | 0 | — |
|  | 5 | 18 |  | 0 |  |
|  | 4 | 60 |  | 0 |  |
| 64 | 5 | −7 | — | 0 | — |
|  | 4 | 13 |  | 0 |  |
| 65 | 5 | 1 | 4.3 | 0 | — |
|  | 4 | 72 |  | 5 |  |
| 66 | 5 | −8 | — | 0 | — |
|  | 4 | 11 |  | 0 |  |
| 67 | 7 | 13 | 5.9 | 0 | <4.0 |
|  | 6 | 40 |  | 0 |  |
|  | 5 | 83 |  | 10 |  |
|  | 4 | 95 |  | 25 |  |
| 69 | 5 | −5 | 4.1 | 0 | — |
|  | 4 | 56 |  | 0 |  |
| 70 | 5 | 1 | — | 0 | — |
|  | 4 | 13 |  | 0 |  |
| 71 | 7 | 13 | 4.9 | 0 | <4.0 |
|  | 6 | 9 |  | 0 |  |
|  | 5 | 28 |  | 0 |  |
|  | 4 | 93 |  | 30 |  |
|  | 7 | 20 | 5.6 | 0 | — |
|  | 6 | 43 |  | 0 |  |
|  | 5 | 54 |  | 0 |  |
|  | 4 | 90 |  | 15 |  |
| 72 | 5 | 26 | <4.0 | 0 | — |
|  | 4 | 29 |  | 0 |  |
| 74 | 6 | 8 | 5.1 | 0 | <4.0 |
|  | 5 | 67 |  | 0 |  |
|  | 4 | 95 |  | 30 |  |
| 75 | 4 | TRACE | — | 0 | — |
| 77 | 5 | −10 | <4.0 | 0 | — |
|  | 4 | 28 |  | 0 |  |
| 78 | 6 | 24 | 4.0 | 0 | — |
|  | 5 | 19 |  | 0 |  |
|  | 4 | 48 |  | 0 |  |
| 79 | 6 | 4 | 4.9 | 0 | — |
|  | 5 | 49 |  | 0 |  |
|  | 4 | 83 |  | 10 |  |
| 80 | 5 | −4 | >4.0 | 0 | — |
|  | 4 | 31 |  | 0 |  |
| 82 | 4 | 1 | — | 0 | — |
| 83 | 4 | −15 | — | 0 | — |
| 84 | 5 | 3 | — | 0 | — |
|  | 4 | 2 |  | 0 |  |
| 85 | 5 | −1 | <4.0 | 0 | — |
|  | 4 | 21 |  | 0 |  |
| 86 | 5 | −5 | — | 0 | — |
|  | 4 | 12 |  | 0 |  |
| 87 | 4 | 12 | — | 0 | — |
| 88 | 5 | 26 | <4.0 | 0 | — |
|  | 4 | 35 |  | 0 |  |
| 90 | 5 | 3 | — | 0 | — |
|  | 4 | 1 |  | 0 |  |
| 91 | 4 | 2 | — | 0 | — |
| 92 | 6 | −7 | 4.7 | 0 | — |
|  | 5 | 23 |  | 0 |  |
|  | 4 | 86 |  | 0 |  |
| 93 | 4 | 14 | — | 0 | — |
| 96 | 5 | 16 | 4.4 | 0 | — |
|  | 4 | 74 |  | 0 |  |
| 97 | 8 | −7 | 5.7 | 0 | — |
|  | 7 | −19 |  | 0 |  |
|  | 6 | 33 |  | 0 |  |
|  | 5 | 83 |  | 15 |  |
|  | 4 | 91 |  | 20 |  |
| 98 | 6 | 10 | 4.7 | 0 | — |
|  | 5 | 33 |  | 0 |  |
|  | 4 | 76 |  | 10 |  |
| 99 | 6 | −1 | 4.3 | 0 | — |
|  | 5 | 15 |  | 0 |  |
|  | 4 | 66 |  | 0 |  |
| 100 | 7 | −14 | 5.0 | 0 | — |
|  | 6 | 24 |  | 0 |  |
|  | 5 | 37 |  | 0 |  |
|  | 4 | 88 |  | 5 |  |
| 101 | 4 | −7 | — | 0 | — |
| 102 | 5 | 12 | 4.1 | 0 | — |
|  | 4 | 52 |  | 0 |  |
| 103 | 6 | −16 | — | 0 | — |
|  | 5 | 7 |  | 0 |  |
|  | 4 | 18 |  | 0 |  |
| 104 | 6 | −24 | 4.4 | 0 | — |
|  | 5 | 10 |  | 0 |  |
|  | 4 | 79 |  | 10 |  |
| 105 | 4 | −8 | — | 0 | — |
| 106 | 5 | 9 | <4.0 | 0 | — |
|  | 4 | 22 |  | 20 |  |
| 107 | 4 | 8 | — | 0 | — |
| 108 | 6 | 13 | 4.9 | 0 | — |
|  | 5 | 46 |  | 0 |  |
|  | 4 | 83 |  | 0 |  |
| 109 | 4 | −23 | — | 0 | — |
| 110 | 7 | 27 | 6.6 | 0 | — |
|  | 6 | 88 |  | 15 |  |
|  | 5 | 96 |  | 35 |  |
|  | 4 | 100 |  | 95 |  |
| 111 | 6 | 35 | 5.3 | 0 | — |
|  | 5 | 60 |  | 0 |  |
|  | 4 | 75 |  | 0 |  |
| 112 | 8 | 23 | 5.6 | 0 | <4.0 |
|  | 7 | 10 |  | 0 |  |
|  | 6 | 31 |  | 0 |  |
|  | 5 | 76 |  | 5 |  |
|  | 4 | 90 |  | 25 |  |
| 113 | 8 | 2 | 5.1 | 0 | — |
|  | 7 | 25 |  | 0 |  |
|  | 6 | 14 |  | 0 |  |
|  | 5 | 66 |  | 5 |  |
|  | 4 | 82 |  | 15 |  |
| 114 | 7 | 9 | 5.8 | 0 | 4.4 |
|  | 6 | 35 |  | 5 |  |
|  | 5 | 84 |  | 10 |  |
|  | 4 | 98 |  | 80 |  |
| 115 | 6 | 9 | 5.3 | 0 | <4.0 |
|  | 5 | 63 |  | 15 |  |
|  | 4 | 97 |  | 35 |  |
| 116 | 6 | 16 | 5.3 | 0 | — |
|  | 5 | 79 |  | 5 |  |
|  | 4 | 95 |  | 20 |  |
| 117 | 7 | 16 | 6.6 | 0 | 5.5 |
|  | 6 | 92 |  | 35 |  |
|  | 5 | 98 |  | 65 |  |

TABLE 2-continued

INSECTICIDAL ACTIVITY OF 5-SUBSTITUTED-2,4-DIAMINOPYRIMIDINES INCORPORATED INTO THE DIET OF TOBACCO BUDWORM

| Cmpd No. | Rate of Application[1] | Percent Growth Inhibition[2,3,4] | pI50[5] | Percent Mortality[6] | pLC$_{50}$[7] |
|---|---|---|---|---|---|
|  | 4 | 99 |  | 70 |  |
| 118 | 7 | 17 | 6.5 | 0 | 4.8 |
|  | 6 | 88 |  | 15 |  |
|  | 5 | 97 |  | 55 |  |
|  | 4 | 99 |  | 65 |  |
| 119 | 7 | 8 | 5.0 | 0 | — |
|  | 6 | 7 |  | 0 |  |
|  | 5 | 59 |  | 0 |  |
|  | 4 | 85 |  | 10 |  |
| 120 | 7 | 11 | 5.9 | 0 | <4.0 |
|  | 6 | 45 |  | 5 |  |
|  | 5 | 84 |  | 10 |  |
|  | 4 | 96 |  | 30 |  |
| 121 | 6 | 9 | 5.2 | 0 | <4.0 |
|  | 5 | 73 |  | 5 |  |
|  | 4 | 94 |  | 25 |  |
| 122 | 7 | 29 | 5.4 | 0 | <4.0 |
|  | 6 | 23 |  | 0 |  |
|  | 5 | 75 |  | 5 |  |
|  | 4 | 96 |  | 40 |  |
| 123 | 7 | −13 | 5.8 | 0 | — |
|  | 6 | 48 |  | 0 |  |
|  | 5 | 88 |  | 20 |  |
|  | 4 | 94 |  | 10 |  |
| 124 | 6 | 13 | 5.2 | 0 | <4.0 |
|  | 5 | 63 |  | 15 |  |
|  | 4 | 97 |  | 35 |  |
| 125 | 7 | −14 | 5.7 | 0 | <4.0 |
|  | 6 | 41 |  | 0 |  |
|  | 5 | 85 |  | 10 |  |
|  | 4 | 95 |  | 30 |  |
| 126 | 6 | 16 | 5.3 | 0 | <4.0 |
|  | 5 | 79 |  | 0 |  |
|  | 4 | 97 |  | 30 |  |
| 127 | 6 | 25 | 5.6 | 0 | — |
|  | 5 | 84 |  | 0 |  |
|  | 4 | 93 |  | 5 |  |
| 128 | 7 | 7 | 5.9 | 0 | — |
|  | 6 | 47 |  | 0 |  |
|  | 5 | 89 |  | 25 |  |
|  | 4 | 95 |  | 20 |  |
| 129 | 6 | −6 | 5.1 | 0 | — |
|  | 5 | 78 |  | 5 |  |
|  | 4 | 92 |  | 10 |  |
| 130 | 6 | 7 | 5.2 | 0 | — |
|  | 5 | 76 |  | 5 |  |
|  | 4 | 94 |  | 15 |  |
| 131 | 6 | 9 | 5.5 | 0 | — |
|  | 5 | 86 |  | 20 |  |
|  | 4 | 94 |  | 25 |  |
| 132 | 7 | 29 | 6.3 | 0 | — |
|  | 6 | 55 |  | 0 |  |
|  | 5 | 91 |  | 0 |  |
|  | 4 | 96 |  | 5 |  |
| 133 | 6 | 18 | 5.0 | 0 | — |
|  | 5 | 53 |  | 0 |  |
|  | 4 | 83 |  | 5 |  |
| 134 | 6 | 16 | 5.5 | 0 | — |
|  | 5 | 84 |  | 0 |  |
|  | 4 | 93 |  | 0 |  |
|  | 7 | 9 | 5.9 | 0 | — |
|  | 6 | 43 |  | 0 |  |
|  | 5 | 84 |  | 5 |  |
|  | 4 | 92 |  | 15 |  |
| 135 | 7 | 10 | 6.2 | 0 | <4.0 |
|  | 6 | 72 |  | 0 |  |
|  | 5 | 91 |  | 20 |  |
|  | 4 | 93 |  | 25 |  |
| 136 | 8 | 20 | 7.0 | 0 | 4.7 |
|  | 7 | 45 |  | 0 |  |
|  | 6 | 88 |  | 20 |  |
|  | 5 | 97 |  | 40 |  |
|  | 4 | 99 |  | 70 |  |
|  | 8 | 14 | 7.0 | 0 | 4.8 |
|  | 7 | 47 |  | 0 |  |
|  | 6 | 89 |  | 20 |  |
|  | 5 | 98 |  | 35 |  |
|  | 4 | 100 |  | 80 |  |
| 137 | 7 | −1 | 6.4 | 0 | 4.4 |
|  | 6 | 80 |  | 10 |  |
|  | 5 | 95 |  | 25 |  |
|  | 4 | 98 |  | 65 |  |
| 138 | 8 | −5 | 6.4 | 0 | 5.1 |
|  | 7 | 34 |  | 0 |  |
|  | 6 | 58 |  | 5 |  |
|  | 5 | 94 |  | 55 |  |
|  | 4 | 96 |  | 60 |  |
| 139 | 7 | 19 | 6.5 | 0 | <4.0 |
|  | 6 | 83 |  | 0 |  |
|  | 5 | 94 |  | 10 |  |
|  | 4 | 96 |  | 35 |  |
|  | 8 | 6 | 6.7 | 0 | 4.4 |
|  | 7 | 21 |  | 5 |  |
|  | 6 | 83 |  | 15 |  |
|  | 5 | 95 |  | 25 |  |
|  | 4 | 99 |  | 70 |  |
| 140 | 8 | 5 | 6.7 | 0 | 4.5 |
|  | 7 | 27 |  | 0 |  |
|  | 6 | 83 |  | 10 |  |
|  | 5 | 93 |  | 10 |  |
|  | 4 | 100 |  | 95 |  |
|  | 8 | 1 | 6.7 | 0 | 4.6 |
|  | 7 | 24 |  | 0 |  |
|  | 6 | 82 |  | 10 |  |
|  | 5 | 96 |  | 30 |  |
|  | 4 | 99 |  | 70 |  |
| 141 | 8 | 23 | 7.1 | 0 | 4.9 |
|  | 7 | 45 |  | 0 |  |
|  | 6 | 88 |  | 15 |  |
|  | 5 | 96 |  | 35 |  |
|  | 4 | 100 |  | 90 |  |
| 142 | 7 | 6 | 5.4 | 0 | <4.0 |
|  | 6 | 23 |  | 0 |  |
|  | 5 | 73 |  | 0 |  |
|  | 4 | 91 |  | 30 |  |
| 143 | 7 | −2 | 6.0 | 0 | 4.5 |
|  | 6 | 59 |  | 0 |  |
|  | 5 | 92 |  | 30 |  |
|  | 4 | 99 |  | 70 |  |
| 144 | 7 | 32 | 6.5 | 0 | 4.0 |
|  | 6 | 72 |  | 5 |  |
|  | 5 | 92 |  | 20 |  |
|  | 4 | 97 |  | 50 |  |
| 145 | 7 | −13 | 5.6 | 0 | — |
|  | 6 | 24 |  | 0 |  |
|  | 5 | 80 |  | 15 |  |
|  | 4 | 95 |  | 20 |  |
| 146 | 5 | 4 | 4.4 | 0 | — |
|  | 4 | 76 |  | 15 |  |
| 147 | 6 | −5 | 4.8 | 0 | — |
|  | 5 | 35 |  | 10 |  |
|  | 4 | 86 |  | 20 |  |
| 148 | 6 | 1 | 5.1 | 0 | — |
|  | 5 | 67 |  | 10 |  |
|  | 4 | 94 |  | 20 |  |
| 149 | 6 | 78 | >6.0 | 0 | <4.0 |
|  | 5 | 95 |  | 15 |  |
|  | 4 | 98 |  | 30 |  |
|  | 8 | 22 | 7.0 | 0 | 4.0 |
|  | 7 | 42 |  | 0 |  |
|  | 6 | 84 |  | 5 |  |
|  | 5 | 94 |  | 20 |  |

TABLE 2-continued

INSECTICIDAL ACTIVITY OF 5-SUBSTITUTED-2,4-DIAMINOPYRIMIDINES INCORPORATED INTO THE DIET OF TOBACCO BUDWORM

| Cmpd No. | Rate of Application[1] | Percent Growth Inhibition[2,3,4] | pI50[5] | Percent Mortality[6] | pLC$_{50}$[7] |
|---|---|---|---|---|---|
| | 4 | 97 | | 50 | |
| 150 | 6 | 11 | 5.2 | 0 | 4.5 |
| | 5 | 74 | | 15 | |
| | 4 | 99 | | 85 | |
| 151 | 6 | 76 | >6.0 | 0 | <4.0 |
| | 5 | 88 | | 5 | |
| | 4 | 95 | | 35 | |
| | 7 | −6 | 5.4 | 0 | — |
| | 6 | 12 | | 0 | |
| | 5 | 72 | | 10 | |
| | 4 | 75 | | 10 | |
| | 7 | −11 | 5.2 | 0 | — |
| | 6 | 13 | | 0 | |
| | 5 | 77 | | 15 | |
| | 4 | 90 | | 15 | |
| 152 | 7 | 11 | 6.0 | 0 | 4.6 |
| | 6 | 45 | | 0 | |
| | 5 | 93 | | 25 | |
| | 4 | 98 | | 75 | |
| 153 | 6 | 35 | 5.2 | 0 | — |
| | 5 | 50 | | 0 | |
| | 4 | 82 | | 15 | |
| 154 | 6 | 14 | 4.9 | 0 | — |
| | 5 | 47 | | 0 | |
| | 4 | 83 | | 10 | |
| 155 | 7 | 9 | 6.4 | 0 | <4.0 |
| | 6 | 83 | | 20 | |
| | 5 | 98 | | 35 | |
| | 4 | 99 | | 45 | |
| 156 | 6 | 2 | 5.1 | 0 | — |
| | 5 | 71 | | 10 | |
| | 4 | 95 | | 15 | |
| 157 | 7 | 11 | 6.0 | 0 | — |
| | 6 | 54 | | 0 | |
| | 5 | 83 | | 0 | |
| | 4 | 94 | | 15 | |
| 158 | 6 | 10 | 5.1 | 0 | <4.0 |
| | 5 | 68 | | 0 | |
| | 4 | 90 | | 25 | |
| 159 | 7 | 17 | 5.9 | 0 | <4.0 |
| | 6 | 41 | | 0 | |
| | 5 | 83 | | 0 | |
| | 4 | 97 | | 30 | |
| 160 | 6 | −1 | 4.9 | 0 | <4.0 |
| | 5 | 43 | | 5 | |
| | 4 | 88 | | 35 | |
| 161 | 5 | 1 | 4.4 | 0 | — |
| | 4 | 85 | | 0 | |
| 162 | 7 | −5 | 5.7 | 0 | — |
| | 6 | 29 | | 0 | |
| | 5 | 83 | | 0 | |
| | 4 | 94 | | 0 | |
| 163 | 6 | 23 | 5.6 | 0 | — |
| | 5 | 84 | | 15 | |
| | 4 | 95 | | 15 | |
| 164 | 7 | 9 | 5.5 | 0 | 4.4 |
| | 6 | 23 | | 0 | |
| | 5 | 81 | | 30 | |
| | 4 | 97 | | 65 | |
| 165 | 7 | 10 | 6.1 | 0 | <4.0 |
| | 6 | 60 | | 5 | |
| | 5 | 86 | | 30 | |
| | 4 | 96 | | 40 | |
| 166 | 5 | −2 | 4.2 | 0 | — |
| | 4 | 64 | | 0 | |
| 167 | 7 | 8 | 5.7 | 0 | — |
| | 6 | 26 | | 0 | |
| | 5 | 82 | | 5 | |
| | 4 | 94 | | 5 | |
| 168 | 6 | 9 | 4.8 | 0 | <4.0 |
| | 5 | 34 | | 5 | |
| | 4 | 80 | | 30 | |
| 169 | 7 | 11 | 5.7 | 0 | — |
| | 6 | 37 | | 0 | |
| | 5 | 79 | | 0 | |
| | 4 | 92 | | 0 | |
| 170 | 7 | 11 | 6.1 | 0 | <4.0 |
| | 6 | 57 | | 5 | |
| | 5 | 92 | | 25 | |
| | 4 | 97 | | 35 | |
| 171 | 7 | 3 | 6.1 | 0 | — |
| | 6 | 65 | | 0 | |
| | 5 | 79 | | 5 | |
| | 4.5 | 86 | | 10 | |
| 172 | 6 | 13 | 5.2 | 0 | — |
| | 5 | 64 | | 0 | |
| | 4 | 93 | | 5 | |

FOOTNOTES

[1]The rate of application is expressed as the negative log of the molar concentration of the test compound in the diet.
[2]Percent growth inhibition is derived from the total weight of the insects (IW) at each rate of application in the test relative to the total weight of insects in an untreated control,
% Gr. Inh. = [IW (control) − IW (test)/IW (control)] × 100
[3]ND = No data
[4]A minus % growth inhibition indicates that the insects weighed more at the termination of the test than those in the untreated control.
[5]pI50 is the negative log of the concentration of the test chemical that provides 50% growth inhibition in the test insects.
[6]Percent mortality is derived from the number of dead insects (TD) relative to the total number of insects (TI) used in the test, $$\% \text{ Mortality} = \frac{TD}{TI} \times 100$$

[7]pLC$_{50}$ is the negative log of the concentration of the test chemical that provides 50% mortality of the test insects.

TABLE 3

INSECTICIDAL ACTIVITY OF 5-SUBSTITUTED-2,4-DIAMINOPYRIMIDINES APPLIED AS FOLIAR SPRAYS

| Cmpd No. | Rate of Application (ppm) | Percent Mortality[1] | | |
|---|---|---|---|---|
| | | TBW | BAW | CL |
| 14 | 1000 | 50 | | |
| | 300 | 26 | | |
| | 100 | 5 | | |
| | 30 | 5 | | |
| | 10 | 5 | | |
| 17 | 300 | 0 | | |
| | 100 | 0 | | |
| | 30 | 0 | | |
| | 10 | 0 | | |
| | 3 | 0 | | |
| 21 | 1000 | 10 | | |
| 32 | 1000 | 100 | | |
| | 300 | 85 | | |
| | 100 | 70 | | |
| | 30 | 20 | | |
| | 10 | 0 | | |
| 34 | 1000 | 100 (100)[2] | | |
| | 300 | 100 | 95 (100) | 100 |
| | 100 | 100 | 90 (95) | 95 (100) |
| | 30 | 90 | 15 (50) | 80 (100) |
| | 10 | 60 | 10 (5) | 80 (75) |
| | 3 | 15 | | 60 (55) |
| | 1 | | | (10) |

TABLE 3-continued

INSECTICIDAL ACTIVITY OF 5-SUBSTITUTED-2,
4-DIAMINOPYRIMIDINES APPLIED AS FOLIAR SPRAYS

| Cmpd No. | Rate of Application (ppm) | Percent Mortality[1] TBW | BAW | CL |
|---|---|---|---|---|
| 35 | 300 | 10 | | |
| | 100 | 0 | | |
| | 30 | 5 | | |
| | 10 | 0 | | |
| | 3 | 0 | | |
| 38 | 1000 | | | 95 |
| | 300 | 50 | 60 | |
| | 100 | 47 | 25 | |
| | 30 | 15 | 5 | |
| | 10 | 16 | 0 | |
| 43 | 1000 | 10 | | 15 |
| | 300 | 5 | | |
| | 100 | 5 | | |
| | 30 | 5 | | |
| | 10 | 0 | | |
| 45 | 300 | 0 | | |
| | 100 | 0 | | |
| | 30 | 0 | | |
| | 10 | 0 | | |
| | 3 | 0 | | |
| 47 | 1000 | 100 | | |
| | 300 | 87 | 15 | |
| | 100 | 79 | 0 | |
| | 30 | 30 | 0 | |
| | 10 | 11 | 0 | |
| 48 | 300 | 100 (95) | | |
| | 100 | 25 (78) | | |
| | 30 | 0 (37) | | |
| | 10 | 0 (5) | | |
| | 3 | 0 (11) | | |
| 50 | 1000 | 95 | | 55 |
| | 300 | 60 | | |
| | 100 | 25 | | |
| | 30 | 10 | | |
| | 10 | 5 | | |
| 56 | 300 | 95 | | |
| | 100 | 25 | | |
| | 30 | 22 | | |
| | 10 | 0 | | |
| | 3 | 5 | | |
| 62 | 3000 | 5 | 0 | 16 |
| | 1000 | 0 | 0 | 5 |
| | 300 | 0 | 0 | 10 |
| | 100 | 0 | 0 | 0 |
| | 30 | 0 | 0 | 15 |
| 65 | 3000 | 80 | 0 | 58 |
| | 1000 | 11 | 0 | 33 |
| | 300 | 5 | 0 | 32 |
| | 100 | 0 | 0 | 17 |
| | 30 | 0 | 0 | 16 |
| | 3000 | | | 33 |
| | 1000 | | | 20 |
| | 300 | | | 10 |
| | 100 | | | 15 |
| | 30 | | | 0 |
| 66 | 1000 | | 0 | 10 |
| | 300 | 5 | 0 | 10 |
| | 100 | 0 | 0 | 16 |
| | 30 | 0 | 0 | 5 |
| | 10 | 0 | 0 | 0 |
| | 3 | 0 | | |
| 67 | 3000 | | | 100 |
| | 1000 | 80 | 45 | 100 |
| | 300 | 42 | 0 | 95 |
| | 100 | 11 | 0 | 55 |
| | 30 | 0 | 0 | 25 |
| | 10 | 0 | 0 | |
| | 3000 | 95 | | |
| | 1000 | 85 | | |
| | 300 | 15 | | |
| | 100 | 0 | | |
| | 30 | 0 | | |
| 69 | 1000 | 25 | 0 | 45 |
| | 300 | 0 | 0 | 20 |
| | 100 | 0 | 0 | 0 |
| | 30 | 0 | 0 | 0 |
| | 10 | 0 | 0 | 11 |
| 70 | 1000 | | 0 | 16 |
| | 300 | 6 | 0 | 5 |
| | 100 | 5 | 0 | 0 |
| | 30 | 0 | 0 | 0 |
| | 10 | 5 | 0 | 5 |
| | 3 | 5 | | |
| 71 | 1000 | 75 | | |
| 74 | 3000 | 54 | 95 | 70 |
| | 1000 | 22 | 20 | 65 |
| | 300 | 5 | 5 | 50 |
| | 100 | 0 | 0 | 25 |
| | 30 | 0 | 0 | 25 |
| 77 | 1000 | 0 | 0 | 22 |
| | 300 | 0 | 0 | 16 |
| | 100 | 0 | 0 | 0 |
| | 30 | 5 | 0 | 5 |
| | 10 | 5 | 0 | 0 |
| 78 | 3000 | 0 | 0 | 20 |
| | 1000 | 0 | 0 | 28 |
| | 300 | 0 | 0 | 37 |
| | 100 | 0 | 0 | 22 |
| | 30 | 0 | 0 | 26 |
| | 3000 | | | 21 |
| | 1000 | | | 6 |
| | 300 | | | 6 |
| | 100 | | | 6 |
| | 30 | | | 10 |
| | 3000 | | | 25 |
| | 1000 | | | 5 |
| | 300 | | | 16 |
| | 100 | | | 5 |
| | 30 | | | 15 |
| 79 | 3000 | 15 | 84 | 33 |
| | 1000 | 0 | 42 | 47 |
| | 300 | 0 | 10 | 35 |
| | 100 | 5 | 0 | 20 |
| | 30 | 11 | 0 | 6 |
| | 3000 | | | 65 |
| | 1000 | | | 55 |
| | 300 | | | 40 |
| | 100 | | | 30 |
| | 30 | | | 25 |
| 90 | 1000 | | 0 | 0 |
| | 300 | 5 | 0 | 0 |
| | 100 | 0 | 0 | 0 |
| | 30 | 5 | 0 | 0 |
| | 10 | 6 | 0 | 0 |
| | 3 | 5 | | |
| 96 | 3000 | 0 | 0 | 50 |
| | 1000 | 11 | 0 | 45 |
| | 300 | 0 | 0 | 40 |
| | 100 | 0 | 0 | 15 |
| | 30 | 0 | 0 | 15 |
| 97 | 1000 | 95 | 95 | 89 |
| | 300 | 95 | 30 | 65 |
| | 100 | 60 | 10 | 20 |
| | 30 | 16 | 0 | 5 |
| | 10 | 5 | 0 | 5 |
| | 300 | 95 | | |
| | 100 | 25 | | |
| | 30 | 22 | | |
| | 10 | 0 | | |
| | 3 | 5 | | |
| 99 | 1000 | 0 | 0 | 15 |
| | 300 | 0 | 0 | 21 |
| | 100 | 0 | 0 | 20 |
| | 30 | 0 | 0 | 0 |

TABLE 3-continued

INSECTICIDAL ACTIVITY OF 5-SUBSTITUTED-2, 4-DIAMINOPYRIMIDINES APPLIED AS FOLIAR SPRAYS

| Cmpd No. | Rate of Application (ppm) | Percent Mortality[1] TBW | BAW | CL |
|---|---|---|---|---|
| | 10 | 0 | 0 | 10 |
| 100 | 3000 | 50 | 16 | 20 |
| | 1000 | 20 | 0 | 5 |
| | 300 | 0 | 0 | 5 |
| | 100 | 11 | 0 | 10 |
| | 30 | 0 | 0 | 5 |
| 102 | 3000 | 0 | 5 | 11 |
| | 1000 | 0 | 0 | 10 |
| | 300 | 0 | 0 | 10 |
| | 100 | 0 | 0 | 15 |
| | 30 | 0 | 0 | 5 |
| 104 | 1000 | 25 | 0 | 20 |
| | 300 | 0 | 0 | 10 |
| | 100 | 0 | 0 | 10 |
| | 30 | 5 | 0 | 5 |
| | 10 | 0 | 0 | 5 |
| 110 | 1000 | 100 | 100 | 100 |
| | 300 | 100 | 100 | 100 |
| | 100 | 100 (100) | 85 | 70 (85) |
| | 30 | 95 (95) | 75 | 65 (75) |
| | 10 | 78 (80) | 6 | 85 (65) |
| | 3 | (16) | | (25) |
| | 1 | (0) | | (5) |
| 114 | 3000 | 100 | 95 | 100 |
| | 1000 | 100 | 70 | 100 |
| | 300 | 100 (100) | 10 | 95 |
| | 100 | 85 (95) | 0 | 75 |
| | 30 | 68 (40) | 0 | 44 |
| | 10 | (10) | | |
| | 3 | (0) | | |
| 115 | 3000 | 100 | | |
| | 1000 | 94 | | |
| | 300 | 39 (58) | 5 | 75 |
| | 100 | 25 (5) | 0 | 70 |
| | 30 | 11 (5) | 0 | 55 |
| | 10 | (6) | 0 | 15 |
| | 3 | (15) | 0 | 11 |
| 116 | 3000 | 100 | 100 | 100 |
| | 1000 | 88 | 80 | 100 |
| | 300 | 33 (21) | 37 | 95 (85) |
| | 100 | 25 (5) | 5 | 61 (63) |
| | 30 | 11 (5) | 5 | 56 (32) |
| | 10 | (10) | | (25) |
| | 3 | | | (16) |
| 117 | 300 | 100 | 100 | 95 |
| | 100 | 100 | 90 | 90 |
| | 30 | 95 | 45 | 90 |
| | 10 | 53 | 5 | 80 |
| | 3 | 3 | 0 | 10 |
| 118 | 1000 | 100 | 100 | |
| | 300 | 100 | 100 (95) | 100 |
| | 100 | 95 | 80 (65) | 89 (100) |
| | 30 | 83 | 20 (26) | 95 (85) |
| | 10 | 53 | 5 (0) | 95 (75) |
| | 3 | | (0) | 42 (33) |
| | 1 | | | (20) |
| 120 | 1000 | 100 | 100 (5) | 95 |
| | 300 | 100 | 11 (0) | 70 |
| | 100 | 95 | 10 (0) | 55 |
| | 30 | 60 | 0 (0) | 37 |
| | 10 | 6 | 0 (0) | 5 |
| 121 | 3000 | 100 | 95 (79) | 100 |
| | 1000 | 100 | 16 (40) | 74 |
| | 300 | 85 | 0 (5) | 65 |
| | 100 | 38 | 0 (0) | 35 |
| | 30 | 20 | 0 (0) | 15 |
| 122 | 1000 | 100 | 100 | 100 |
| | 300 | 100 (95) | 82 | 100 |
| | 100 | 75 (60) | 11 | 75 |
| | 30 | 30 (6) | 11 | 30 |
| | 10 | 11 (5) | 10 | 11 |
| | 3 | (0) | | |
| 123 | 1000 | 100 | 95 | 89 |
| | 300 | 100 | 32 | 75 |
| | 100 | 85 | 5 | 12 |
| | 30 | 56 | 0 | 16 |
| | 10 | 12 | 0 | 0 |
| 124 | 1000 | 95 | 0 | 75 |
| | 300 | 85 | 0 | 35 |
| | 100 | 45 | 0 | 20 |
| | 30 | 17 | 0 | 10 |
| | 10 | 0 | 0 | 15 |
| 125 | 1000 | 100 | 44 | 45 |
| | 300 | 100 | 15 | 58 |
| | 100 | 85 | 0 | 40 |
| | 30 | 56 | 5 | 5 |
| | 10 | 12 | 0 | 5 |
| 128 | 3000 | | 95 | 100 |
| | 1000 | 100 | 20 (55) | 95 (33) |
| | 300 | 100 | 5 (15) | 80 (50) |
| | 100 | 89 | 0 (0) | 70 (20) |
| | 30 | 45 | 0 (0) | 20 (20) |
| | 10 | 5 | (0) | (15) |
| 130 | 3000 | 100 | 20 | 90 |
| | 1000 | 88 | 0 | 60 |
| | 300 | 33 | 0 | 5 |
| | 100 | 11 | 0 | 10 |
| | 30 | 5 | 0 | 10 |
| 131 | 3000 | 100 | 95 | 90 |
| | 1000 | 90 | 50 | 95 |
| | 300 | 72 | 5 | 55 |
| | 100 | 10 | 0 | 25 |
| | 30 | 5 | 0 | 0 |
| 133 | 3000 | 85 | 85 | 100 |
| | 1000 | 70 | 16 | 90 |
| | 300 | 30 | 10 | 65 |
| | 100 | 5 | 0 | 40 |
| | 30 | 0 | 10 | 20 |
| 135 | 3000 | | | 95 |
| | 1000 | 89 | 89 | 65 (29) |
| | 300 | 74 | 50 | 42 (47) |
| | 100 | 25 | 5 | 26 (25) |
| | 30 | 0 | 0 | 10 (30) |
| | 10 | 0 | 0 | (5) |
| 136 | 1000 | 100 | 100 | 100 |
| | 300 | 100 | 100 | 100 |
| | 100 | 100 | 89 | 100 |
| | 30 | 100 (100) | 60 | 95 (100) |
| | 10 | 100 (90) | 28 | 95 (90) |
| | 3 | (67) | | (90) |
| | 1 | (16) | | (45) |
| | 0.3 | (0) | | (25) |
| 139 | 1000 | 100 | 100 | 100 |
| | 300 | 100 | 100 | 100 |
| | 100 | 100 (100) | 75 | 100 (100) |
| | 30 | 100 (95) | 45 | 100 (95) |
| | 10 | 95 (50) | 5 | 95 (90) |
| | 3 | (20) | | (60) |
| | 1 | (26) | | (16) |
| 140 | 1000 | 100 | 100 | 100 |
| | 300 | 100 | 100 | 100 |
| | 100 | 100 | 95 | 95 |
| | 30 | 95 (90) | 40 | 85 (95) |
| | 10 | 95 (68) | 15 | 90 (95) |
| | 3 | (26) | | (75) |
| | 1 | (6) | | (25) |
| | 0.3 | (5) | | (5) |
| 141 | 100 | 100 | 60 | 0 |
| | 30 | 95 | 25 | 45 |
| | 10 | 50 | 5 | 20 |
| | 3 | 26 | 0 | 5 |
| | 1 | 10 | 0 | 10 |
| | 300 | | 100 | 85 |
| | 100 | 100 | 95 | 79 |

TABLE 3-continued

INSECTICIDAL ACTIVITY OF 5-SUBSTITUTED-2, 4-DIAMINOPYRIMIDINES APPLIED AS FOLIAR SPRAYS

| Cmpd No. | Rate of Application (ppm) | Percent Mortality[1] TBW | BAW | CL |
|---|---|---|---|---|
|  | 30 | 90 | 20 | 35 |
|  | 10 | 90 | 5 | 15 |
|  | 3 | 16 | 0 | 10 |
|  | 1 | 16 |  |  |
| 143 | 1000 | 100 | 100 | 89 |
|  | 300 | 100 | 95 | 95 |
|  | 100 | 100 | 25 | 75 |
|  | 30 | 79 | 5 | 58 |
|  | 10 | 74 | 11 | 10 |
|  | 100 | 100 |  |  |
|  | 30 | 95 |  |  |
|  | 10 | 47 |  |  |
|  | 3 | 15 |  |  |
|  | 1 | 0 |  |  |
| 144 | 1000 | 100 | 100 | 100 |
|  | 300 | 100 | 100 | 95 |
|  | 100 | 95 | 95 | 85 |
|  | 30 | 19 | 65 | 85 |
|  | 10 | 6 | 5 | 20 |
| 148 | 300 | 33 | 63 | 95 |
|  | 100 | 7 | 11 | 60 |
|  | 30 | 0 | 5 | 5 |
|  | 10 | 6 | 0 | 5 |
|  | 3 | 0 | 0 | 0 |
| 149 | 100 | 95 | 73 | 95 |
|  | 30 | 90 | 6 | 71 |
|  | 10 | 63 | 0 | 65 |
|  | 3 | 19 | 0 | 25 |
|  | 1 | 0 | 0 | 0 |
| 150 | 100 | 35 | 0 | 95 |
|  | 30 | 28 | 0 | 50 |
|  | 10 | 0 | 0 | 5 |
|  | 3 | 0 | 0 | 0 |
|  | 1 | 0 | 0 | 0 |
| 151 | 1000 | 100 | 84 | 47 |
|  | 300 | 90 | 32 | 16 |
|  | 100 | 79 | 5 | 5 |
|  | 30 | 18 | 0 | 0 |
|  | 10 | 5 | 0 | 0 |
| 152 | 1000 | 100 | 89 | 100 |
|  | 300 | 100 | 10 | 40 |
|  | 100 | 94 | 5 | 95 |
|  | 30 | 72 | 0 | 65 |
|  | 10 | 15 | 0 | 25 |
|  | 1000 |  | 100 | 95 |
|  | 300 |  | 74 | 60 |
|  | 100 |  | 5 | 40 |
|  | 30 |  | 5 | 40 |
|  | 10 |  |  | 32 |
|  | 1000 |  |  | 95 |
|  | 300 |  |  | 78 |
|  | 100 |  |  | 80 |
|  | 30 |  |  | 85 |
|  | 10 |  |  | 35 |
| 153 | 1000 | 75 | 53 | 21 |
|  | 300 | 40 | 5 | 20 |
|  | 100 | 5 | 0 | 5 |
|  | 30 | 5 | 0 | 5 |
|  | 10 | 0 | 0 | 10 |
| 154 | 3000 | 55 | 25 | 89 |
|  | 1000 | 25 | 5 | 26 |
|  | 300 | 5 | 0 | 15 |
|  | 100 | 0 | 5 | 5 |
|  | 30 | 0 | 0 | 5 |
| 155 | 1000 | 100 | 100 | 100 |
|  | 300 | 100 | 100 | 89 |
|  | 100 | 100 | 95 | 80 |
|  | 30 | 94 | 20 | 95 |
|  | 10 | 100 | 0 | 80 |
|  | 100 | 100 | 95 | 75 |
|  | 30 | 95 | 94 | 67 |
|  | 10 | 84 | 10 | 70 |
|  | 3 | 5 | 5 | 30 |
|  | 1 | 0 | 0 | 5 |
| 156 | 3000 | 100 | 95 | 100 |
|  | 1000 | 80 | 80 | 75 |
|  | 300 | 63 | 10 | 80 |
|  | 100 | 5 | 0 | 60 |
|  | 30 | 15 | 0 | 10 |
| 157 | 1000 | 100 | 95 | 95 |
|  | 300 | 75 | 53 | 76 |
|  | 100 | 79 | 11 | 84 |
|  | 30 | 39 | 0 | 10 |
|  | 10 | 10 | 16 | 10 |
| 158 | 1000 | 42 | 32 | 100 |
|  | 300 | 24 | 0 | 28 |
|  | 100 | 5 | 0 | 5 |
|  | 30 | 0 | 0 | 0 |
|  | 10 | 0 | 0 | 0 |
| 159 | 3000 | 100 | 95 | 89 |
|  | 1000 | 83 | 58 | 50 |
|  | 300 | 68 | 16 | 45 |
|  | 100 | 25 | 0 | 17 |
|  | 30 | 7 | 0 | 0 |
| 160 | 3000 | 79 | 26 | 30 |
|  | 1000 | 11 | 0 | 0 |
|  | 300 | 6 | 5 | 5 |
|  | 100 | 0 | 0 | 15 |
|  | 30 | 0 | 11 | 10 |
| 161 | 3000 | 100 | 58 | 95 |
|  | 1000 | 90 | 10 | 37 |
|  | 300 | 58 | 5 | 5 |
|  | 100 | 24 | 0 | 5 |
|  | 30 | 0 | 5 | 10 |
| 164 | 1000 | 100 | 100 | 100 |
|  | 300 | 93 | 100 | 47 |
|  | 100 | 53 | 90 | 90 |
|  | 30 | 12 | 30 | 50 |
|  | 10 | 0 | 5 | 5 |
|  | 1000 | 100 | 100 | 95 |
|  | 300 | 82 | 100 | 75 |
|  | 100 | 79 | 95 | 85 |
|  | 30 | 37 | 32 | 74 |
|  | 10 | 5 | 5 | 10 |
| 170 | 1000 | 100 | 100 | 80 |
|  | 300 | 95 | 95 | 24 |
|  | 100 | 38 | 53 | 26 |
|  | 30 | 5 | 5 | 5 |
|  | 10 | 0 | 0 | 5 |
| 172 | 3000 | 32 | 47 | 85 |
|  | 1000 | 26 | 15 | 75 |
|  | 300 | 5 | 0 | 60 |
|  | 100 | 11 | 5 | 20 |
|  | 30 | 5 | 5 | 5 |

[1]tobacco budworm = TBW
beet armyworm = BAW
cabbage looper = CL
[2]The numbers in parenthesis represent the results of a second test

TABLE 4

CORRELATION OF GROWTH INHIBITION $pI_{50}$ VALUES FROM THE DIET TEST WITH TOBACCO BUDWORM MORTALITY IN THE FOLIAR TEST[1]

| Cmpd No. | Growth Inhibition $pI_{50}$ | Foliar Test Rate of Appln.[2] | Mortality |
|---|---|---|---|
| 14 | 4.5 | 1000 ppm | 50 |
|  |  | 300 | 26 |

TABLE 4-continued

CORRELATION OF GROWTH INHIBITION $pI_{50}$ VALUES FROM THE DIET TEST WITH TOBACCO BUDWORM MORTALITY IN THE FOLIAR TEST[1]

| Cmpd No. | Growth Inhibition $pI_{50}$ | Foliar Test | |
|---|---|---|---|
| | | Rate of Appln.[2] | Mortality |
| 17 | <3.5 | 300 | 0 |
| 21 | 4.4 | 1000 | 10 |
| 32 | 5.2 | 1000 | 100 |
| | | 300 | 85 |
| 34 | 6.4 | 300 | 100 |
| | | 100 | 100 |
| 35 | 4.6 | 300 | 10 |
| | | 100 | 0 |
| 38 | 4.9 (5.9)[3] | 300 | 50 |
| | | 100 | 47 |
| 43 | 5.1 (3.0) | 1000 | 10 |
| | | 300 | 5 |
| 45 | 3.6 | 300 | 0 |
| 47 | 5.9 (6.1) | 1000 | 100 |
| | | 300 | 87 |
| 48 | 6.0 | 300 | 100 (95) |
| | | 100 | 25 (78) |
| 50 | 6.0 | 1000 | 95 |
| | | 300 | 60 |
| 56 | 5.7 | 300 | 95 |
| | | 100 | 25 |

[1]These data were compiled from Tables 2 and 3.
[2]The two highest rates of application, or the only rate of application tested are shown here.
[3]The number in the parenthesis is a value derived from a second test.

We claim:

1. An insecticidal composition comprising, in admixture with an agriculturally acceptable carrier, and a surface-active agent an insecticidally effective amount of a compound of the formula:

$$\text{(I)}$$

wherein

R is naphthyl, or substituted naphthyl of the formula:

$$\text{(IV)}$$

wherein $V^2$, $W^2$, $X^2$, $Y^2$, and $Z^2$ are independently selected from hydrogen, halogen, lower alkyl, lower haloalkyl, lower alkylsulfonyl, cyano, and aminocarbonyl;

and wherein $R^1$ is hydrogen, lower alkyl, amino, phenyl, or phenyl lower alkyl;

$R^2$, $R^3$, $R^7$ and $R^8$ are independently selected from hydrogen, lower alkyl, lower alkylcarbonyl, and lower alkoxycarbonyl;

or $R^2$ and $R^3$, taken together, form the group —$R^6$—O—$R^6$—, wherein $R^6$ is lower alkylene;

m is 0 or 1;

n is 2 to 11; and p is 0 or 1, and agriculturally acceptable salts thereof.

2. The composition of claim 1, wherein m and p are 0;

n is 2 to 10;

R is naphthyl or substituted naphthyl;

$R^1$ is hydrogen, lower alkyl, or amino; and $R^2$, $R^3$, $R^7$, and $R^8$ are hydrogen, lower alkyl, lower alkylcarbonyl, or lower alkoxycarbonyl.

3. The composition of claim 1 wherein m and p are 0;

n is 3 or 4;

R is naphth-1-yl;

$R^1$ is hydrogen, lower alkyl or amino;

$R^2$ is hydrogen, lower alkyl, lower alkylcarbonyl, or lower alkoxycarbonyl; and $R^3$, $R^7$, and $R^8$ are hydrogen, lower alkylcarbonyl, or lower alkoxycarbonyl.

4. The composition of claim 3 wherein V, X, and Y are all chloro or all methyl, and the remaining substituents are hydrogen.

5. The composition of claim 1 where R is naphthyl.

6. The composition of claim 1 wherein the insecticide is 2,4-diamino-5-[3-(naphth-1-yl)propyl]pyrimidine.

7. A method for controlling insects which comprises applying to the locus where control is desired an insecticidal amount of the composition of claim 1.

8. A method for controlling insects which comprises applying to the locus where control is desired an insecticidal amount of the composition of claim 2.

9. A method for controlling insects which comprises applying to the locus where control is desired an insecticidal amount of the composition of claim 3.

10. A method for controlling insects which comprises applying to the locus where control is desired an insecticidal amount of the composition of claim 4.

* * * * *